(12) United States Patent
Legrain et al.

(10) Patent No.: US 6,913,886 B2
(45) Date of Patent: *Jul. 5, 2005

(54) FAST AND EXHAUSTIVE METHOD FOR SELECTING A PREY POLYPEPTIDE INTERACTING WITH A BAIT POLYPEPTIDE OF INTEREST: APPLICATION TO THE CONSTRUCTION OF MAPS OF INTERACTORS POLYPEPTIDES

(75) Inventors: Pierre Legrain, Paris (FR); Micheline Fromont, Villejuif (FR); Jean-Christophe Rain, Puteaux (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/279,964

(22) Filed: Oct. 25, 2002

(65) Prior Publication Data

US 2003/0134268 A1 Jul. 17, 2003

Related U.S. Application Data

(63) Continuation of application No. 09/637,240, filed on Aug. 14, 2000, now Pat. No. 6,531,284, which is a continuation of application No. 09/025,151, filed on Feb. 18, 1998, now Pat. No. 6,187,535.

(51) Int. Cl.[7] .......................... C12Q 1/68; G01N 33/53
(52) U.S. Cl. ........................ 435/6; 435/7.31; 435/69.1; 435/71.1
(58) Field of Search ......................... 435/6, 29, 254.2, 435/320.1, 170, 69.1, 91.1, 91.2; 536/22.1, 23.1, 24.3–24.33

(56) References Cited

U.S. PATENT DOCUMENTS

| | | |
|---|---|---|
| 5,283,173 A | 2/1994 | Fields et al. |
| 5,468,614 A | 11/1995 | Fields et al. |
| 5,667,973 A | 9/1997 | Fields et al. |
| 5,733,731 A | 3/1998 | Schatz et al. |
| 5,834,234 A | 11/1998 | Gallo |
| 5,986,055 A | 11/1999 | Yang et al. |
| 6,033,847 A | 3/2000 | Sherr et al. |

FOREIGN PATENT DOCUMENTS

| | | |
|---|---|---|
| WO | WO 92/10588 | 6/1992 |
| WO | WO 96/29429 | 9/1996 |
| WO | WO 96/40987 | 12/1996 |
| WO | WO 97/10365 | 3/1997 |
| WO | WO 97/27317 | 7/1997 |
| WO | WO 97/29212 | 8/1997 |
| WO | WO 97/41255 | 11/1997 |

OTHER PUBLICATIONS

Amberg, David Co. et al., "Defining Protein Interactions with Yeast Action In Vivo," *Structural Biology*, Vl. 2, No. 1 (Jan. 1995).

Bartel, Paul L. et al., "A Protein Linkage Map of *Escherichia coli* Bacteriophage T7," *Nature Genetics*, vol. 12, pp. 72–77 (Jan. 1996).
Bendixen et al., *NAR*, vol. 22, No. 9, pp. 1778–1779.
Brachmann, Rainer K. et al., "Tag Games in Yeast: The Two–Hybrid System and Beyond," *Current Opinion in Biotechnology*, vol. 8, pp. 561–568 (1997).
Brent, Roger, "Looms to Weave Genomic Nets," *Nature Genetics*, vol. 16, pp. 216–217 (Jul. 1997).
Chee, Mark et al., "Accessing Genetic Information with High–Density DNA Arrays," *Science*, vol. 274, pp. 610–614 (Oct. 25, 1996).
Cherest, Helene et al., "Transcriptional Regulation of the MET3 Gene of *Saccharomyces cerevisiae*," *Gene*, vol. 34, pp. 269–281 (1985).
Durfee et al., *Genes & Development*, vol. 7, pp. 555–569.
Elledge, Stephen J. et al., "YES: A Multifunctional cDNA Expression Vector for the Isolation of Genes by Complementation of Yeast and *Escherichia coli* Mutations," *Genetics*, vol. 88, pp. 1731–1735 (Mar. 1991).
Fields, Stanley et al., "A Novel Genetic System to Detect Protein–Protein Interactions," *Nature*, vol. 340, pp. 245–246 (Jul. 20, 1989).
Fields, Stanley et al., "The Two–Hybrid System: An Assay for Protein–Protein Interactions," *TIG*, vol. 10, No. 8, pp. 286–292 (Aug. 1994).
James et al., *Genetics*, vol. 144, pp. 1425–1436.
Klein, Robert D. et al., "Selection for Genes Encoding Secreted Proteins and Receptors," *Genetics*, vol. 93, pp. 7108–7113 (Jul. 1996).
Kroll, Eugene S. et al., "Establishing Genetic Interactions by a Synthetic Dosage Lethality Phenotype," *Genetics*, vol. 143, pp. 95–102 (May 1996).
Lecrenier et al., *Bioassays*, vol. 20.1, pp. 1–6.
Lewin, B., et al., *Genes*, pp. 1101–1102.
Fromont–Racine, Micheline et al., Toward a Functional Analysis of the Yeast Genome Through Exhaustive Two–Hybrid Screens,: *Genetics*, vol. 16, pp. 277–282 (Jul. 1997).

(Continued)

*Primary Examiner*—Kenneth R. Horlick
(74) *Attorney, Agent, or Firm*—Finnegan, Henderson, Farabow, Garrett & Dunner, L.L.P.

(57) ABSTRACT

The present invention is directed to a method for selecting a prey polypeptide that is able to interact with a bait polypeptide of interest, to a prey polynucleotide encoding the prey polypeptide as well as to the prey polypeptide itself. The invention also concerns plasmids used for performing the method of the invention as well as prokaryotic or eukaryotic recombinant host organisms containing such plasmids and also a collection of said recombinant host organisms consisting in a DNA library, such as a collection of recombinant haploid *Saccharomyces cerevisiae*. Finally, the invention is also directed to a technical medium containing the whole information concerning the interactions between metabolically related bait and prey polypeptides and/or polynucleotides coding for bait and prey polypeptides.

5 Claims, 10 Drawing Sheets

OTHER PUBLICATIONS

Shalon; Dari et al., "A DNA Microarray System for Analyzing Complex DNA Samples Using Two–Color Fluorescent Probe Hybridization," *Genome Research*, pp. 639–645 (1996).

Stearns, Tim et al., "Yeast Mutants Sensitive to Antimicrotubule Drugs Define Three Genes That Affect Microtubule Function," *Genetics*, vol. 124, pp. 251–262 (Feb. 1990).

Transy, Catherine et al., "Two Two–Hybrid: An In Vivo Protein–Protein Interaction Assay," *Molecular Biology Reports*, vol. 21, pp. 119–127 (1995).

Vidal, Marc et al., "Genetic Characterization of a Mammalian Protein–Protein Interaction Domain by Using a Yeast Reverse Two–Hybrid System," *Genetics*, vol. 93, pp. 10321–10326 (Sep. 1996).

Vidal, Marc et al., "Reverse Two–Hybrid and One–Hybrid Systems to Detect Dissociation of Protein–Protein and DNA–Protein Interactions," Genetics, vol. 93, pp. 10315–10320 (Sep. 1996).

White, Michael A., et al., "The Yeast Two–Hybrid System: Forward and Reverse," *Genetics*, vol. 93, pp. 10001–10003 (Sep. 1996).

Wodicka, Lisa et al., "Genome–Wide Expression Monitoring in *Saccharomyces cerevisiae,*" *Nature Biotechnology*, vol. 15, pp. 1359–1367 (Dec. 1997).

FIG. 6

SEQUENCE LISTING

```
<160> NUMBER OF SEQ ID NOS: 29
<210> SEQ ID NO 1
<211> LENGTH: 25
<212> TYPE: DNA
<213> ORGANISM: Saccharomyces cerevisiae

<400> SEQUENCE: 1
cgcgtttgga atcactacag ggatg                                          25

<210> SEQ ID NO 2
<211> LENGTH: 25
<212> TYPE: DNA
<213> ORGANISM: Saccharomyces cerevisiae

<400> SEQUENCE: 2
gaaattgaga tggtgcacga tgcac                                          25

<210> SEQ ID NO 3
<211> LENGTH: 20
<212> TYPE: DNA
<213> ORGANISM: Saccharomyces cerevisiae

<400> SEQUENCE: 3
ggcttaccca tacgatgttc                                                20

<210> SEQ ID NO 4
<211> LENGTH: 16
<212> TYPE: DNA
<213> ORGANISM: Saccharomyces cerevisiae

<400> SEQUENCE: 4
atcccggacg aaggcc                                                    16

<210> SEQ ID NO 5
<211> LENGTH: 13
<212> TYPE: DNA
<213> ORGANISM: Saccharomyces cerevisiae

<400> SEQUENCE: 5
ggccttcgtc cgg                                                       13

<210> SEQ ID NO 6
<211> LENGTH: 79
<212> TYPE: PRT
<213> ORGANISM: Saccharomyces cerevisiae

<400> SEQUENCE: 6

Met Leu Gln His Ile Asp Tyr Arg Met Arg Cys Ile Leu Gln Asp Gly
  1               5                  10                  15
```

```
Arg Ile Phe Ile Gly Thr Phe Lys Ala Phe Asp Lys His Met Asn Leu
             20                  25                  30

Ile Leu Cys Asp Cys Asp Glu Phe Arg Lys Ile Lys Pro Lys Asn Ser
         35                  40                  45

Lys Gln Ala Glu Arg Glu Lys Arg Val Leu Gly Leu Val Leu Leu
     50                  55                  60

Arg Gly Glu Asn Leu Val Ser Met Thr Val Glu Gly Pro Pro Pro
 65                  70                  75
```

<210> SEQ ID NO 7
<211> LENGTH: 79
<212> TYPE: PRT
<213> ORGANISM: Saccharomyces cerevisiae

<400> SEQUENCE: 7

```
Leu Ala Asn Leu Ile Asp Tyr Lys Leu Arg Val Leu Thr Gln Asp Gly
 1               5                  10                  15

Arg Val Tyr Ile Gly Gln Leu Met Ala Phe Asp Lys His Met Asn Leu
             20                  25                  30

Val Leu Asn Glu Cys Ile Glu Glu Arg Val Pro Lys Thr Gln Leu Asp
         35                  40                  45

Lys Leu Arg Pro Arg Lys Asp Ser Lys Asp Leu Gly Leu Thr Ile Leu
     50                  55                  60

Arg Gly Glu Gln Ile Leu Ser Thr Val Val Glu Asp Lys Pro Leu
 65                  70                  75
```

<210> SEQ ID NO 8
<211> LENGTH: 74
<212> TYPE: PRT
<213> ORGANISM: Saccharomyces cerevisiae

<400> SEQUENCE: 8

```
Ile Val Ser Ser Val Asp Arg Lys Ile Phe Val Leu Leu Arg Asp Gly
 1               5                  10                  15

Arg Met Leu Phe Gly Val Leu Arg Thr Phe Asp Gln Tyr Ala Asn Leu
             20                  25                  30

Ile Leu Gln Asp Cys Val Glu Arg Ile Tyr Phe Ser Glu Glu Asn Lys
         35                  40                  45

Tyr Ala Glu Glu Asp Arg Gly Ile Phe Met Ile Arg Gly Glu Asn Val
     50                  55                  60

Val Met Leu Gly Glu Val Asp Ile Asp Lys
 65                  70
```

<210> SEQ ID NO 9
<211> LENGTH: 69
<212> TYPE: PRT
<213> ORGANISM: Saccharomyces cerevisiae

<400> SEQUENCE: 9

```
Leu Met Lys Leu Ser His Glu Thr Val Thr Ile Glu Leu Lys Asn Gly
 1               5                  10                  15

Thr Gln Val His Gly Thr Ile Thr Gly Val Asp Val Ser Met Asn Thr
             20                  25                  30

His Leu Lys Ala Val Lys Met Thr Leu Lys Asn Arg Glu Pro Val Gln
         35                  40                  45

Leu Glu Thr Leu Ser Ile Arg Gly Asn Asn Ile Arg Tyr Phe Ile Leu
     50                  55                  60
```

-continued

Pro Asp Ser Leu Pro
65

<210> SEQ ID NO 10
<211> LENGTH: 79
<212> TYPE: PRT
<213> ORGANISM: Saccharomyces cerevisiae

<400> SEQUENCE: 10

Leu Lys Lys Leu Arg Asn Glu Gln Val Thr Ile Glu Leu Lys Asn Gly
1               5                  10                  15

Thr Thr Val Trp Gly Thr Leu Gln Ser Val Ser Pro Gln Met Asn Ala
            20                  25                  30

Ile Leu Thr Asp Val Lys Leu Thr Leu Pro Gln Pro Arg Leu Asn Lys
        35                  40                  45

Leu Asn Ser Asn Gly Ile Ala Met Ala Ser Leu Gln Tyr Ile Asn Ile
    50                  55                  60

Arg Gly Asn Thr Ile Arg Gln Ile Ile Leu Pro Asp Ser Leu Asn
65                  70                  75

<210> SEQ ID NO 11
<211> LENGTH: 71
<212> TYPE: PRT
<213> ORGANISM: Saccharomyces cerevisiae

<400> SEQUENCE: 11

Phe Lys Thr Leu Val Asp Gln Glu Val Val Glu Leu Lys Asn Asp
1               5                  10                  15

Ile Glu Ile Lys Gly Thr Leu Gln Ser Val Asp Gln Phe Leu Asn Leu
            20                  25                  30

Lys Leu Asp Asn Ile Ser Cys Thr Asp Glu Lys Lys Tyr Pro His Leu
        35                  40                  45

Gly Ser Val Arg Asn Ile Phe Ile Arg Gly Ser Thr Val Arg Tyr Val
    50                  55                  60

Tyr Leu Asn Lys Asn Met Val
65                  70

<210> SEQ ID NO 12
<211> LENGTH: 79
<212> TYPE: PRT
<213> ORGANISM: Saccharomyces cerevisiae

<400> SEQUENCE: 12

Gln Ser Val Lys Asn Asn Thr Gln Val Leu Ile Asn Cys Arg Asn Asn
1               5                  10                  15

Lys Lys Leu Leu Gly Arg Val Lys Ala Phe Asp Arg His Cys Asn Met
            20                  25                  30

Val Leu Glu Asn Val Lys Glu Met Trp Thr Glu Val Pro Lys Ser Gly
        35                  40                  45

Lys Gly Lys Lys Lys Ser Lys Pro Val Asn Ile Ser Lys Met Phe Leu
    50                  55                  60

Arg Gly Asp Ser Val Ile Val Val Leu Arg Asn Pro Leu Ile Ala
65                  70                  75

<210> SEQ ID NO 13
<211> LENGTH: 75
<212> TYPE: PRT
<213> ORGANISM: Saccharomyces cerevisiae

<400> SEQUENCE: 13

```
Asp Ala Met Val Thr Arg Thr Pro Val Ile Ile Ser Leu Arg Asn Asn
 1               5                  10                  15

His Lys Ile Ile Ala Arg Val Lys Ala Phe Asp Arg His Cys Asn Met
             20                  25                  30

Val Leu Glu Asn Val Lys Glu Leu Trp Thr Glu Lys Lys Gly Lys Asn
         35                  40                  45

Val Ile Asn Arg Glu Arg Phe Ile Ser Lys Leu Phe Leu Arg Gly Asp
     50                  55                  60

Ser Val Ile Val Val Leu Lys Thr Pro Val Glu
 65                  70                  75

<210> SEQ ID NO 14
<211> LENGTH: 76
<212> TYPE: PRT
<213> ORGANISM: Saccharomyces cerevisiae

<400> SEQUENCE: 14

Leu Lys Leu Asn Leu Asp Glu Arg Val Tyr Ile Lys Leu Arg Gly Ala
 1               5                  10                  15

Arg Thr Leu Val Gly Thr Leu Gln Ala Phe Asp Ser His Cys Asn Ile
             20                  25                  30

Val Leu Ser Asp Ala Val Glu Thr Ile Tyr Gln Leu Asn Asn Glu Glu
         35                  40                  45

Leu Ser Glu Ser Glu Arg Arg Cys Glu Met Val Phe Ile Arg Gly Asp
     50                  55                  60

Thr Val Thr Leu Ile Ser Thr Pro Ser Glu Asp Asp
 65                  70                  75

<210> SEQ ID NO 15
<211> LENGTH: 69
<212> TYPE: PRT
<213> ORGANISM: Saccharomyces cerevisiae

<400> SEQUENCE: 15

Leu His Glu Ala Glu Gly His Ile Val Thr Cys Glu Thr Asn Thr Gly
 1               5                  10                  15

Glu Val Tyr Arg Gly Lys Leu Thr Glu Ala Glu Asp Asn Met Asn Cys
             20                  25                  30

Gln Met Ser Asn Ile Thr Val Thr Tyr Arg Asp Gly Arg Val Ala Gln
         35                  40                  45

Leu Glu Gln Val Tyr Ile Arg Gly Ser Lys Ile Arg Phe Leu Ile Leu
     50                  55                  60

Pro Asp Met Leu Lys
 65

<210> SEQ ID NO 16
<211> LENGTH: 69
<212> TYPE: PRT
<213> ORGANISM: Saccharomyces cerevisiae

<400> SEQUENCE: 16

Leu Asn Glu Ala Gln Gly His Ile Val Ser Leu Glu Leu Thr Thr Gly
 1               5                  10                  15

Ala Thr Tyr Arg Gly Lys Leu Val Glu Ser Glu Asp Ser Met Asn Val
             20                  25                  30

Gln Leu Arg Asp Val Ile Ala Thr Glu Pro Gln Gly Ala Val Thr His
         35                  40                  45
```

```
Met Asp Gln Ile Phe Val Arg Gly Ser Gln Ile Lys Phe Ile Val Val
 50                  55                  60

Pro Asp Leu Leu Lys
 65

<210> SEQ ID NO 17
<211> LENGTH: 80
<212> TYPE: PRT
<213> ORGANISM: Saccharomyces cerevisiae

<400> SEQUENCE: 17

Leu Thr Asn Ala Lys Gly Gln Gln Met Gln Ile Glu Leu Lys Asn Gly
  1               5                  10                  15

Glu Ile Ile Gln Gly Ile Leu Thr Asn Val Asp Asn Trp Met Asn Leu
             20                  25                  30

Thr Leu Ser Asn Val Thr Glu Tyr Ser Glu Ser Ala Ile Asn Ser
         35                  40                  45

Glu Asp Asn Ala Glu Ser Ser Lys Ala Val Lys Leu Asn Glu Ile Tyr
 50                  55                  60

Ile Arg Gly Thr Phe Ile Lys Phe Ile Lys Leu Gln Asp Asn Ile Ile
 65                  70                  75                  80

<210> SEQ ID NO 18
<211> LENGTH: 68
<212> TYPE: PRT
<213> ORGANISM: Saccharomyces cerevisiae

<400> SEQUENCE: 18

Leu Gln Asn Arg Ser Arg Ile Gln Val Trp Leu Tyr Glu Gln Val Asn
  1               5                  10                  15

Met Arg Ile Glu Gly Cys Ile Ile Gly Phe Asp Glu Tyr Met Asn Leu
             20                  25                  30

Val Leu Asp Asp Ala Glu Glu Ile His Ser Thr Lys Ser Arg Lys
         35                  40                  45

Gln Leu Gly Arg Ile Met Leu Lys Gly Asp Asn Ile Thr Leu Leu Gln
 50                  55                  60

Ser Val Ser Asn
 65

<210> SEQ ID NO 19
<211> LENGTH: 74
<212> TYPE: PRT
<213> ORGANISM: Saccharomyces cerevisiae

<400> SEQUENCE: 19

Leu Gln Gln Gln Thr Pro Val Thr Ile Trp Leu Phe Glu Gln Ile Gly
  1               5                  10                  15

Ile Arg Ile Lys Gly Lys Ile Val Gly Phe Asp Glu Phe Met Asn Val
             20                  25                  30

Val Ile Asp Glu Ala Val Glu Ile Pro Val Asn Ser Ala Asp Gly Lys
         35                  40                  45

Glu Asp Val Glu Lys Gly Thr Pro Leu Gly Lys Ile Leu Leu Lys Gly
 50                  55                  60

Asp Asn Ile Thr Leu Ile Thr Ser Ala Asp
 65                  70

<210> SEQ ID NO 20
<211> LENGTH: 77
<212> TYPE: PRT
```

<213> ORGANISM: Saccharomyces cerevisiae

<400> SEQUENCE: 20

```
Ile Asp Lys Thr Ile Asn Gln Lys Val Leu Ile Val Leu Gln Ser Asn
  1               5                  10                  15

Arg Glu Phe Glu Gly Thr Leu Val Gly Phe Asp Asp Phe Val Asn Val
             20                  25                  30

Ile Leu Glu Asp Ala Val Glu Trp Leu Ile Asp Pro Glu Asp Glu Ser
         35                  40                  45

Arg Asn Glu Lys Val Met Gln His His Gly Arg Met Leu Leu Ser Gly
     50                  55                  60

Asn Asn Ile Ala Ile Leu Val Pro Gly Gly Lys Lys Thr
 65                  70                  75
```

<210> SEQ ID NO 21
<211> LENGTH: 70
<212> TYPE: PRT
<213> ORGANISM: Saccharomyces cerevisiae

<400> SEQUENCE: 21

```
Leu Asn Gly Leu Thr Gly Lys Pro Val Met Val Lys Leu Lys Trp Gly
  1               5                  10                  15

Met Glu Tyr Lys Gly Tyr Leu Val Ser Val Asp Gly Tyr Met Asn Met
             20                  25                  30

Gln Leu Ala Asn Thr Glu Glu Tyr Ile Asp Gly Ala Leu Ser Gly His
         35                  40                  45

Leu Gly Glu Val Leu Ile Arg Cys Asn Asn Val Leu Tyr Ile Arg Gly
     50                  55                  60

Val Glu Glu Glu Glu Glu
 65                  70
```

<210> SEQ ID NO 22
<211> LENGTH: 68
<212> TYPE: PRT
<213> ORGANISM: Saccharomyces cerevisiae

<400> SEQUENCE: 22

```
Leu Lys Gly Leu Val Asn His Arg Val Gly Val Lys Leu Lys Phe Asn
  1               5                  10                  15

Ser Thr Glu Tyr Arg Gly Thr Leu Val Ser Thr Asp Asn Tyr Phe Asn
             20                  25                  30

Leu Gln Leu Asn Glu Ala Glu Glu Phe Val Ala Gly Val Ser His Gly
         35                  40                  45

Thr Leu Gly Glu Ile Phe Ile Arg Cys Asn Asn Val Leu Tyr Ile Arg
     50                  55                  60

Glu Leu Pro Asn
 65
```

<210> SEQ ID NO 23
<211> LENGTH: 71
<212> TYPE: PRT
<213> ORGANISM: Saccharomyces cerevisiae

<400> SEQUENCE: 23

```
Leu Ser Asp Ile Ile Gly Lys Thr Val Asn Val Lys Leu Ala Ser Gly
  1               5                  10                  15

Leu Leu Tyr Ser Gly Arg Leu Glu Ser Ile Asp Gly Phe Met Asn Val
             20                  25                  30
```

-continued

Ala Leu Ser Ser Ala Thr Glu His Tyr Glu Ser Asn Asn Asn Lys Leu
            35                  40                  45

Leu Asn Lys Phe Asn Ser Asp Val Phe Leu Arg Gly Thr Gln Val Met
        50                  55                  60

Tyr Ile Ser Glu Gln Lys Ile
 65                  70

<210> SEQ ID NO 24
<211> LENGTH: 68
<212> TYPE: PRT
<213> ORGANISM: Saccharomyces cerevisiae

<400> SEQUENCE: 24

Leu Lys Lys Phe Met Asp Lys Lys Leu Ser Leu Lys Leu Asn Gly Gly
 1               5                  10                  15

Arg His Val Gln Gly Ile Leu Arg Gly Phe Asp Pro Phe Met Asn Leu
            20                  25                  30

Val Ile Asp Glu Cys Val Glu Met Ala Thr Ser Gly Gln Gln Asn Asn
        35                  40                  45

Ile Gly Met Val Val Ile Arg Gly Asn Ser Ile Ile Met Leu Glu Ala
    50                  55                  60

Leu Glu Arg Val
 65

<210> SEQ ID NO 25
<211> LENGTH: 71
<212> TYPE: PRT
<213> ORGANISM: Saccharomyces cerevisiae

<400> SEQUENCE: 25

Leu Lys Lys Tyr Met Asp Lys Lys Ile Leu Leu Asn Ile Asn Gly Ser
 1               5                  10                  15

Arg Lys Val Ala Gly Ile Leu Arg Gly Tyr Asp Ile Phe Leu Asn Val
            20                  25                  30

Val Leu Asp Asp Ala Met Glu Ile Asn Gly Glu Asp Pro Ala Asn Asn
        35                  40                  45

His Gln Leu Gly Leu Gln Thr Val Ile Arg Gly Asn Ser Ile Ile Ser
    50                  55                  60

Leu Glu Ala Leu Asp Ala Ile
 65                  70

<210> SEQ ID NO 26
<211> LENGTH: 81
<212> TYPE: PRT
<213> ORGANISM: Saccharomyces cerevisiae

<400> SEQUENCE: 26

Leu Ala Lys Tyr Lys Asp Ser Lys Ile Arg Val Lys Leu Met Gly Gly
 1               5                  10                  15

Lys Leu Val Ile Gly Val Leu Lys Gly Tyr Asp Gln Leu Met Asn Leu
            20                  25                  30

Val Leu Asp Asp Thr Val Glu Tyr Met Ser Asn Pro Asp Asp Glu Asn
        35                  40                  45

Asn Thr Glu Leu Ile Ser Lys Asn Ala Arg Lys Leu Gly Leu Thr Val
    50                  55                  60

Ile Arg Gly Thr Ile Leu Val Ser Leu Ser Ser Ala Glu Gly Ser Asp
 65                  70                  75                  80

Val

<210> SEQ ID NO 27
<211> LENGTH: 67
<212> TYPE: PRT
<213> ORGANISM: Saccharomyces cerevisiae

<400> SEQUENCE: 27

```
Leu Lys Asp Tyr Leu Asn Lys Arg Val Val Ile Ile Lys Val Asp Gly
 1               5                  10                  15

Glu Cys Leu Ile Ala Ser Leu Asn Gly Phe Asp Lys Asn Thr Asn Leu
            20                  25                  30

Phe Ile Thr Asn Val Phe Asn Arg Ile Ser Lys Glu Phe Ile Cys Lys
        35                  40                  45

Ala Gln Leu Leu Arg Gly Ser Glu Ile Ala Leu Val Gly Leu Ile Asp
    50                  55                  60

Ala Glu Asn
 65
```

<210> SEQ ID NO 28
<211> LENGTH: 114
<212> TYPE: DNA
<213> ORGANISM: Saccharomyces cerevisiae

<400> SEQUENCE: 28

```
gagagtagta acaaaggtca agacagttg actgtatcgc cggaatttat ggccatggag      60
gccccgggga tccgtcgacc tgcagccaag ctaattccgg gcgaatttct tatg          114
```

<210> SEQ ID NO 29
<211> LENGTH: 288
<212> TYPE: DNA
<213> ORGANISM: Saccharomyces cerevisiae

<400> SEQUENCE: 29

```
cgcgtttgga atcactacag ggatgtttaa taccactaca atggatgatg tatataacta     60
tctattcgat gatgaagata ccccaccaaa cccaaaaaaa gagatctgta tggcttaccc    120
atacgatgtt ccagattacg ctagcttggg tggtcatatg gccatggagg ccccggggat    180
ccgaattcga gctcgactag ctagctgact cgagagatct atgaatcgta gatactgaaa    240
aaccccgcaa gttcacttca actgtgcatc gtgcaccatc tcaatttc                 288
```

FAST AND EXHAUSTIVE METHOD FOR SELECTING A PREY POLYPEPTIDE INTERACTING WITH A BAIT POLYPEPTIDE OF INTEREST: APPLICATION TO THE CONSTRUCTION OF MAPS OF INTERACTORS POLYPEPTIDES

This is a continuation of application Ser. No. 09/637,240, filed Aug. 14, 2000, now U.S. Pat. No. 6,531,284, which is a continuation of application Ser. No. 09/025,151, filed on Feb. 18, 1998, now U.S. Pat. No. 6,187,535, which are incorporated herein by reference.

The present invention is directed to a method for selecting a prey polypeptide that is able to interact with a bait polypeptide of interest, to a prey polynucleotide encoding the prey polypeptide as well as to the prey polypeptide itself. The invention also concerns plasmids used for performing the method of the invention as well as prokaryotic or eukaryotic recombinant host organisms containing such plasmids and also a collection of said recombinant host organisms consisting in a DNA library, such as a collection of recombinant haploid *Saccharomyces cerevisiae*. Finally, the invention is also directed to a technical medium containing the whole information concerning the interactions between metabolically related bait and prey polypeptides and/or polynucleotides coding for bait and prey polypeptides.

BACKGROUND OF THE INVENTION

Most biological processes involve specific protein-protein interactions. General methodologies to identify interacting proteins or to study these interactions have been extensively developed. Among them, the yeast two-hybrid system currently represents the most powerful in vivo approach to screen for polypeptides that could bind to a given target protein. Originally developed by Fields and coworkers [(Fields et al., 1989; Chien et al., 1991). Two U.S. Pat. No. 5,283,173 granted on Feb. 1, 1994 (Fields, S. & Song, O.) and U.S. Pat. No. 5,468,614 granted on Nov. 21, 1995 (Fields, S. & Song, O.) herein incorporated by reference], the two-hybrid system utilizes hybrid genes to detect protein-protein interactions by means of direct activation of a reporter-gene expression (Allen et al., 1995; Transy et al., 1995). In essence, the two putative protein partners are genetically fused to the DNA-binding domain of a transcription factor and to a transcriptional activation domain, respectively. A productive interaction between the two proteins of interest will bring the transcriptional activation domain in the proximity of the DNA-binding domain and will trigger directly the transcription of an adjacent reporter gene (usually lacZ or a nutritional marker) giving a screenable phenotype. The transcription can be activated through the use of two functional domains of a transcription factor: a domain that recognizes and binds to a specific site on the DNA and a domain that is necessary for activation, as reported by Keegan et al. (1986) and Ma et al. (1987).

Recently, Rossi et al. (1997) described a different approach, a mammalian "two-hybrid" system, which uses β-galactosidase complementation (Ullmann et al., 1968) to monitor protein-protein interactions in intact eukaryotic cells.

The number of genome sequences of prokaryotic as well as eukaryotic host organisms available is increasing exponentially and there is a great need for new tools directed to the functional and global study of these newly characterized complete or partial genomes. As an illustrative example, the genome of the yeast *Saccharomyces cerevisiae* is now completely sequenced (Goffeau et al., 1996). Despite the tremendous and successful genetic work in past years, 60% of yeast genes have no assigned function and half of those encode putative proteins without any homology with known proteins (Dujon, 1996). In yeast, genetic analyses, such as suppressor or synthetic lethal screens, have suggested many functional links between gene products, some of which have later been confirmed by biochemical means. All together, these approaches have led to a rather extensive knowledge of defined biochemical pathways. However, the integration of these pathways in the complexity of a living cell remains to be accomplished. To explore the integrative functions and find the molecular factors sustaining them, some authors have attempted to design new screens. However, these screens are usually very specific and cannot apply directly to many different cellular functions. In addition, few yeast genes are essential, leading to an additional difficulty for genetic screens. Other approaches developed by cellular biologists seek to precisely localize proteins within the cell. The assumption is that colocalization of factors is indicative of functional interactions. This approach has been very successful, despite the fact that it is usually very elaborate and is rarely considered practicable for a systematic approach (Burns et al., 1994).

Bartel et al. (1996) extended the approach of the typical two-hybrid system consisting in a known protein that forms a part of a DNA-binding domain hybrid, assayed against a library of all possible proteins present as transcriptional activation domain hybrids, using the genome of bacteriophage T7, such that a second library of all possible proteins fused to the DNA-binding domain to be analyzed. This genome-wide approach to the two-hybrid searches has identified 25 interactions among the proteins of T7.

However, the currently available two-hybrid methodology is not suitable for a large scale project without specific methodological improvements. Although the two-hybrid strategy has been a major tool in proving protein:protein interactions between factors known to be functionally related (Fields and Song, 1989), its use for exhaustive and reliable search for unknown partners of a given protein is more problematic. Thus, in most cases, the two-hybrid screen constitutes an initial screen in which many different interactions are found. Among the identified candidates, only some of them are favored due to their appealing sequence. Subsequent functional assays are required for establishing their possible biological significance. For these reasons, the two-hybrid methodology has been considered a difficult, if not misleading experimental approach for screening.

Finley et al. (1994) or Bendixen et al. (1994) have described two-hybrid systems including a step of mating yeast cell colonies by replica-plating diploids, that is to say by mating colonies of yeast cells. Finley et al. (1994) have, in a first step, selected specific inserts of a DNA library using, as selection criteria, the probability for a specific insert contained in the library to comprise a large coding region of an ORF or to contain a coding region associated with a specific biological function. For example, Finley et al. (1994) have made a collection of strains, each of which expressed a different bait (in fact two cyclin dependent kinases [Cdks], namely DmCdc2 and DmCdc2c), and mated them, by replica-plating, with test strains that contained different activation-tagged Cdis (Cyclin-dependent kinase interactors). Then, each of the selected baits was used as a bait in order to screen the prey Cdis of the DNA library. Examination of the resulting interaction matrices showed that each Cdi (preys) associates specifically with a distinct spectrum of Cdks (baits).

Despite the fact that these authors state that their results suggest a number of applications of their method to genetic characterization of larger sets of proteins, it must be pointed out that these screening experiments of prior art lead to the constitution of interactor polypeptide matrices restricted, as the numerous two-hybrid systems of prior art, by the initial choice of the potentially interesting polynucleotide inserts initially identified and/or initially selected in the DNA library.

Moreover, the replica-plating step that makes use of yeast cell colonies does not allow the mating of numerous different recombinant yeast cell colonies in a single culture dish, thus rendering very fastidious, or even materially impossible the study of potential interactions between a given bait polypeptide and a wide collection of prey polypeptides, such as a collection of prey polypeptides encoded by polynucleotides originating from the whole genome of an organism such as a bacterial, viral or yeast organism.

SUMMARY OF THE INVENTION

The aim of the present invention is to provide a new method for selecting a polynucleotide encoding a prey polypeptide in a two-hybrid screening system, said method making use of mating recombinant haploid yeast cells instead of recombinant yeast cell colonies, said method providing significant advantages over prior art.

Thus, the present invention provides a method for selecting a polynucleotide encoding a prey polypeptide, said prey polypeptide being able to interact with a bait polypeptide, comprising the steps of:

a) subjecting a bait polynucleotide encoding the bait polypeptide, to a two-hybrid screening method, wherein said two-hybrid screening method comprises a step of mating at least one first haploid recombinant yeast cell containing the prey polynucleotide to be assayed with a second haploid recombinant yeast cell containing the bait polynucleotide, provided that one haploid yeast cell among the first recombinant yeast cell or the second recombinant yeast cell also contains at least one detectable gene that is activated by a polypeptide including a transcriptional activation domain;

b) selecting the recombinant diploid yeast cell obtained at step a) for which the detectable gene has been expressed to a degree greater than expression in the absence of interaction between the bait polypeptide and the prey polypeptide;

c) optionally characterizing the prey polynucleotide contained in each diploid yeast cell selected at step b).

By a bait polynucleotide according to the present invention, it is intended a chimeric polynucleotide encoding a chimeric polypeptide comprising i) a DNA-binding domain that recognizes a binding site on a detectable gene that is contained in a host organism and ii) a polypeptide that is to be tested for interaction with at least one prey polypeptide.

By a prey polynucleotide according to the present invention, it is intended a chimeric polynucleotide encoding a chimeric polypeptide comprising i) a transcriptional activation domain and ii) a polypeptide that is to be tested for interaction with a bait polypeptide.

Among the numerous improvements brought by the method of the invention over the existing screening systems, said method:

i) allows, in a single step, the screening of far more prey polynucleotides with a given bait polynucleotide than the prior art systems because the mating is performed between haploid yeast cells and not between yeast cells and a yeast cell colony (or between yeast colonies);

ii) As a consequence of i), the method allows the whole screening of a DNA library without the need of a first step consisting of selecting the potentially interesting polynucleotide inserts contained therein and allows an objective analysis of the potential interactor polypeptides;

iii) because the mating step is performed between haploid recombinant yeast cells and not between recombinant yeast cells and a yeast cell colony, and thus because the mating step does not take into account the former differential growth properties of different recombinant yeast cell colonies, the method of the invention is far more exhaustive as well as reproducible than the conventional two-hybrid screening systems. Moreover, an efficient mating step of a short duration that is performed between individual recombinant haploid yeast cells have two other advantages, namely a) there is a high percentage of recombinant diploid yeast cells and not only several diploid recombinant yeast cells dispersed in a single colony and b) the short period of time (less than 5 hours) that is necessary for mating the two populations of haploid yeast cells is not sufficient for a significant growth of the haploid colonies which have not successfully undergone the mating step, nor the doubling of the recombinant diploid yeast cells before plating.

As another advantageous characteristic of the matin, step according to the two-hybrid screening method of the invention, the inventors have adjusted the experimental protocol in order to obtain up to a 50% increase in the efficiency of the mating procedure, this percentage being expressed as a ratio of diploid cells generated, and not as a ratio of recombinant colonies, such as expressed in prior art mating experiments.

The above-described characteristics of the two-hybrid screening method of the invention leads to a nearly perfect standardization of the diploid yeast cell population under testing. In other words, the whole characteristics of the DNA library used as starting material are perfectly reflected in the resulting recombinant diploid yeast cell population after mating. This is why the present two-hybrid screening method is of great reproducibility, from one screen to another and the interactions identified are thus of a high reliability.

In a specific embodiment of the method according to the invention, which is a further improvement over the prior art methods, the DNA library is presented as a ready-to-use biological material consisting in a collection of recombinant haploid yeast cells containing the whole inserts generated during the construction of the DNA library under the form of prey polynucleotides as defined above, said collection of yeast cells being frozen in multiple vials, each vial containing an identical biological material.

Consequently, one vial is thawed for each screening experiment and is directly used in the cell-to-cell mating step, in contrast to prior art methods, for example as described by Bendixen et al. (1994), that need a first step of separate culture, in suitable selective medium, both of the recombinant yeast cell clones containing the bait polynucleotide and of the recombinant yeast cell clones containing the chosen prey polynucleotides, then a second step of clone-to-clone replica-plating which is also performed in rich culture medium, before another step of clone-to-clone replica-plating for selecting the recombinant diploid yeast cells contained in the mated clones in a selection culture medium.

The above described characteristics of this specific embodiment of the screening method according to the invention ensures that said method is fast, exhaustive and reproducible, in contrast with the prior art techniques.

The two-hybrid screening method according to the invention is far more both quantitatively and qualitatively reproducible than the prior art methods that include a step of transformation of yeast cell with plasmidic DNA, for example, DNA originating from inserts contained in a DNA library prepared in *E. coli.*

Indeed, a primary DNA library in *E. coli* only allows a reduced number of successive screenings without the need of a further culture of the *E. coli* clones in order to make more starting DNA material available. In these circumstances, the further culture of the recombinant *E. coli* clones of the DNA library necessarily introduce discrepancies in terms of the representativity of the different inserts initially contained in the DNA library, as the different clones may have various growth rates.

In contrast, the method according to the invention allows in a single step the preparation of a high quantity of starting DNA material under the form of recombinant haploid yeast cells, said starting material being subsequently stored in a high number of identical vials, thus ensuring that each processing of the method use strictly identical starting material representing the whole DNA library initially prepared.

The great reproducibility and exhaustivity of the above-described method allows the one skilled in the art to reiterate said method using each of the prey polynucleotide selected at step b) as a bait in order to identify and characterize polynucleotides that are systematically selected as coding for interactor polypeptides of biological significance.

The successive reiterations of the screening allow the one skilled in the art to identify important interactions between polypeptides encoded by diverse polynucleotide inserts contained in the initial DNA library, which interactions are of statistical and biological significance. Three reiterations of steps a) to c) of the method according to the invention allow the one skilled in the art to determine which polynucleotide inserts of the initial DNA library are systematically selected for interaction with an initial bait polypeptide and/or another polynucleotide insert of the initial DNA library and thus which is statistically of great metabolical and/or physiological interest.

Consequently, a specific embodiment of the method according to the invention comprises repeating at least once steps a) to c) using, for performing each reiteration, at least one previously selected and/or characterized prey polynucleotide as the bait polynucleotide.

The number of repeats of steps a) to c) is no more than 10, preferably no more than 5 and in a most preferred embodiment the number of reiterations of steps a) to c) is 3.

In a preferred embodiment of the method of the invention in which steps a) to c) are reiterated, the bait polynucleotide used that corresponds to a selected prey belongs to the following group of polynucleotide consisting in:
a) a polynucleotide that is identical to said selected prey polynucleotide;
b) a polynucleotide containing the complete ORF including said selected prey polynucleotide;
c) a polynucleotide which is any polynucleotide fragment comprised in the complete ORF including said selected prey polynucleotide.

A polynucleotide fragment of a complete ORF may be obtained either by digestion with a restriction endonuclease, as described in Sambrook et al., or by digestion with an exonuclease such as Ball , or also by DNA synthesis, such as described by Sonveaux et al. (1986), Hsiung et al. (1980), Froehler et al. (1986), Alvarado-Urbina (1986), Crea et al. (1978) or also Urdea et al. (1983) or by PCR as described in the Examples.

Using, as the bait polynucleotide, a complete ORF corresponding to a given prey selected at a given round, for example first round, of the method of the invention, for performing the next round allows the one skilled in the art to select exhaustively all the potential polypeptides that are able to interact with the translation product of said complete ORF bait polynucleotide. Consequently, all the possible polypeptides interacting with any peptide domain of the polypeptide encoded by the complete ORF including the previously selected prey are identified.

Preferably, the first screening using the method according to the invention will comprise a limited number of screenings with a limited number of bait polynucleotides, usually with bait polynucleotides encoding for bait polypeptides already characterized for being involved in a given physiological and/or metabolic pathway, like, for example, pre-mRNA splicing.

When several, preferably three, reiterations of the method of the invention are performed and thus common bait and prey polypeptide are selected, a map of all the interactions between these polypeptides may be designed, that take into account of the known and/or suspected biological function of each of the polypeptide interactor molecules. Such an interactors map may help the one skilled in the art to decipher a whole metabolical and/or physiological pathway that is functionally active within the host organism from which the initial DNA library is derived, as it will be seen in the examples presented hereunder.

Another object of the present invention consists in a representative and exhaustive genomic DNA library of an prokaryotic or an eukaryotic host organism that is prepared according to the invention.

Preferably, the method of the invention is performed using, as the genomic DNA library starting material, inserts provided by the fragmentation of the genome of a host organism that does not contain, and/or contains a small number of, intronic sequences.

Preferably, such an exhaustive genomic DNA library is prepared from the genomic DNA of a host organism endowed with a compact genome, that is to say a genome containing at least 50% of coding sequences, more preferably at least 65% of coding sequences and most preferably 75% of coding sequences. Among such an host organism having a compact genome as defined herein above may be cited prokaryotic organisms like virus and bacteria and also eukaryotic organisms such as yeast.

A further object of the present invention consists in a representative and exhaustive genomic DNA library derived from *Saccharomyces cerevisiae*, designated as the FRYL library, which is used when performing the two-hybrid screening method of the invention.

The invention also concerns an improved recombinant plasmid used to express the prey polynucleotides to be selected according to the method of the invention, as well as a recombinant host organism containing said plasmid.

The invention is also directed to a collection of recombinant cell clones consisting in a collection of recombinant host organisms as described hereinabove.

The present invention concerns also a recombinant diploid yeast cell selected by the method of the invention.

Are also part of the invention a polynucleotide that has been selected according to the method of the invention, as well as a polypeptide which is encoded by such a polynucleotide.

The invention is further directed to a technical medium containing an interactors map representing at least a set of interaction events that have taken place between the polypeptides encoded by the polynucleotides selected by the method of the invention.

BRIEF DESCRIPTION OF THE DRAWINGS

FIG. 5. Interacting domains defined by ORF fragments selected in two-hybrid screens.

FIG. 6. The family of yeast Sm proteins: Yeast sequences are grouped in sub-families and aligned with the respective human homologues. Dashes indicate omitted residues for sake of space. Residues that define Sm1 and Sm2 motifs are indicated by vertical grey bars (Hermann et al., 1995). Common residues within a family are shown in reverse print.

DETAILED DESCRIPTION OF THE INVENTION

Figure 1:
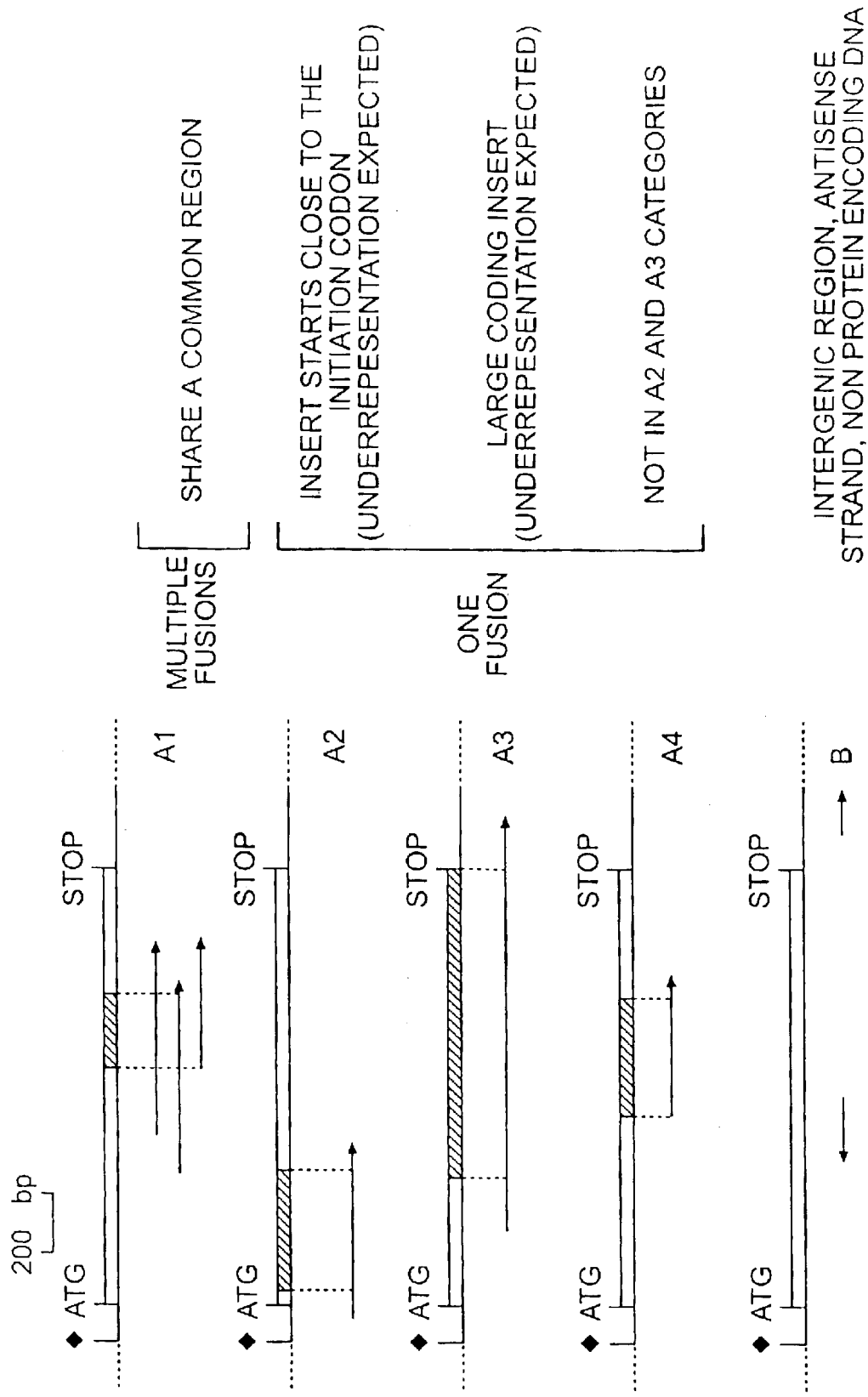
FIG. 1. Classification of preys selected in a two-hybrid screen of a yeast genomic library: A fragment of a yeast chromosome is represented with a potential in frame non sense codon (u) upstream of the initiation codon of a yeast ORF (open box). The putative interacting domain is shown (shaded box). Arrows indicate the position, the length and the orientation of selected inserts. The categories of preys are defined on the right (see text for details).

The inventors have developed new tools and procedures for the two-hybrid strategy that allows a highly selective screening of a complete genome, typically a compact genome such as the yeast genome, leading to a limited set of proteins potentially interacting with a given protein.

Thus, the present invention is directed to an improved two-hybrid screening method comprising steps a) to c) described hereinbefore, and, as a specific embodiment of said method, at least one reiteration of steps a) to c) using at least one initial prey polynucleotide as the bait polynucleotide.

In a preferred embodiment of the method according to the invention, the mating step between the two categories of recombinant haploid yeast cells, respectively containing a given bait polynucleotide or a prey polynucleotide included in a collection of prey polynucleotides, is performed on a porous filter, the mean diameter of the pores being such that said filter retains the yeast cells.

The filter may be used as a component of a filter holder in which a yeast cell mixture consisting in both a first population of haploid yeast cells containing the bait polynucleotide and a second population of haploid yeast cells which is a collection of yeast cells, each containing a different prey polynucleotide. In this specific embodiment of the method according to the invention, the filter holder is filled with a culture medium suspension containing the yeast cell mixture which is passed through the filter in order to collect the yeast cell mixture on said filter before placing the filter on a suitable culture dish previously coated with a desirable culture medium.

The filter may also be placed directly on the culture dish previously coated with the desirable culture medium. In this case, the yeast cell mixture is added onto the already placed filter, in a small volume of culture medium, after that the initial yeast cell mixture has been centrifuged and then harvested in said small volume of culture medium, before plating, optionally using glass beads, the resulting mixture on a suitable culture dish previously coated with a desirable culture medium.

The mating step designed by the present inventors may be performed in a short period of time such that practically no multiplication of recombinant yeast cells in presence occur. Typically, the mating step has a duration of less than five hours and is preferably performed in a period of time of four hours or even less, provided that this period of time is at least three hours.

As already mentioned, the two-hybrid method of the invention makes use of at least one detectable gene, the transcription of which is activated when a prey polypeptide and the bait polypeptide produced by the diploid recombinant yeast cells interact, due to the triggering of the transcription of said at least one detectable gene when both the DNA-binding domain contained in the bait polypeptide and the transcriptional activation domain contained in one prey polypeptide are in proximity, one to the other.

By at least one detectable gene according to the invention, it is intended from one to five, and preferably two or three detectable genes, the transcription of which is activated within the recombinant diploid yeast cell when the encoded bait and prey polynucleotides are able to interact.

Introducing a redundancy in the detectable signals produced when the bait polynucleotide and a particular prey polynucleotide interact allows the one skilled in the art to discard the eventual artefacts that correspond to background levels of transcription of one of the detectable genes used in a given situation and consequently avoid the selection of false positive interaction and then false interactor polypeptides or polynucleotides.

Preferably, the at least one detectable gene is contained by the first recombinant haploid yeast cell containing the bait polynucleotide.

The at least one detectable gene may be contained either in a plasmid of the recombinant diploid yeast cell or in its genome.

As an illustrative embodiment, the at least one detectable gene is located in the chromosome of one recombinant haploid yeast cell used according to the method of the invention, and preferably the yeast cell containing the bait polynucleotide.

As another illustrative embodiment, the at least one detectable gene is choosen among the group consisting in a nutritional gene or also a gene the expression of which is visualized by colorimetry, such as HIS3, LacZ or both LacZ and HIS3.

The DNA-binding domain of the bait polypeptide and the transcriptional activating domain of the prey polypeptide may be of different kinds. As an illustrative embodiment, these can be derived from LexA or also Gal4.

Moreover, the inventors have also modified a prior art plasmid, plasmid pAS2 (commercialized by Clontech) in order to improve the functional characteristics of the plasmid containing the bait polynucleotide by deleting two genes:

i) a first gene initially used as a selection marker, gene CYH2 coding for the cycloheximide resistance and which have been found by the inventors to be of significant toxicity for the recombinant host cells bearing it;

ii) a second gene, gene HA used for detecting the synthesis of the fusion polypeptides in western blotting experiments (using anti-HA antibodies), the presence of which has been found to cause a reduced selectivity.

Figure 7:
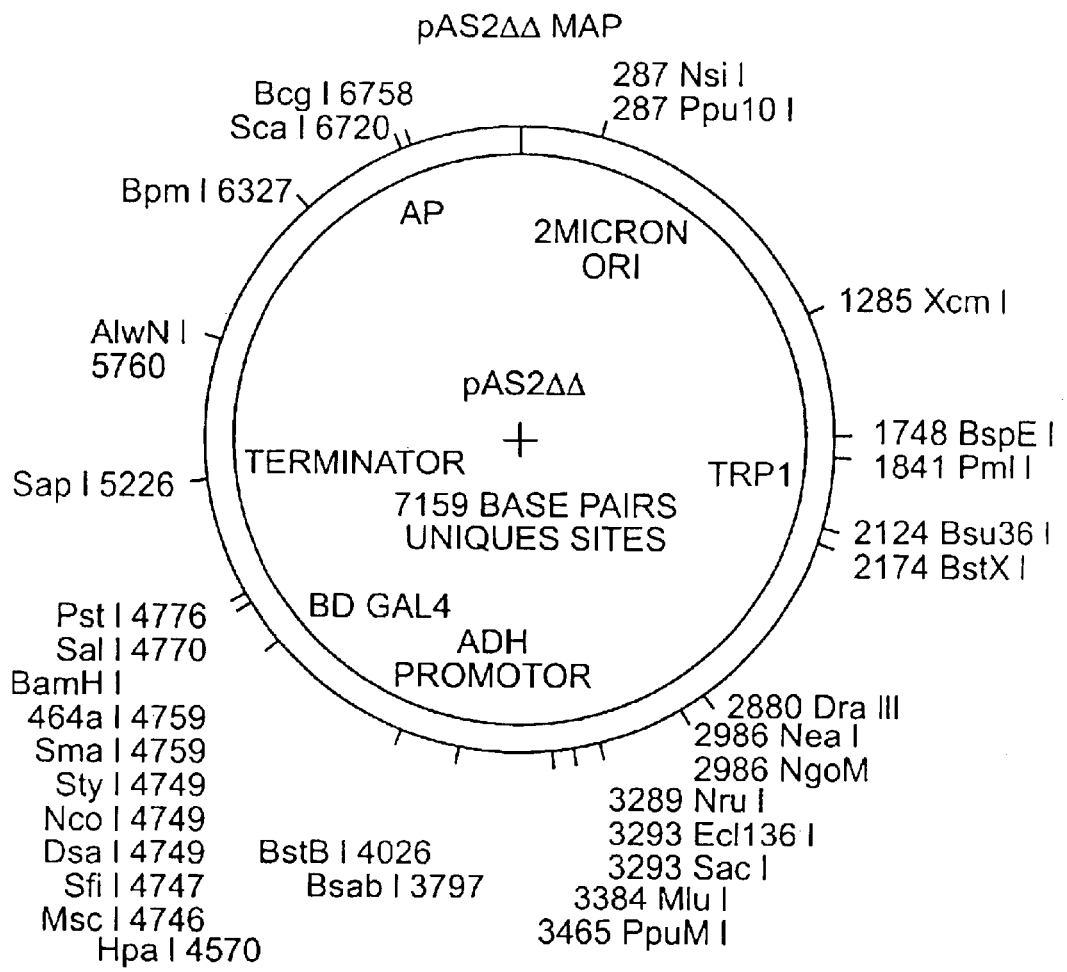
FIG. 7 Map of plasmid pAS2ΔΔ.

The resulting improved plasmid is plasmid pAS2ΔΔ (See FIG. 7) which is contained in the *E. coli* strain that has been deposited at the Collection Nationale de Cultures de Microorganismes (C.N.C.M.) on Feb., XX 1998 under the accession number I-XXXX. Plasmid pAS2ΔΔ is also part of the invention, as well as a recombinant organism of prokaryotic or eukaryotic origin containing said plasmid.

Figure 8:
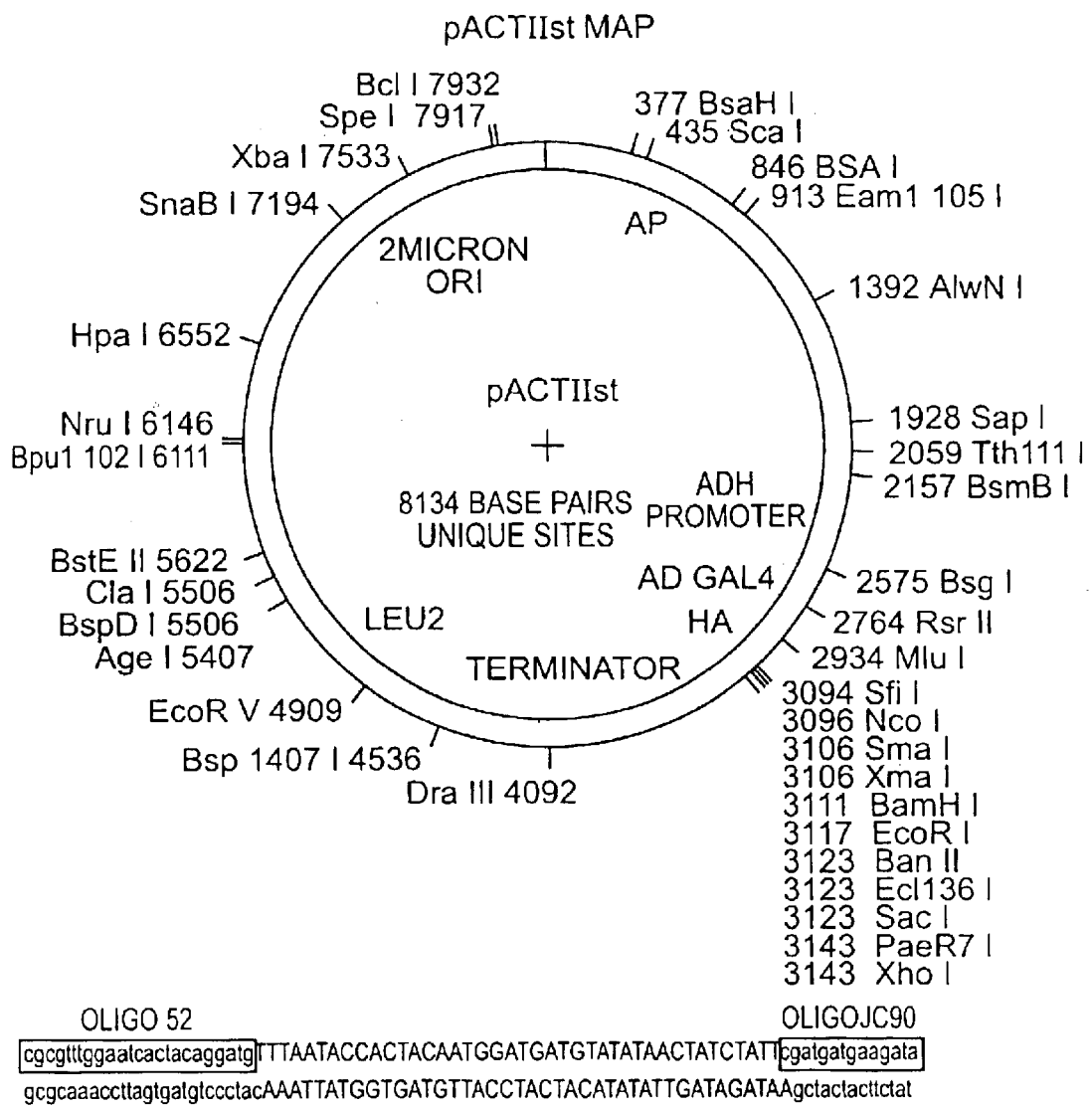
FIG. 8 Map of plasmid pACTIIst.

Is also part of the present invention the plasmid pACTIIst, the restriction map of which is presented in FIG. 8.

The invention also consists in a recombinant host organism containing the recombinant plasmid pACTIIst.

Is also part of the present invention a recombinant host organism containing the recombinant plasmid pAS2ΔΔ.

More specifically, the following recombinant haploid yeast cells are useful for performing the method according to the present invention:

Y187, (MATα Gal4ΔGal80Δ ade2-101 his3 leu2-3,112 trp1-901 ura3-52 URA3::GAL1$_{UAS}$-LacZ met⁻), CG1945 (MATa Gal4-542 Gal80-538 ade2-101 his3Δ200 leu2-3,-112 trp1-901 ura3-52 lys2-801 URA3::GAL4$_{17mers(X3)}$-CyC1$_{TATA}$-LacZ LYS2::GAL1$_{UAS}$-GAL1$_{TATA}$-HIS3 CYH$^R$), L40 (MATa ade2 trp1-901 leu2-3,112 lys2-801am his3Δ200 LYS2::(lexAop)$_4$-HIS3 URA3::(lexAop)$_8$-lacZ) (Hollenberg et al., 1995), and L40ΔGAL4 (MTAa ade2 trp1-901 leu2-3,112 lys2-801am his3Δ200 LYS2::(lexAop)$_4$-HIS3 URA3::(lexAop)$_8$-LacZ GAL4::KanMX2).

The L40ΔGAL4 yeast strain allows the one skilled in the art to select the recombinant diploid yeast cells obtained according to the method of the invention both with the HIS3 and the LacZ marker genes. The L40ΔGAL4 strain has been prepared according to the teachings of Wach et al. (1994, *Yeast*, 10:1793-1808).

Another object of the invention consists in a collection of recombinant cell clones from a host organism as described above, each different cell clone containing an inserted polynucleotide from a DNA library. Preferred recombinant host organisms are *E. coli* and yeast such as *Saccharomyces cerevisiae*.

An important feature of a further specific embodiment of the present invention resides in that the initial DNA library which provides the prey polynucleotides is strictly representative of the genome from which this DNA library is derived. By strictly representative, it is intended that the initial DNA library is composed of a number of polynucleotide inserts such that the DNA library i) covers the whole genome of interest and ii) the 5' end of the polynucleotide inserts begins every at least four bases interval of the genome of interest.

As a general feature of the method according to the present invention, the prey polynucleotides to be selected are provided by a DNA library. Such a DNA library may be prepared either from cDNA or also genomic DNA previously fragmented by restriction enzymes or sonication. For the use of restriction enzymes, the one skill in the art may refer to the works of Sambrook et al. (1989).

In one specific illustration, said DNA library is prepared using , as starting material, the mRNA or the genome of a prokaryotic host organism.

In another specific embodiment of such a DNA library, the starting material is the mRNA or the genome of a eukaryotic host organism.

A large and extremely representative genomic DNA library of a prokaryotic or eukaryotic organism having a compact genome is prepared by sonication as described in the Materials and Methods Section. One particular characteristic of such a DNA library is that all the potential interactors naturally encoded by the source organism are represented. Another characteristic of said DNA library consists in that no misrepresentation (i.e. over- or under-representation) of specific coding sequences are observed, as regards to the initial source genome.

Such a DNA library is prepared by sonication of the source genomic DNA, ensuring a random cleavage of the starting DNA material and thus a excellent representation of all the possible inserts, in contrast to techniques using restriction endonucleases.

In the protocol described, a great care have been taken in performing the steps of ligation of the DNA fragments that have been generated by the sonication step.

As an illustrative embodiment of such an exhaustive and representative DNA library used when performing the method according to the invention, the whole genome of *Saccharomyces cerevisiae* has been randomly fragmented by sonication and the resulting DNA fragments have been cloned in order to build a genomic DNA library. Said genomic DNA library contains 3.6×10$^6$ different clones derived from the *Saccharomyces cerevisiae* genome that comprises about 15×10$^6$ nucleotides. In other words, the *Saccharomyces cerevisiae* DNA library realized by the inventors contain polynucleotides beginning at every four bases interval of the initial genome.

As an illustration of the present invention, when applied to an exhaustive and representative genomic library of the yeast, and more specifically of *Saccharomyces cerevisiae*, several known proteins involved in the same pathway are used as baits in a first round of two-hybrid screens. Among the produced sets of preys, a new series of baits is in turn used for second round screens. Repeating this procedure several times have lead to the characterization of a network of interactions. Therefore, starting from known proteins, this approach not only makes connections between known proteins, but also identifies new factors and suggests novel functional links between pathways so far unrelated.

The spliceosome is an attractive entry point for such a project: i) the spliceosome formation is a dynamic process conserved through evolution that requires RNA-RNA interactions, protein-RNA interactions and protein-protein interactions; ii) it is formed of several snRNP particles, each of them containing many different proteins; iii) it builds on pre-mRNA through a stepwise formation of different complexes; iv) pre-mRNA splicing is a cellular process that is functionally linked to transcription and processing of primary transcripts, including export to the cytoplasm. Altogether, the implication of numerous different proteins suggests a pivotal role of the protein-protein interactions not only within each snRNP but also between particles. Moreover, the link between pre-mRNA splicing and other nuclear processes is most likely mediated by protein-protein interactions.

Spliceosome assembly involves the U1, U2, U4/U6 and U5 snRNPs and many additional splicing factors that were characterized through genetic screens and in vitro biochemical analyses (Beggs, 1995). Sequence analyses indicate that most of the yeast factors have homologues in human cells (KrŠmer, 1996). Out of several dozen yeast splicing factors, we chose some which are implicated in early steps of spliceosome formation.

A new yeast genomic library has been constructed and improved the two-hybrid procedure in such a way that for each bait, the complete screening of the genome produced a very limited set of candidates. Five different categories of candidates have been defined. Among the candidates, several were chosen for subsequent two-hybrid screens, and a novel prey was again used as bait in a third round of screening. On the whole, the fifteen screens led to the characterization of new interactions between known splicing factors, to the identification of new yeast splicing factors homologous to already known mammalian factors and to the finding of unexpected interactions that open novel opportunities for functional analyses.

As already mentioned hereinbefore, the inventors have constructed a novel and improved genomic DNA library from *Saccharomyces cerevisiae* containing $5 \times 10^6$ independent cell clones that have been pooled to constitute the "FRYL library." More than 70% of the clones tested contained an insert the nucleotide length of which is in the range from 200 to 1400 nucleotides with an average length of 700 bases.

The characteristics of the FRYL library allows the one skilled in the art to design DNA constructions for use in the method according to the invention leading to an in frame fusion between the Gal4 activation domain and a yeast ORF once every 24 nucleotides.

When assaying the fusions created using the polynucleotide inserts of the FRYL library as starting material, and using, on another hand, bait polynucleotides encoding already known nuclear proteins implicated in the pre-mRNA splicing pathway (listed in Table 1) several polynucleotide preys originating from the FRYL library were selected which have been determined to be of great biological significance, since among the selected prey polynucleotides a significant number of those are involved in the pre-mRNA splicing pathway, including still uncharacterized ORFs (Ylr116w and Yor319w) sharing strong homology with human protein counterparts such as SAP49 and SF1, one of the human SF3b component (Wells et al., 1996; Arning et al., 1996).

The present invention thus also includes the FRYL library contained in the collection of recombinant *E. coil* strain MR32 cells that have been deposited at the Collection Nationale de Culture de Microorganismes (C.N.C.M.), *Institut Pasteur*, 28 rue du Dr. Roux, 75724, Paris, Cedex 15, France, on Dec. 21, 1995, under the accession number I-1651.

The present invention also concerns a recombinant diploid yeast cell selected by the present two-hybrid method.

Another object of the invention consists in a polynucleotide that has been selected with the method of the invention, as well as a polypeptide that is encoded, at least in part, by said polynucleotide.

The invention is also directed to technical means that are needed to perform the present two-hybrid screening method.

An illustration of such technical means consists in a kit for selecting at least one polypeptide of interest belonging to *Saccharomyces cerevisiae*, wherein said kit comprises
  a) at least one complete collection of yeast cell clones containing the whole polynucleotide inserts representative of the genome from a prokaryotic or eukaryotic organism having a compact genome;
  b) optionally, the plasmid pAS2ΔΔ;
  c) optionally, the plasmid pACTIIst;
  d) optionally, a haploid yeast cell to be transformed with a plasmid containing a bait polynucleotide of interest;
  e) optionally, the reagents necessary to visualize the expression of at least one detectable gene, such as X-Gal.

The most preferred embodiment of a genomic DNA library usable as a starting material in a kit according to the invention is the FRYL library described above, which may be initially contained in plasmids that have been transformed in *E. coli* (CNCM I-1651), or which may be directly contained in a suitable recombinant haploid yeast cell (FRYL libraries to be deposited).

Figure 9A:
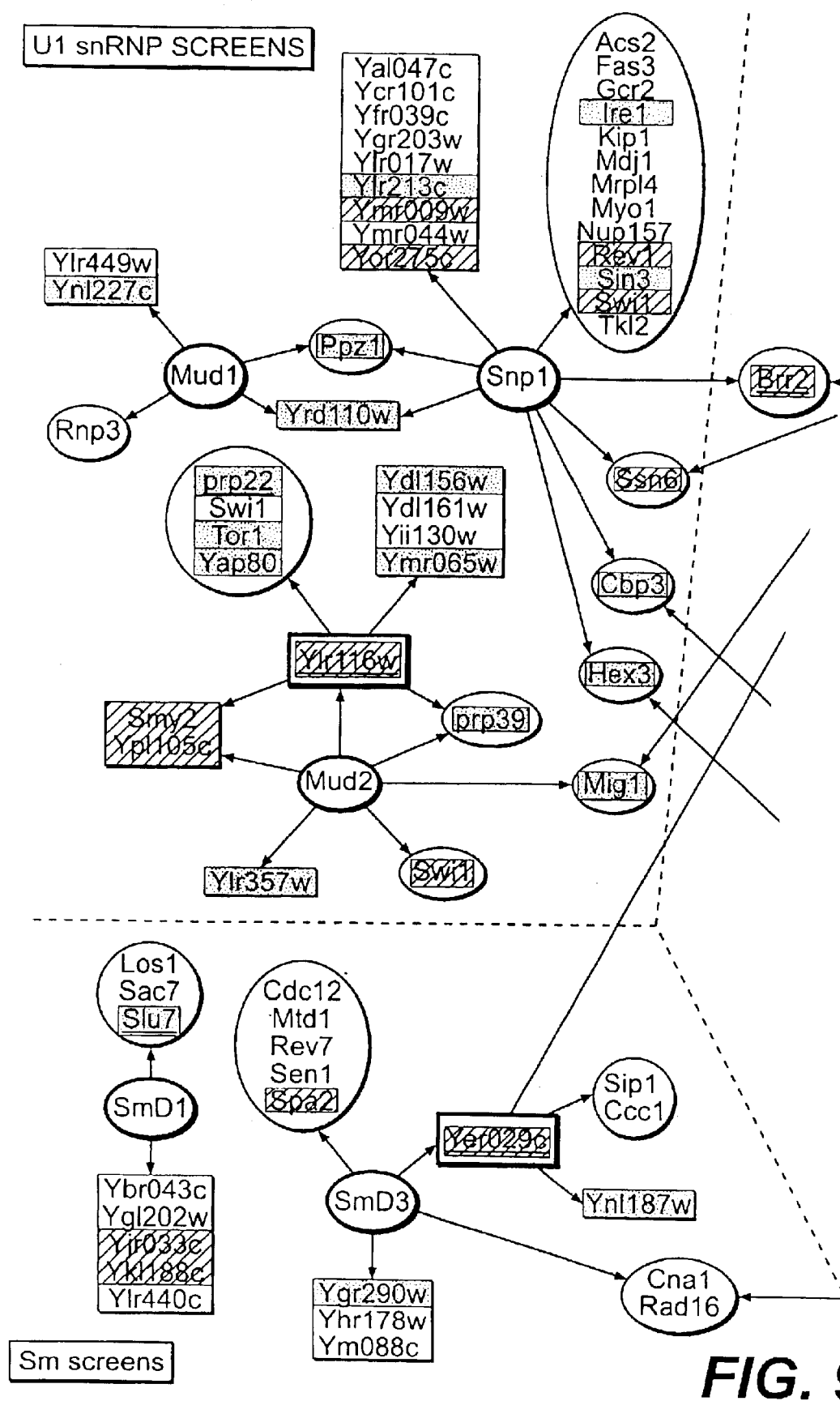
FIG. 9 A yeast protein interaction map: Labels are given in the insert. Baits are boxed in black and white. All ORF preys found in screens are shown and linked to their bait by an arrow. Preys of the A1 category are boxed in black, and those of the A2 or A3 categories are boxed in grey. The unknown ORFs (square boxes) are named following the official nomenclature and the names of the known genes (rounded boxes) are those chosen by the Yeast Proteome Database. Smy2p and Ypl105c are two highly homologous proteins. Splicing factors selected as preys are underlined. Preys found in several screens are separately boxed except Swi1p for which interactions are most probably non specific.
Figure 9B:
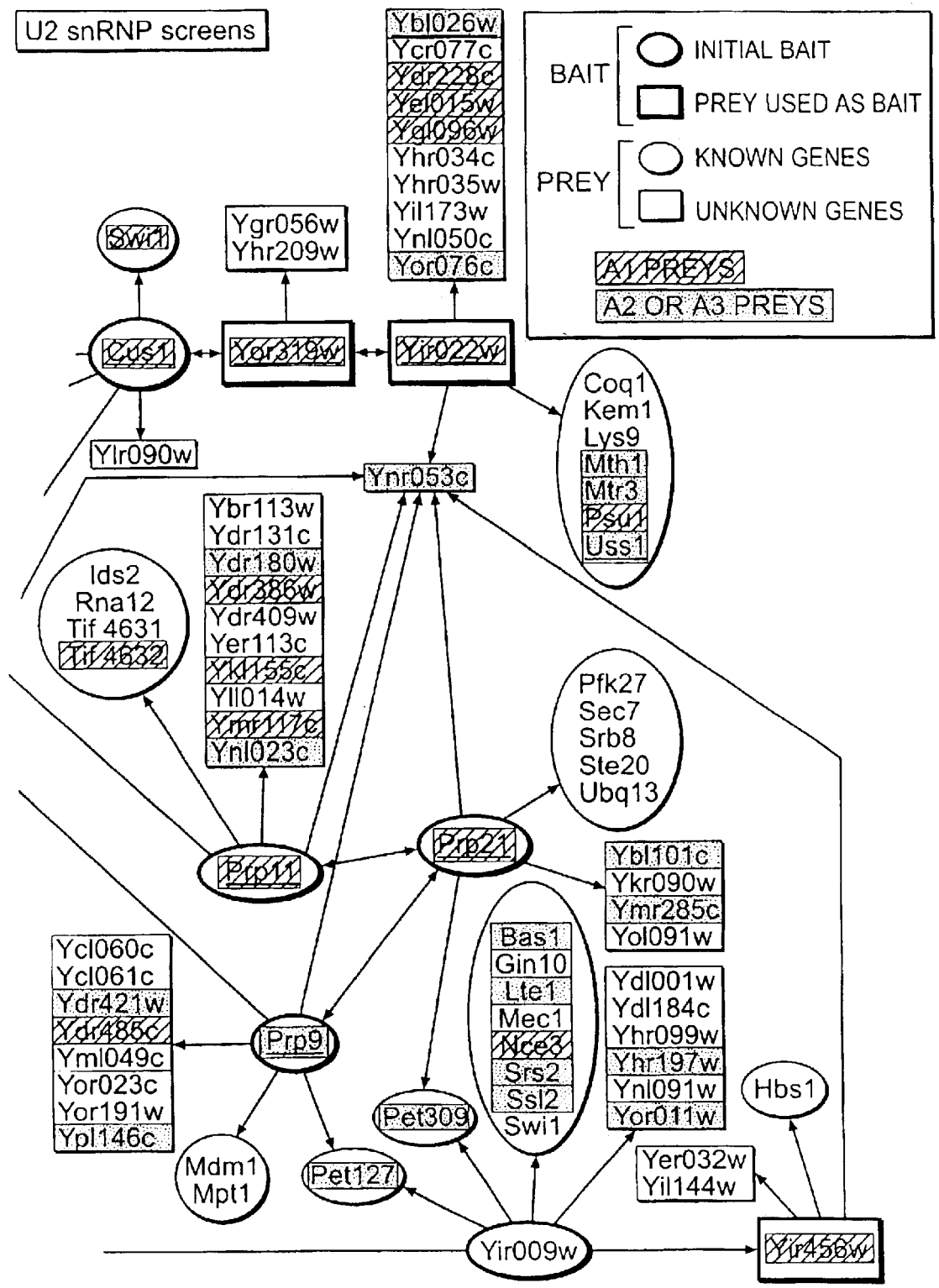

As it is described in details in Example 4, a second and third reiteration of the method according to the invention, using the previously selected prey polynucleotides as the bait polynucleotides that are again tested against the FRYL DNA library, have allowed the inventors to design a map of the identified interactions (See FIG. 9). More precisely, as it can be seen in FIG. 9, 170 preys have been selected in the 15 screens performed and correspond to 145 ORFs, implicated in different cellular pathways. Nine Orfs are involved in pre-mRNA splicing, six in other RNA metabolisms, ten are involved in transcription and four are protein kinases and phosphatases.

Since the screening method of the invention is exhaustive and reproducible, the selected prey polynucleotides may be classified in different categories, depending of their degree of occurrence in the positively selected diploid yeast cell clones or also of their size location or their location in a given ORF.

Consequently, is also part of the invention a particular embodiment of the present two-hybrid method, wherein the prey polynucleotide selected at step b) is classified within one of the following prey polynucleotide classes:
  a) a polynucleotide contained in an intergenic region or on the reverse orientation of an ORF contained in the genome of the organism from which the initial DNA library has been prepared (B).

b) a polynucleotide selected several times and contained in different clones of the initial DNA library (A1);

c) a polynucleotide selected only once and having a 5' end of the coding strand starting close to an initiation codon of an ORF contained in the genome of the organism from which the initial DNA library has been prepared (A-2);

d) a polynucleotide selected only once and having a nucleotide length of at least 1000 bases (A3);

e) a polynucleotide selected only once and having characteristics different from the polynucleotides of the a), b), c) and d) classes (A4).

For the purpose of the present invention, the expression "coding strand starting close to an initiation codon of an ORF" means that the initiation codon of a given yeast ORF is at a nucleotide distance less than 150–200 bases from the in-frame stop codon located upstream said ORF.

Among the polynucleotides inserts selected by the method according to the invention, several of them include inserts with out of frame fusions. The hypothesis is that the correct in-frame synthesis occurs through the production of frame-shifted polypeptides.

Since the two-hybrid screening method of the invention allows the one skilled in the art to design a statistically and biologically significant map of the interactor polypeptides (baits and preys) that have been selected, another object of the invention is a technical medium containing the whole pertinent interactions between metabolically related bait and prey polypeptides and/or polynucleotides coding for such bait and prey polypeptides.

As a specific embodiment of such a technical medium defined herein above, it may be cited a computer useable medium containing computer readable data related to the interactions between at least one bait polypeptide and at least one prey polypeptide encoded at least in part by a prey polynucleotide that has been selected with the two-hybrid screening method of the invention.

The present invention will be fully illustrated by the Materials and Methods protocols and by the Examples described below, although the scope of the invention cannot in anyway be limited to these specific embodiments.

Materials and Methods

A: The Mating Experiment

The mating procedure allows a direct selection on selective plates because the two fusion proteins are already produced in the parental cells. No replica plating is required. We routinely obtain at least 20% mating efficiency and regularly 50% mating efficiency.

Usually, the Y187 strain is transformed either with the FRYL yeast genomic library (see Part J for the characteristics of the yeast genomic FRYL library). Independently, bait plasmids are introduced in the CG1945 strain. The Y187 strain contains a sensitive LacZ reporter gene whereas the CG1945 strain has a non-leaky HIS3 reporter gene that enables the selection of positive diploids in the absence of 3-aminotriazol (3-AT).

Alternatively, bait plasmids can be introduced into the L40 strain. This plasmid derived from pBMT116 plasmid. It encodes for LexA fusion protein that can be assayed in a two hybrid system in the L40 strain containing His3 and LacZ reporter genes downstream LexA binding sites. The same Gal4-derived libraries could be used. However, the L40 strain is not deleted for the GAL4 gene and although glucose repression occurs, a residual activation of this gene in the diploid cells promotes the transcription of the parental Y187 strain's LacZ reporter gene. Thus, in a L40×Y187 diploid cell, selection is made only on the HIS3 reporter gene.

This protocol is written for the use of the FRYL yeast genomic library cloned into the Y187 strain. Any other genomic or cDNA library might be used with minor adaptations to take into account their complexity and the cell density of the frozen cells.

Strains

CG1945 (MATa Gal4-542 Gal80-538 ade2-101 His3-200 Leu2-3,-112 Trp1-901 Ura3-52 Lys2-801 URA3:: GAL4 17mers (X3)-CyC1TATA-LacZ LYS2::GAL1UAS-GAL1TATA-HIS3 CYH$^R$) transformed with the pAS2ΔΔ bait plasmid (see FIG. 7 for plasmid map)

Y187 (MATα Gal4Δ Gal80Δ ade2-101 His3 Leu2-3,-112 Trp1-901 Ura3-52 URA3::UASGAL1-LacZ Met$^-$) transformed with the FRYL yeast genomic DNA library (see Part L).

Day 1 Preculture

Materials 100 ml flask with 20 ml -W medium

Experiment

Preculture of CG1945 cells carrying the bait plasmid in 20 ml -W medium

Grow at 30° C., vigorous agitation.

Day 2 Culture

Materials 1 liter flask with 150 ml -W medium

Experiment at 6 pm

Estimate $OD_{600}$ of the -W preculture of CG1945 cells carrying the bait plasmid. Measure $OD_{600}$ of 4 to 10 fold dilution depending of the preculture. The OD must lie between 0.1 and 0.5 in order to correspond to a linear measurement (1 OD=$10^7$ CG1945 cells using our spectrophotometer).

Inoculate 150 ml -W at $OD_{600}$ 0.006/ml (may depend on local growth conditions; to be tested with various dilutions).

Grow o.n. at 30° C., vigorous agitation.

Day 3 Mating

Materials all the material must be sterile medium and plates

15 YPglu+Tetracyclin (Tet) 6 mg/ml plates a 50 ml tube with about 50 ml YPglu+Tet (6 mg/l).

a 50 ml tube with 35 ml -LWH 100 ml flask with 20 ml of YPglu

75—LWH+Tet (6 mg/ml) plates

2—L plates

2—W plates

2—LW plates

Materials

Swinnex 47 filter holder (ref: millipore SX00 047 00)

filters 0.22 μ 45 mm (ref: millipore GSWP 047 00)

10 ml syringe 9 cm plates forceps multipipettor and 10 ml sterile tips glass beads 3 mm 50 ml tubes large beaker Experiment

A.M.

Rinse forceps with water and ethanol; flame it and place it inside a sterile 9 cm plate. Using the syringe, soak up 1 ml of YPglu and keep it also inside a sterile 9 cm plate. Mark the YPglu+Tet plates with bait name.

Prepare Filter holder: open it up; (place parts inside a 9 cm plate) check placing of rubber rings; wet the filter-part with YPglu (from the syringe) and place a 47 mm filter on top, in the middle. Let the filter soak up the liquid and screw the upper part of the filter unit tightly on the lower half. Rinse filter with about 10 ml YPglu applied using the syringe attached to the opening at the top of the filter holder. Collect the liquid in the 500 ml beaker. Press the plunger to get an even distribution of the liquid over the filter. Check that the filter unit doesn't leak. If it does, don't panic, take off the pressure, open the unit, replace the filter and/or the rings and screw it maybe more tightly.

If the filter unit is contaminated take a new one and start again (This can also happen during the collection of diploid cells as described below as you replace the filter every time. Only when you take a new filter holder you have to do the pre-wetting and to rinse with 10 ml of YPglu).

Measure $OD_{600}$ of the -W culture of CG1945 cells carrying the bait plasmid. It should be around 1; definitely not higher than 1.5.

For the mating you must use twice as many bait cells as library cells. A vial of the Y187/FRYL yeast genomic DNA library contains $4.10^8$ viable cells.

Estimate the amount of bait culture (in ml) that makes up 80 $OD_{600}$ units for the mating with the yeast library (1 $OD=10^7$ CG1945 cells).

Thaw a vial containing the Y187/library slowly on ice.

Add the contents of the vial to 20 ml YPglu using a sterile plugged 1 ml pipet; rinse the vial with culture liquid.

Let those cells recover at 30° C., under gentle agitation for 10 minutes. Set your timer.

Mating

Put 80 $OD_{600}$ units of bait culture into a 250 ml flask. (Do not leave the CG1945 cells without agitation because of the aggregation of the cells)

Add the Y187/library culture to the bait culture.

Mix the library/bait cells by hand.

Collect 1/15 volume of mixed library/bait culture on one filter by pressing it through the Swinnex filter holder (15 independent mating experiments will be done). Rinse the filter with 4 ml fresh YPglu and about 10 ml air to dry it. Take off the syringe (under-pressure might cause a suck back; try to prevent it). Repeat the pressure with 10 ml air until no medium goes through the swinnex. Open the filter unit carefully so that any remaining fluid stays on top of the filter. Using the forceps, take off the filter and place it cells-up on top of an YPglu+Tet plate.

Repeat this another 14 times until all the cells are collected on filters. Before every sampling shake the culture to counteract the flocculation and to homogenize the cell density.

Incubate plates cells-up at 30° C. for 4 h 30 mn.

P.M.

Collection of Mated Cells

Mark the -L, -W, -LW and -LWH+Tet plates with date and bait-name. Add 5 to 7 sterile glass beads to every plate.

Wash and flame forceps (before placing them inside a sterile 9 cm plate).

Place the base of a 9 cm plate against the base of a Bunsen burner. Place a filter, with mated cells up, inside the base. Rinse the cells from the filter with 1 ml of -LWH using a pipetman. Reapply the cell-slurry a couple of times until all cells are washed off. Pipet the cell-slurry into the collection tube. (The cells are clearly visible as a reddish layer and come off as sheets in the beginning). Wash and rerinse the filter with another ml -LWH and pipet this into the collection tube. Discard filter with original YPglu+Tet plate.

Repeat this with all the filters. You will end up with about 30 ml of cell-suspension. Take note of the actual volume.

Plate the controls

Shake cell-suspension and make a 1:1000 dilution by three 10 fold dilution steps: (50 µl mix to 450 µl of fresh -LWH medium, shake well). Spread 50 µl of the 1000 fold dilution on -L, -W and -LW plates. Incubate cells down at 30° C. for two days.

Plate the Screen

Take multipipettor and sterile 10 ml tips.

Shake cell suspension and distribute cells in 400 µl samples over the 75 -LWH+Tet plates with glass beads. Spread cells by shaking the plates. Incubate plates cells down at 30° C. for three days.

This can be done only if one knows the behavior of the bait (e.g. it does not require addition of 3-AT in the plates). Otherwise, for an unknown bait, the optimal conditions must first be determined by plating samples onto -LWH plates without and with 3-AT at various concentrations (ranging from 1 to 50 mM).

The cell mixture can be stored at 4° C. and plated 3 days after the mating.

Day 3 Mating (Alternative Protocol)

Materials all the material must be sterile

Medium and Plates

5 YPglu+Tetracyclin (Tet) 6 mg/ml plates a 50 ml tube with 30 ml -LWH 100 ml flask with 20 ml of YPglu 75—LWH+Tet (6 mg/ml) plates 2—L plates 2—W plates 2—LW plates Materials 5 Hybond C-extra filters (Amersham, RPN 82 E)

9 cm plates forceps multipipettor and 10 ml sterile tips glass beads 3 mm 50 ml tubes Experiment

A.M.

Rinse forceps with water and ethanol; flame it and place it inside a sterile 9 cm plate. Mark the YPglu+Tet plates with bait name. Using the forceps, place a Amersham filter on top of an YPglu+Tet plate. Add 5 to 7 sterile glass beads to every plate. Prepare 5 plates with filter and glass bead.

Measure $OD_{600}$ of the -W culture of CG1945 cells carrying the bait plasmid. It should be around 1; definitely not higher than 1.5.

For the mating you must use twice as many bait cells as library cells. A vial of the Y187/FRYL yeast genomic DNA library contains $4.10^8$ viable cells. To get a good mating efficiency you must collected the cells at $4.5.10^6$ cells per $cm^2$ of filter.

Estimate the amount of bait culture (in ml) that makes up 80 $OD_{600}$ units for the mating with the yeast library (1 $OD=10^7$ CG1945 cells).

Thaw a vial containing the Y187/library slowly on ice.

Add the contents of the vial to 20 ml YPglu using a sterile plugged 1 ml pipet; rinse the vial with culture liquid.

Let those cells recover at 30° C., under gentle agitation for 10 minutes. Set your timer.

Mating

Put 80 $OD_{600}$ units of bait culture into a 250 ml flask. (Do not leave the CG1945 cells without agitation because of the aggregation of the cells).

Add the Y187/library culture to the bait culture. Mix the library/bait cells by hand. Transfer the mixture of diploids into 50 ml sterile tubes. Centrifuge the cells at 5000 g (4000 rpm) for 3 min.

Discard the Supernatant
Resuspend the pellet with 2 ml of YPGlu medium.
Distribute cells in 400 µl samples over the filter on YPGlu plates with glass beads. Spread cells by shaking the plates.
Incubate plates cells-up at 30° C. for 4 h 30 mn.
P.M.
Collection of Mated Cells
Mark the -L, -W, -LW and -LWH÷Tet plates with date and bait-name. Add 5 to 7 sterile glass beads to every plate.
Wash and flame forceps (before placing them inside a sterile 9 cm plate).
Place the base of a 9 cm plate against the base of a bunsen burner. Place a filter, with mated cells up, inside the base. Rinse the cells from the filter with 4 ml of -LWH using a pipetman. Reapply the cell-slurry a couple of times until all cells are washed off. Pipet the cell-slurry into the collection tube. (The cells are clearly visible as a reddish layer and come off as sheets in the beginning). Wash and rerinse the filter with 2 other ml -LWH and pipet this into the collection tube.
Discard Filter with Original YPglu+Tet Plate
Repeat this with all the filters. You will end up with about 30 ml of cell-suspension. Take note of the actual volume.
Day 5 Estimation of Diploid Number
Late in the afternoon: check controls of mating as well as some selective -LWH plates. About a hundred diploid colonies should be visible on -LW plates. Multiplying this number by 20 (50 µl sample), 1000 (dilution factor) and 30 (volume in ml of the diploids mixture) gives the amount of diploids (i.e. $60.10^6$ when you counted 100 on the -LW plate: 100×20×30×1000).
Count colonies on control plates. Estimate the mating efficiency by dividing the number of colonies on -LW plate by the number on the -L plate and multiply by 100.
Colonies should become visible on -LWH+Tet plates.
B: X-gal-Overlay Assay
Introduction
X-Gal-overlay assay is performed directly on the selective medium plates after scoring the number of His⁻ colonies. This procedure is less sensitive than the filter assay (Protocol C) but it is less time consuming and has the advantage of a better recovery of cells since it does not require freezing the cells in liquid nitrogen.
Materials
Work under the hood. Dimethylformamide (DMF) is toxic. Set up a waterbath. The water temperature should be 50° C.
Stock solutions:
−0.5 M $Na_2HPO_4$ pH7.5 (71 g $Na_2HPO_4$ per 1 liter+4 ml orthophosphoric acid). Distributed per 250 ml and stored at $50_iC$ (neither filtrated nor autoclaved).
−1.2% Bacto-agar distributed per 210 ml (2.52 g/210 ml). Autoclaved and stored at 50° C. (Alternatively, phosphate and agar solutions are kept at room temperature and the solutions are mixed just before use after melting the agar in a microwave oven)
−2% X-Gal in DMF and stored at −20° C.
Overlay Mixture:
0.25 M $Na_2HPO_4$ pH 7.5
0.5% agar
0.1% SDS
7% DMF (LABOSI ref DO675)
0.04% X-Gal (ICN ref 150001)
For every plate you need 10 ml overlay mixture:
5 ml 0.5M phosphate buffer pH 7.5
4.2 ml 1.2% agar
200 µl 2% (w/v) X-Gal in DMF
100 µl 10% SDS
500 µl DMF
-LWH plates
Sterile toothpicks
Experiment
Prepare the amount of overlay-mix you need. 500 ml maximum for one batch in order to keep the conditions similar (DMF will evaporate) and to prevent the mix settling too long in the bottle.
Mix 250 ml 0.5 M phosphate buffer pH 7.5+210 ml 1.2% agar+5 ml 10% SDS. Go under the hood and add 25 ml DMF and 10 ml 2% X-Gal.
Don't add X-gal solution unless you will use it immediately. Temperature of the mix should be between 50° C. and 45° C. Higher temperatures might affect the cells; lower temperature impairs handling.
With pipetpump and sterile 25 ml pipet divide the overlay-mix over the plates in portions of 10 ml. Let the mix flow out gradually where there are no colonies growing. Too fast a flow or directly hitting a colony will cause smearing of the yeast cells. Too slow a flow will cause settling of the mix before it has spread equally over the plate.
Work through the whole batch of plates laid out. Collect them when the top layer is settled (keep the plates horizontal; don't tip them; the whole overlay layer might move, causing smearing of the colonies). Check whether all colonies are covered by the overlay. If not, apply some mix on the 'uncovered' spots.
Incubate plates cells/overlay-up at 30° C. Note the time.
Check for blue colonies after 30 min, 1 h, 2 h, 4 h and 6 h incubation time. Mark positives with a felt-tip pen (a different color/marking-style for each check at the different incubation time).
After 30' and 1 hour do a quick check for blue colonies. Check very superficially. Do more careful checking after 2, 4 and 6 hours.
During checking, take the plates to the hood and check the color against a black background. Don't inhale the DMF, keep your head out of the hood. At this moment it is not essential whether you are able to pick all blue colonies (some will be pale).
Number the positives (If you want you can sample them in classes, distinguishing them according to colony-size and intensity of blue-color).
Take some fresh -LWH plates (it is important to maintain the selection for the interaction on LWH plates) and divide into 4 sections. Number them according to the number of positives found. Mark them with date and bait-name.
Streak the positive colonies after 6 h incubation time. Put the rest back at 30° C.
To streak cells from a single positive colony take a sterile toothpick through the agar-overlay into the colony and collect some cells. Streak the cells into one line. Take a fresh toothpick and restreak cells from the first line into a second one. Take a third toothpick and streak cells from the second into a third line and, after turning the toothpick, into a fourth line.
Next day, check plates for positives. Streak newly found positives. It is important not to wait too long in doing this as the components in the overlay-mix are not very good for the yeast cells (After 24 h incubation time the cells might be dead).
It takes about two days for colonies to grow.
There are five items to keep in mind:
1) What counts as a 'real' positive (=blue color) can differ from one screen to another. It might be related to the nature of the bait fusion, and also to its expression level.

2) Another factor is how fast the yeast colonies are permeabilized. Therefore you will see blue colonies coming up after an hour whereas for other colonies, it takes six hours. The intensity of the blue color can also range from deep dark to almost grey-light blue. Sometimes you see a blue halo around the colonies or the color is only restricted to the colony or its center. Always compare the color of putative positives with that of colonies on the same plate or on plates from the same screen.

3) Because of these kind of differences keep track of the time at which positives are found, size of colony and intensity of blue-color.

4) In the overlay method the blue-color develops with time. Compare the blue color of the positive colonies at a later time (i.e. after 24 h) than when you found/streaked them. Strong positives will turn bluer than weaker ones. Colonies that turned blue at a later time-point than others might have developed a more intense blue color than the 'earlier' ones.

5) Recovery of small colonies can be difficult, especially when streaking after 24 h incubation.

C: Filter Lift X-Gal Assay
Introduction

The filter lift assay is a fast and sensitive method to check whether the reisolated colonies are positive and homogeneous.

Materials
Plates with healthy, well-grown yeast colonies
Hybond C-extra filters (Amersham, RPN 82 E)
incubation plastic boxes
Whatman 3 MM paper
Millipore forceps
Saran wrap
Liquid Nitrogen
sterile toothpicks
-LWH plates
2% (w/v) X-gal solution in Dimethylformamide (DMF)
1M $Na_2CO_3$
Z-buffer with β-mercaptoethanol (Z-βOH):
100 mM $Na_2HPO_4$ pH7.5
10 mM KCl
1 mM $MgSO_4$
add 1.8 ml β-mercaptoethanol per 500 ml Z buffer (50 mM) just before use (if added in advance keep solution at 4° C.).
To 20 ml Z-βOH buffer add 400 µl 2% X-gal solution.

Experiment

Take a sheet of Whatman paper upon which you can work.
Cut a sheet of Whatman that fits exactly into the bottom of the incubation box.
Prepare just enough Z buffer-βOH/Xgal mix for wetting the paper: For one incubation box (about 300 cm² of paper) you'll need about 20 ml Z-βOH/Xgal mix.
Pour the Z-βOH/Xgal mix over the paper. Start in the middle and tilt the box so that the paper is uniformly wetted. Get rid of any bubbles. (Try to lift the wet paper with forceps at one of the corners to let the bubbles escape; be careful the paper may tear). Pour off excess Z-βOH/Xgal mix and keep as back-up. Place the lid on the box.
Take a Hybond C-Extra filter (or enough to cover those plate-sectors where yeast colonies have formed), remove protecting papers. Take a ball-point and mark the filter with a letter/number and a line.
Mark the plates with a line and numbers corresponding to the filters.
Lift the marked filter, with the mark at the underside (i.e. towards the yeast cells), using the forceps (or by hand with gloves) and the lid of the yeast plate.
Position the filter above the yeast plate so that the lines on the plate and the filter are aligned.
Gently let the filter descend upon the yeast cells (i.e. not smearing the colonies). Tap the plate in order to enhance the wetting of the filter.
Close the plate with the lid and, in the case you have to do a lot, apply a filter to the next plate.
When the filter is uniformly soaked or when all plates are done, lift the (first) filter gently from the plate using the forceps. Directly hang the filter in liquid nitrogen without releasing your grip on the forceps. Count to five, take the filter out of the nitrogen and let thaw cells-up on your paper work-sheet. (Continue with the next filter). Repeat freezing/thawing step a second time.
When the filters have thawed, transfer them to the incubation box (containing the Z-§OH/Xgal pre-wetted Whatman filter). Lay filters carefully cells-up and without trapping air bubbles. Close the box and seal the lid with parafilm. Incubate at 30° C.
Prepare a stop-paper and a wash-paper:
Stop-paper: Take a slightly smaller piece of Whatman paper and place inside an incubation box. Wet the paper with 1M $Na_2CO_3$.
Wash-paper: idem, but wet the paper with distilled water.
After 3 h incubation time, transfer the filters from the incubation box on the stop-paper and let them sit for 1 min. Transfer them to the wash-paper for another min., then dry them on a fresh piece of Whatman paper.
Store the filters by sticking them to a new sheet of Whatman paper using doublesided tape. Keep the filters that belong to one screen together. Wrap the papers with saran-wrap and seal the edges. Store together the filters belonging to the same screen.
Restreak cells from a positive colony after checking by the filter lift assay (for each clone). Take some fresh -LWH plates and divide into 8 sections. Number them according to the number of positives found. Mark them with date and bait name. Restreak cells from a single positive colony with 3 sterile sticks as described above to get isolated colonies.

D: PCR on Yeast Colonies
Introduction

PCR amplification of fragment of plasmid DNA directly on yeast colonies is an efficient procedure to identify sequences cloned into this plasmid. It is directly derived from a published protocol (Wang.H et al, Analytical Biochemistry, 237, 145–146, 1996). However, it is not a standardized protocol: in our hands it varies from strain to strain, it is dependent on experimental conditions (number of cells, Taq polymerase source, etc.). This protocol should be optimized to specific local conditions.

Materials
10× PCR buffer:
500 mM KCl
100 mM Tris HCl pH 9.0
15 mM $MgCl_2$
10 mM dNTP (mixture of the four dNTP at 10 mM each)
Taq polymerase (5U/µl) from Pharmacia (ref. 27.0799–02)
1 N NaOH
oligonucleotide upstream 100 ng/µl (oligo 52 for the W strand of the pACTIIst prey plasmid):
5'-CGC-GTT-TGG-AAT-CAC-TAC-AGG-GAT-G-3'
oligonucleotide downstream 100 ng/µl (oligo 53 for the C strand of the pACTIIst prey plasmid):
5'-GAA-ATT-GAG-ATG-GTG-CAC-GAT-GCA-C-3'
(see FIG. 8 for the sequence of pACTIIst plasmid).

Experiment

Take one colony with a toothpick. Resuspend the cells at room temperature in 10 µl 0.02N NaOH in an Eppendorf tube by turning the toothpick for several seconds in the NaOH solution. Prepare 0.02N NaOH just before use (5 µl 1N NaOH+245 µl water).

Incubate 5 min. at 100° C. For a large series, vortex the tubes before the incubation at 100° C. to counteract the sedimentation of the cells.

Put on ice immediately. Centrifuge the tube briefly to spin down the drops of condensation on the cap.

Vortex to resuspend the pellet and transfer 2 µl of the cell extract in a 0.5 ml PCR tube preincubated in an ice/water bath.

Prepare the PCR mix for X reactions (at least one more -or 10% more for large series-than the actual number of reactions).
for one reaction 24.6 µl H$_2$O (qsp 30 µl)

3.2 µl 10× PCR buffer 0.7 µl 10 µl dXTP 0.5 µl oligo 52

0.5 µl oligo 53

(0.5 µl Taq polymerase)

Mix all the components except the Taq enzyme.

Go to the thermal cycler. The block of the thermal cycler must be at 94° C. when you put your samples inside.

Add Taq enzyme to the PCR mix just before you distribute 30 µl of PCR mix per reaction.

PCR program: PTC-200 (MJ Research) or UnoII (Biometra)

step 1 3 min 94° C.

step 2 94° C. 30 sec.

step 3 55° C. 1 min 30 sec.

step 4 72° C. 3 min. (31 cycles step 2 to 4)

step 5 72° C. 5 min.

step 6 15° C. for ever.

Check the quality, the quantity and the length of the PCR fragment on 1% agarose gel. Take 3 µl from the PCR reaction and mix with 10 µl loading buffer (1.3 µl 10× blue loading buffer+8.7 µl H$_2$O; 10×blue loading buffer is: 10 mM Tris pHS, 1 mM EDTA, 30% glycerol, 0.2% bromophenol blue, 0.2% Xylene cyanol blue).

The length of the cloned fragment is the estimated length of the PCR fragment minus 300 bases that correspond to the amplified flanking plasmid sequences.

E: Sequencing PCR Fragments

Introduction

Two protocols are proposed, depending on the availability of an automated sequencing machine. It should be noted that the quality of the sequence will depend greatly on the quality of the PCR experiment that should be carefully analyzed (number of bands and intensity). Small amounts are generally sufficient as long as the preparation is not a mixture of several fragments.

Manual Sequencing

Materials

Sequenase PCR Product Sequencing Kit (Amershamn/USB ref:US70170

$^{35}$S dATP (ICN Ref: 56420H; spec. Act: 1000 Ci/mmole)

60 wells microtiter plate (Seromat Greiner ref:860173)

Primer MFR1 (10 picomoles/µl) 5'-GGC-TTA-CCC-ATA-CGA-TGT-TC-3'

20×TTE buffer:

216 g Tris Base 72 g Taurine (USB/Amersham Ref: US75824)

4 g NA$_2$EDTA,2H$_2$O

H$_2$O to 1000 ml

40% Acrylamide (Eurobio Ref: 018806)

Urea (Prolabo Ref:28 877.292)

10% Amonium Persulfate (APS)

TEMED

Experiment (According to Amersham)

Enzymatic Pre-treatment of PCR Product

It is convenient to do this pre-treatment in a thermal cycler.

Take 7 µl of PCR amplification product. (Do not vortex the tube to avoid taking cellular extract settling at the bottom of the tube).

Add 1 µl of ExoI (10 units) and 1 µl of Shrimp Alkaline Phosphatase (2 units). For large series, you can mix the 2 enzymes (vol/vol) and add directly 2 µl of the mix.

Gently mix the tube, briefly spin the tube and incubate at 37° C. for 15 min.

Inactivate the enzymes by heating at 80° C. for 15 min. Chill on ice.

Denaturation and Annealing

Add 1 µl of primer to each tube and denature by heating 3 min. at 100$_i$C.

Chill as quickly as possible in an ice/water bath for 5 min. Centrifuge briefly and chill on ice.

Elongation

Mark the microtiter plate wells with the name of the clones.

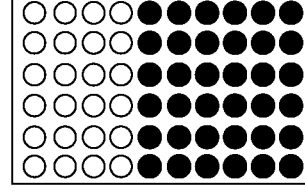

For each template aliquot into microtiter plate wells 2 µl of each termination mix in the order GATC. Keep at 4° C. or on ice and pre-warm at 37° C. before use.

Prepare elongation mix, keep on ice; for every reaction you need:

2 µl 5× sequenase buffer

1 µl 100 mM DTT

2 µl labeling mix (1:10 dilution)

0.5 µl $^{35}$S dATP

2 µl Sequenase (add Sequenase just before use)

For example, for 6 reactions, prepare:

14 µl 5×sequenase buffer

7 µl 100 mM DTT

14 µl labeling mix (1:10 dilution)

3.5 µl $^{35}$S dATP (5 µCi)

14 µl Sequenase (just before use)

Set timer at 3 min.

Add 7.5 µl elongation mix to annealed template. Wait 30 sec. before continuing with next sample. You can do a maximum of 12 templates in one go—yes, you have to work fast—keeping 15 sec. in between.

Aliquot 3.5 µl of elongation mix over each GATC termination wells within 30 sec (or 15 sec. when you do 12 templates in one go)

Wrap micro-titer plate with tape or para-film and put at 37° C. for 10 min. (can be placed in 37° C. incubator)

Stop termination by placing micro-titer plate on ice and adding 4 µl stop-solution to each well Denature samples just before loading:

Place micro-titer plate between two hot blocks at 95° C.; cover top of micro-titer plate with tissue to trap radio-active vapor. After 5 min. start loading gel.

6% Acrylamide Gel Electrophoresis
Apparatus: Sequi-GenII (Biorad 50 cm×40 cm).

The samples contain too much glycerol to use TBE buffer. Some distortions could appear. The gels must run in 0.8× TTE buffer.

Dissolve 72.2 g urea with 59 ml d'H$_2$O, 6 ml of 20×TTE, 18.75 ml of 40% Acrylamide. Add 500 µl of 10% APS and 120 µl of TEMED.

Pre-run the gel for 30 min. at 150 Watts
Run the gel at 100 Watts

Abi Cycle Seqencing
Materials
0.2 ml 8 tube-strips.
Exonuclease I (Amersham ref:E70073Z)
Shrimp Alkaline Phosphatase (Amersham ref: E70092Z)
Dye terminator (Perkin Elmer Ref: 402 122 or Amersham Ref: US79765)
Primer JC90 at 0.8 pmole/µl (see FIG. 8 for the map of pACTIIst plasmid)
50 mg/ml of Dextran-Blue dissolved in 25 mM EDTA (pH8).
loading buffer: deionized formarnmide and Dextran-Blue in a ratio of 5:1 (formamide to Dextran-Blue).
70% Ethanol in 0.5 mM MgCl$_2$.
70% Ethanol in H$_2$O.
40% Acrylamide (Biorad Ref: 161-0290)
Urea (Interchim Amresco Ref: 0568)
Experiment
Enzymatic Pre-treatment of PCR Product It is convenient to do this pre-treatment in a thermal cycler (block of 96 wells) and to use 0.2 ml 8 tubes strips.

Take 6 µl of PCR amplification product. (Do not vortex the tube to avoid taking the cellular extract at the bottom of the tube).

Add 1 µl of ExoI (10 units) and 1 µl of Shrimp Alkaline Phosphatase (1 unit). For large series, you can mix the 2 enzymes (vol/vol) and add directly 2 µl of the mix.

Briefly spin the tube (if necessary) and incubate at 37° C. for 15 min.

Inactivate the enzymes by heating at 80° C. for 15 min. Chill on ice.

PCR Sequencing

To each tube add 4 µl of primer at 0.8 pmole/µl and 8 µl of Terminator Ready Reaction Mix.

Place the 8 tubes strips in the thermal cycler programmed for:
10 sec. at 96° C.
5 sec. at 50° C.
4 min. at 60° C.
Repeat for 25 cycles.
4° C. for ever.

Precipitate at room temperature (RT) each tube with 75 µl of 70% Ethanol in 0.5 mM MgCl$_2$.

Centrifuge at 3000 g for 15 min. at RT in a Jouan centrifuge (4000 rpm).

Discard carefully the supernatant with a Pasteur pipette under vacuum.

Wash with 200 µl of 70% Ethanol.

Discard carefully the supernatant with a Pasteur pipette under vacuum.

Dry the sample on the bench.

Resuspend the pellet with 5 µl of loading buffer by vortexing.

Spin the samples.

Heat the samples at 95° C. for 3 min. in the thermal cycler.

Load 2 µl of the samples on an acrylamide gel.

6% Acrylamide Gel Electrophoresis

Dissolve 25 g urea with 19 ml of H$_2$O, 5 ml of 10×TBE, 7.5 ml of 40% Acrylamide. Add 250 µl of 10% APS and 23 µl of TEMED.

Pour the gel according to Perkin Elmer.

Run gel on ABI 373 machine according to Perkin Elmer.

F: Identification and Classification of the Candidates

1) Search in Databases

Introduction

This protocol varies from one lab to another depending on the local conditions for databases searches.

Materials
DNA Strider software (Marck. C; 16, 1829–1836, 1988)
SGD blast program (http://genome-www.stanford.edu; SGDB, Stanford, Calif.).
YPD (http://www.proteome.com; YPD, Proteome Inc., Beverley, Mass.).
NCBI blast program (http://www2.ncbi.nlm.nih.gov/BLAST).

Experiment
Sequence N-terminal Fusion of the Preys

Each clone is sequenced. Create one DNA Strider file per clone.

Read and enter the sequence from GGG ATC C. It is the BamHI site used to clone the yeast FRYL library. Starting with the 3Gs gives the coding frame of the Gal4 domain.

The 20 bases after the BamHI site are from the linker added to the genomic DNA fragments for the making of the FRYL library.

It is important to check if the linker sequence contains a mutation (especially frameshifts).

Read at least 50 bases of the insert.

Search chromosomal coordinates (chromosome number, strand w or c, position) with the SGD blast program.

Enter the data into in a column of an Excel Microsoft table.

Search the ORF corresponding to chromosomal coordinates (or the names of the two flanking ORFs). Extract and copy the sequence of the ORF into a DNA Strider file (÷1000 nt flanking regions).

Biological information on the ORF can be extracted from the YPD database.

Compare the insert sequence with the ORF sequence to get the exact location of the beginning of the insert related to the initiation codon.

Enter the data in a column of the table.

Compare the translated sequence of the clones with the protein sequence to check the coding frame.

Insert in a column of the table the length of the cloned fragment as estimated by agarose gel electrophoresis of the PCR fragments.

2) Classification of the Candidates

Considering the size of the library—a fusion point once every four bases—one can expect to find a given ORF several times as independent clones in a complete screen of such a library. However, the probability of the selection of a given fusion depends on the length of the interacting domain and on the position of the interacting domain along the coding sequence.

These parameters predict that all candidates fall into one of the following categories.

The categories A1, A2, A3 and A4 correspond to potentially encoded yeast ORFs. Their inserts start either inside the ORF coding sequence or upstream the initiation codon*.

The B category corresponds to fused polypeptides located in an intergenic region, in the reverse orientation of an ORF, in a non-polypeptide encoding region (rDNA, telomeric DNA, mitochondrial DNA) or in a Ty retrotransposon element.

The A1 category consists of candidates found several times as distinct independent clones.

The three other A categories correspond to candidates found only as a single fusion, even if the same clone is found several times:

The A2 category consists of fusions starting close to an initiation codon of a yeast ORF and at a distance smaller than 150 bases from the in-frame stop codon located upstream of this ORF. These candidates correspond to amino-terminal interacting domains. For such interacting domains, fewer candidates are expected since in-frame nonsense codons upstream of the yeast ORF interrupt its translation.

The A3 category candidates contain large coding inserts (over 1000 bases). This category may correspond to preys with a large interacting domain. Since the average size of inserts is 700 nt, candidates with large interacting domains are under represented.

The A4 category contains the other candidates. We cannot predict why these clones are found only once, although several hypotheses can be proposed, such as incorrect folding or toxicity of fusion proteins.

*Out of frame fusions are found. We do not discard these candidates but we label them with an asterisk to keep in mind that they may encode bonafide yeast polypeptides through a frame shifting event.

G: Plasmid Rescue from Yeast by Eeletroporation

Introduction

This experiment allows the recovery of a plasmid from yeast cells by transformation of *E. coli* with a yeast cellular extract. In the two-hybrid screening experiment, the diploid cells contain two different plasmids carrying the TRP1 (bait) and the LEU2 (prey) markers, respectively. We use a bacterial strain (MC1066) that carries the trp and leu auxotrophies that can be complemented by TRP1 and LEU2 yeast genes. Usually we select for the prey plasmid carrying LEU2 gene.

Materials
Plasmid Rescue
glass beads 425–600 $\mu$m (Sigma ref:G-8772)
Phenol/chloroform (1/1) premixed with isoamyl alcohol (Amresco ref: 0883)
Extraction buffer:
2% Triton X100
1% SDS
100 mM NaCl
10 mM TrisHCl pH8.0
1 mM EDTA pH8.0
Mix Ethanol/NH$_4$Ac: 6 volumes Ethanol with 1 volume 7.5 M NH$_4$ Acetate
70% Ethanol
yeast cells in patches on plates.

note: This protocol can be performed with frozen cells prepared from colonies or patches on plate, mixed in water and frozen directly at –20° C. ( in 50 $\mu$l H$_2$O).

Electroporation
SOC medium
M9 medium
Selective plates: M9-Leu+Ampicillin
2 mm electroporation cuvettes (Eurogentec ref: CE0002-25).

Experiment
Plasmid Rescue

First, add 400 $\mu$l of glass beads in each 1.5 ml eppendorf tube; second, add 200 $\mu$l extraction buffer (use multipipettor in case you do a large number of extracts); third, put the cells of each patch in the tube using blue tips ( the cells must coat 2 mm of the tip).

resuspend the cells in extraction buffer with the blue tip. Continue under the hood.

Add 200 $\mu$l Phenol/chloroform and vortex cells vigorously for 7 min.

Spin tubes 10 min, 15000 rpm.

Transfer 140 $\mu$l supernatant to a sterile eppendorf tube and add to each 500 $\mu$l Ethanol/NH$_4$Ac. Vortex.

Spin tubes 15 min 15000 rpm at 4° C.

Wash pellets with 250 $\mu$l 70% Ethanol. Dry pellets (5' in Speed Vac).

Resuspend pellets in 10 $\mu$l water. Store extracts at –20° C.

Electroporation
For a large number of electroporations:

Take a large ice-bucket and line up the electrocuvettes according to their number.

Alongside the cuvettes line up sterile eppendorf tubes numbered as the cuvettes but also carrying the clone-name. To every tube add 1 $\mu$l of yeast plasmid DNA-extract.

Mark the selective plates M9-Leu with the date, the name of the clone as well as the number of the cuvette.

Fill sterile eppendorf tubes marked with cuvette number and clone name with 1 ml of SOC medium.

Thaw a vial with electrocompetent *E.coli* (Strain MC1066 for selection on Leu and Trp). Keep vial on ice.

To every 1 $\mu$l yeast DNA sample add 20 $\mu$l electrocompetent cells; mix and transfer the mix to the cold electroporation cuvette.

Do the electroporation directly. Set the Biorad electroporator on 200 ohms resistance; 25 $\mu$F capacity; 2.5 Kvolts. Wipe cuvettes dry with a tissue paper and tap them to remove any trapped air-bubbles. Check if suspension makes contact with both electrodes. Place cuvette in the cuvette holder. Do the electroporation; time constant should be similar for every electroporation (around 4.7).

Directly add 1 ml SOC into the cuvette and transfer the cell-mix into sterile Eppendorf tube.

Let cells recover for 30 min at 37° C., spin the cells down 1 min, 4000 g and pour off supernatant. Keep about 100 $\mu$l medium and use it to resuspend the cells and spread them on selective plates (e. g. M9-Leu plates). Pipet the suspension over the glass beads and directly shake the plate to prevent a clustering of cells on the place where they have been pipetted (especially when plates are a bit dry).

Incubate plates for 36 h at 37° C.

Note: Wash the electrocuvettes and the caps with tap-water (apply high pressure to force out any remaining cells); rinse them with double distilled water and then With ethanol and let them dry. Close the cuvettes with the caps and store them in the supplier case according to their number.

Preparation of Electrocompetent Cells

Inoculate 1 liter LB with a 10 ml o.n. pre-culture of the *E.coli* strain of interest (MC1066 for Two Hybrid-plasmid rescue)

Grow to an OD$_{600}$ of around 0.6. (It should not be higher than 0.8).

Chill culture on ice and in cold-room for 15 min. From now on keep cells cool and handle with care.

Pellet cells 15 min 3000 g at 4° C.
Resuspend cells in 1 liter cold sterile water
Pellet cells 15 min 3000 g at 4° C.
Resuspend cells in 500 ml cold sterile water
Pellet cells 15 min 3000 g at 4° C.
Resuspend cells in 20 ml sterile 10% glycerol
Pellet cells 15 min 3000 g at 4° C.
Resuspend cells in 2 ml sterile 10% glycerol and complete up to a final volume of 3 ml (about $3.10^{10}$ cells/ml).

Distribute in aliquots of 50 $\mu$l or multiples of that. (You'll take 50 $\mu$l per normal electroporation and 20 $\mu$l when you have to rescue a large number of plasmids)

Freeze the aliquots in dry Ice/EtOH but take care to prevent traces of EtOH entering into the tubes) and store at –80° C.

H: Plasmid Minipreps from *E.coli*
Materials
STET buffer:
  8% Sucrose
  50 mM EDTA pH8
  10 mM TrisHCl pH8
  0.5% Triton X100
20 mg/ml freshly made Lysozyme (dissolved in water)
EtOH/NH$_4$Ac: mix 6 volumes of ethanol with 1 volume of 7.5 M NH$_4$ Acetate.
70% Ethanol
TE pH8
STET/Lysozyme: for 10 minipreps: 3 ml STET÷250 µl 20 mg/ml Lysozyme
Experiment
  Start with 2 ml bacterial cultures grown overnight.
  Transfer 1.5 ml to non-sterile Eppendorf tubes, pellet cells by centrifugation 20 sec, discard the supernatant by overturning the tubes. Keep about 100 µl medium and use it to resuspend the cells with vortex. BE CAREFUL! all the cells must be well resuspended.
    Add 300 µl STET/Lysozyme buffer
    Keep on ice for 5 min.
    Incubate 2 min at 100° C. (use hot-block rack for transfer).
    Put on ice.
    Spin 15 min at 4° C.
    Take out the pellet with a toothpick
    Add 750 µl EtOH/NH$_4$Ac to supernatant, vortex
    Spin 10 min, wash with 500 µl 70% EtOH, dry pellet (5 min in speed-vac).
    Dissolve pellet in 50 µl TE by incubation at 65,C for 5 min and vortex.
I: Yeast Transformation
Adapted from: Gietz et al, Yeast 11, 355–360, 1995
Material
2 ml eppendorf tubes
50 ml tubes
Media
liquid medium for preculture: YPglu or selective medium when the yeast strain harbors a plasmid.
plates for plasmid selection.
Solutions
Yeast carrier DNA (Clontech ref: K1606-A)
1M Li Acetate (filter sterilized) (Fluka ref: 62395)
10× TE (100 mM Tris pH 7.5; 10 mM EDTA) autoclaved
Sterile distilled water
Prepare 0.1 M LiAc/TE solution by mixing:
  100 ml 1M LiAc
  100 ml 10× TE
  800 ml sterile distillated water
40% PEG 4000 (Merck ref:807 490) filtrated on Nalgene (0.2µ).
40 g of PEG 4000
10 ml 1M LiAc
10 ml 10× TE
add H$_2$O to a final volume of 100 ml.
Experiment
  For one transformation you need 10 ml of culture (OD=0.6; with our spectrophotometer, 1 OD corresponds to $10^7$ cells per ml) which will be finally resuspended in 50 µl 0.1M LiAc/TE.
    all steps are performed at room temperature
    Set up a preculture of the strain in 20 ml of appropriate medium the day before
    Grow o.n at 30° C. until saturation
    Inoculate 50 ml of medium (for 5 transformations) at 0.15 OD with the o.n preculture
    Grow until OD=0.6
    Centrifuge the cells in 50 ml sterile tubes at 5000 g (4000 rpm)for 3 min
    Discard the supernatant by overturning the tube
    Resuspend the pellet with 2 ml of sterile water
    Transfer into an 2 ml eppendorf tube.
    Centrifuge the cells at 4000 g (6500 rpm) for 1 min.
    Repeat the washing twice with 2 ml of water and twice with 2 ml of LiAc/TE solution.
    Centrifuge at 4000 g 1 min. after each washing and resuspend each time the cells by vortexing.
    Resuspend finally the pellet with 200 µl of LiAc/TE solution. Adjust to 250 µl.
    In the meantime, mark your tubes. Do not forget one tube without plasmid DNA.
    Distribute in sterile 1.5 ml Eppendorf tube:
    1 µl plasmid DNA (from a mini-prep or at 0.1 mg/ml)
    5 µl Yeast carrier DNA
    50 µl of cells
    350 µl of 40% PEG
      Mix by inversion
      Incubate 30 min at 30° C.
      Heat shock cells at 42° C. for 20 min.
      Add 700 µl of water. Mix by inversion.
    Spin cells for 1 min in a microfuge at 4000 g. Discard supernatan.
      Resuspend the cells with 100 µl of water
      Spread the cells on appropriate medium plates and incubate at 30° C. for two-three days.
J: Characteristics of the FRYL Library
Origin of the plasmid: pACTIIst.
Origin of the genomic DNA: strain Ym955 (a gift of M. Johnston).
Ym955 genotype: Mat a ura3-52, his3-200, ade2-101, lys2-801, leu2-3,112, trp1-901, tyr1-501, gal4-542, gal80-538.
Note: his3-200, trp1-901, gal4-542 and gal80-538 are deletions of the whole coding sequence.
Library Construction into *E.coli*
  FRYL Genomic library was made according to the procedure of Elledge et al (P.N.A.S., 1991, 88, 1731–1735).
  Genomic DNA was sonicated, made blunt by 3 modification enzymes (Mung bean nuclease, T4 DNA Polymerase and Klenow fragment). Adaptors were ligated to blunt ends.
  Adaptors were designed to allow blunt ligation at one extremity and cohesive ligation with a 3 nucleotides overhang at the other end.
  Sequence of adaptors:
  5'-ATCCCGGACGAAGGCC-3'
  5'-GGCCTTCGTCCGG-3'
  Only the former was phosphorylated before annealing to avoid self-ligation of the adaptors. After ligation the inserts were purified from free adaptors and small fragments on a Chroma Spin column (Clontech).
  The pACTIIst vector was digested with BamHI and the extremities were filled-in with dGTP by the Vent (Exo⁻) polymerase (New England Biolabs), generating extremities complementary to the 3 nucleotides overhang of adaptors but preventing self-ligation of the vector. (BamHI sites are reconstituted at each end of the insert).
  Inserts and vectors were ligated together and ligation products were used to transform *E.coli* MR32.
  $5.10^6$ clones were obtained. All transformants were scraped from dishes and the pool of transformants was frozen in LB/glycerol. The titer of the library is $1-2.10^9$ transformants/ml.
*E. coli* FRYL Library Characteristics
  $5\ 10^6$ clones 72.5% with insert i.e $3.6 \times 10^6$ clones.
mean length of DNA fragments: 700 bp
$3.6 \times 10^6$ clones represent $3.6 \times 10^6$ independent genomic fragments i.e. $3.6 \times 10^6$ random fusion points in the genome.
Yeast genome: $14 \times 10^6$ bases
In the FRYL library, the yeast genome is cut every 4 bases ($14 \times 10^6$ divided by $3.6 \times 10^6$)
FRYL Library Transformed in the Y187 Yeast Strain The Y187 yeast strain is transformed according to standard procedures with the FRYL library DNA. As many as possible transformed yeast colonies are collected and pooled. Aliquots are stored at −80° C.

Typically, several hundreds plates are used to allow the growth of 10.000 to 30.000 colonies per plate (90 mm diameter). Ideally, three times more yeast colonies than the initial number of E. coli clones should be collected. The same calculation occurs to estimate how many yeast diploid cells should be screened to cover the original library.
FRYL E. coli library: $5.10^6$ clones.
FRYL yeast frozen library: around $15.10^6$ clones.
Diploids to be tested: $45.10^6$ cells.
The mating efficiency is usually above 20% and often around 50%.
1 Vial should contain at least $4.10^8$ cells
Theoretical calculation:
$(1-p) = (1-1/n)^N$
N=number of clones that are tested (number of yeast colonies)
n=number of original clones (number of E. coli clones)
p=probability to test a given clone of the original library
For example: with $n = 5.10^6$ E. coli clones

| N | p |
|---|---|
| $23.10^6$ | 99% |
| $15.10^6$ | 95% |
| $13.10^6$ | 93% |
| $7,6.10^6$ | 78% |
| $7,15.10^6$ | 76% |

K: Gene Disruption and Complementation
Gene disruptions were performed with a TRP1 cassette replacing the entire ORF (Baudin et al., 1993). BMA64 diploid cells were transformed with a PCR-derived linear DNA fragment, then transformants were re-isolated and disruptions were controlled by Southern analysis. After tetrad dissection, spores were incubated on rich medium at 23° C. for three days and clones were then replica-plated on rich medium and on -W plates and incubated at 23°, 30° and 37° C. For those genes found essential, the diploid strain was transformed with a plasmid encoding a Gal4 fusion protein selected during the two-hybrid screen. Tetrads were then dissected in order to test the complementation of the disruption by the expression of the fusion gene.
L: Construction of the FRYL Library
Protocols
Step 1. Preparation of Yeast Genomic DNA from Ym955 Strain according to Standard Procedure;
Origin of the genomic DNA: Ym955 (a gift of M. Johnston).
Ym955=ura3-52, his3-200, ade2-101, lys2-801, leu2-3,112, trp1-901, tyr1-501, gal4-542, gal80-538.
his3-200, trp1-901, gal4-542 and gal80-538 are deletions of all coding sequences.
Step 2. Preparation of Randomly Sheared Yeast DNA by Sonication
44 μg of yeast genomic DNA in a volume of 100 μl were sonicated to an average size of 1000 bp (range size 200 bp-2000 bp).

Step 3. Blunting the DNA Fragments Ends with Mung-Bean Nuclease Treatment and T4 DNA Polymerase Repair.
Yeast sheared DNA at a concentration of 0.2 mg/ml was treated with 40 units of Mung-Bean nuclease in a final volume of 200 μl for 30' at 30° C.
Phenol-chloroform extraction and precipitation with ethanol.
Dissolved the sheared DNA (40 μg) in 143 μl of $H_2O$; Treated with 40 units of T4 polymerase, 100 μM dNTP in a final volume of 200 μl for 10' at 37° C.
Added 11 units of Klenow enzyme and incubated for 10' at room temperature and 1 hr at 16° C.
Phenol-chloroform extraction and DNA precipitation with ethanol.
Dissolved the precipitated DNA in 10 μl of $H_2O$.
Step 4. Preparation of the Adapters for Ligation with the Sheared Yeast DNA
Mixed
3 μg oligo 160
3 μl ATP 10 mM
3 μl 10× T4 polynucleotide buffer
1.5 μl T4 polynucleotide Kinase (10 u/μl)
$H_2O$ qsp 30 μl
Incubated 30' at 37° C. followed by 5' at 95° C. Added 15 μl (30 μg) of oligo 159
Incubated: 5' at 95° C., 10' at 68° C., 15' at 42° C., 10' at room temperature.
Sequence of the oligo pL 160: 5'-ATCCCGGACGAAGGCC
Sequence of the oligo pL 159 5'-GGCCTTCGTCCGG
Step 5. Ligation of Adaptors to the Sheared DNA
Added to the 10 μl of sheared yeast DNA from step 3: 38 μl of adaptors from step 4, 6 μl 10×ligation buffer, 3 μl BSA 1 mg/ml, 0.6 μl DTT 1M, 1.2 μl ATP 10 mM, 1 μl T4 DNA ligase (Biolabs 2000000 U/μl).
Incubated at 4° C. overnight.
Added 1 μl T4 DNA ligase and incubated 24 hrs at 15° C.
Added 40 μl of $H_2O$ to the ligation
Step 6. Purification of the DNA from Unligated Adaptors and Its Size Fractionation on a Chroma-spin 400 Column (Clontech ref:K1323-1)
Split the solution into two aliquots of 50 μl each.
Fractionated one aliquot on a chroma spin 400 column according to the manufacturer instructions
Collected the 1st fraction from the column in a final volume of 50 μl.
Preparation of the Vector pACTII st
Step 7. Digestion Vector with the Restriction Enzyme BamHI
Digested to completion 20 μg of pACTIIstop vector with BamHI restriction enzyme in a final volume of 100 μl at 37° C.
The vector has been phenol-chloroform extracted and precipitated with ethanol.
Step 8. Dephosphorylation of the Vector Ends
20 μg of pACTIIst from step 7 were dephosphorylated with 3 units of calf intestinal alkaline phosphatase in a final volume of 110 μl for 1 hr at 37° C.
The phosphatase was inactivated by adding 1 μl of a 0.5 M solution of EDTA ph 8 and incubation 10' at 75° C.
The solution was phenol-chloroform extracted and the DNA recovered by ethanol precipitation. The DNA was resuspended with 100 μl of TE pH8
Step 9. G-filling-in of the BamHI Cut-vector
To fill-in the ends of the vector with dGTP the following reactions were set up:

50 μl (10 μg) pACTIIst cut BamHI from step 8
15 μl Vent polymerase buffer 10x
6 μl dGTP 10 mM
5 μl triton X100
H₂O qsp 145 μl
Incubated the solution 5' at 72° C.
Added 5 units of exo⁻ Vent DNA polymerase
Incubated 1' at 72° C.
Put the reaction on ice
The DNA was extracted with phenol-chloroform and recovered by ethanol precipitation.
Dissolved pACTIIst in 100 μl of TE ph 8.

Step 10. Ligation Sheared Yeast Genomic DNA from Step 6 into pACTIIst Vector from Step 9

The two following reactions were set up to ligate an aliquot of randomly sheared yeast DNA to the pACTIIst vector:
50 μl pACTIIst vector (5 μg) from step 9
25 μl yeast genomic DNA (5 μg) from step 6
50 μl T4 ligase buffer 10x (Biolabs)
365 μl H₂O
2 μl T4 ligase 2000000 u/μl Biolabs
Incubate the reaction overnight at 15° C.
the ligation reaction was precipitated with ethanol Step 11. Preparation of the Library into *E. coli* Strain MR32

The ligation was resuspended in 50 μl of H₂O. Each 2,5 μl of ligation were independently electroporated into 50 μl of electrocompetent *E.coli* strain MR32 cells. Each electroporated tube was diluted in 1 ml SOC buffer. The 20 ml of transformants were pooled. 50 μl were plated on LB plate+ampicillin to get a density of 13000–20000 cfu/plate.

The library into the pACTIIst vector consists of $5.10^6$ independent transformants.

Transformants of the library into pACTIIst were washed away with 3 ml/plate. 750 ml of LB medium at a concentration of 43 OD$_{600}$/ml were collected.

Aliquots of the bacterial FRYL library were stored at −80° C. ($2.10^9$ cells/ml/vial).

The rest of the cells was collected by centrifugation and the cell pellet used for plasmid preparation.

Step 12. Plasmid Library Preparation

Plasmids were collected using Qiagen columns according to manufacturer instructions.

The plasmid library was dissolved at a concentration of 1 mg/ml.

Preparation Library into Yeast Strain Y187

Step 13. Yeast Transformation

400 μg of plasmid library were used to transform 1 liter of Y187 yeast strain cells at a concentration of 0.9 OD$_{600}$/ml according to standard conditions.

Transformants were plated on solid synthetic media lacking leucine at a density of 10000 cfu/plate $13 \times 10^5$ independent transformants were obtained for the FRYL1 library.

Y187 transformants that constitute the library were collected in 1400 ml of YPGlu at a concentration of 90 u. OD600/ml; 40 g. of 100% glycerol were added per 100 ml of yeast transformant solution and the library was aliquoted in 1212 vials at 1,5 ml/vial ($4 \times 10^8$ cells/vial) and stored at −80° C.

M: MEDIA
Yeast Media
YPGLU
1% yeast extract
2% bactopeptone
2% glucose 10 g Bactopeptone (Difco ref: 0118-17-0)
10 g Yeast Extract (Difco ref: 0127-17-9)
20 g Glucose (Merck ref: 1.08342)
Fill to 1 liter with distillated water
Shake until all ingredients are dissolved
For plates add 20 g Bacto-agar (Difco ref:0140-01)
Autoclave 20 min, 110° C. (at higher temperatures sugars and amino acids might be degraded), let cool to 60° C., (when required add antibiotics) mix gracefully so that no bubbles are formed
Pour sterile plates: 25 ml per plate Drop-Out Yeast Medium
6.7 g Yeast Nitrogene Base w/o amino acids (Difco ref:0919-15-3)
20 g D-glucose (Merck ref:1.08342)
2 g drop-out powder mix (see below)
Fill to 1 liter with distilled water
Shake/stir until all ingredients are dissolved
For plates: add 20 g bacto-agar (Difco ref:0140-01), mix
Autoclave 20 min, 110° C. (at higher temperatures sugars and amino acids might be degraded), let cool to 60° C., (when required add antibiotics) mix gracefully so that no bubbles are formed
Pour sterile plates: 25 ml per plate The four Two-hybrid drop-out mixes are:
(selection on bait plasmid);
-W (selection on bait plasmid);
-L (selection on library plasmid);
-LW (selection on both plasmids);
-LWH (selection for both plasmids and two-hybrid interaction inducing the HIS3 reporter).
-LWH+AT (AT may be added at a concentration between 1 mM to 50 mM depending on the bait)
Tetracycline (12 mg/ml stock solution) is added after cooling the agar to 60° C.
3-Amino 1,2,4 Triazole (3-AT Sigma Ref: A-8056) is added after cooling the agar to 60° C. using a 1M stock solution.

Drop-out Powder Mix
Mix 2 g of each component:
Adenine; Alanine; Arginine; Asparagine; Aspartic acid; Cystein; Glutamic acid; Glutamine Glycine; Histidine; Isoleucine; Lysine; Methionine; Phenylalanine; Proline; Serine; Threonine; Tyrosine; Tryptophan; Uracil; Valine plus 4 g of Leucine.

In total 22 essential components from which the underlined ones have to be omitted in the case of the two-hybrid drop-out mixes.

| BACTERIAL MEDIA | |
|---|---|
| SOC BUFFER | |
| 2% Tryptone | (20 g/l) |
| 0.5% Yeast Extract | (5 g/l) |
| 10 mM NaCl | (0.58 g/l) |
| 2.5 mM KCl | (0.19 g/l) |
| 10 mM MgCl₂ | (2.03 g/l) |
| 10 mM MgSO₄ | (2.46 g/l for MgSO₄.7H₂O) |
| 20 mM glucose | (3.6 g/l) |

M9 Drop-out Plates
1 g drop-out mix (the same as for yeast medium) (for library plasmids M9-leu: -L; for bait plasmids M9-Trp: -W)
20 g bacto agar in 878 ml double distilled water,
Autoclave for 20 min at 110° C.
Let cool to 60° C.;
Add aseptically:

100 ml 10× M9 (autoclaved)
10 ml 20% glucose (autoclaved)
2 ml 1M MgSO$_4$ (autoclaved)
10 ml 20 mM CaCl$_2$ (autoclaved)
1 ml 1000× Ampicilline (100 mg/ml stock)
Pour plates (20 ml/plate)
for 1 liter of 10× M9:
60 g Na$_2$HPO$_4$;
30 g KH$_2$PO$_4$;
5 g NaCl;
10 g NH$_4$Cl
Adjust to pH 7.4
 * One plate is needed for every rescue

EXAMPLES

Example 1

Complete Yeast Genome Screening in a Two-hybrid Strategy

We constructed a yeast genomic DNA library into a derivative of the pACTII two-hybrid bait vector (Clontech). The genomic DNA was sonicated and cloned following a procedure that prevents the cloning of multiple fragments in the same plasmid (see Experimental Procedures, Elledge et al., 1991). We recovered 5.10$^6$ independent E. coli clones that were pooled to constitute the FRYL library. We analyzed 40 independent clones: 72% of them contained an insert 200 to 1400 nt long. The average size of the inserts was 700 bp. Considering the size of the yeast genome (14.10$^6$ bp), a fusion event occurs statistically once every four bases, leading to an in frame fusion between the Gal4 activation domain and a yeast ORF once every 24 nucleotides. One can expect to find several times a given ORF as independent clones in a complete screen of such a library. However, the probability of the selection of a given fusion depends on the length of the interacting domain and on the position of the interacting domain along the coding sequence.

These parameters predict that all candidates fall in 5 categories (FIG. 1). The four A categories correspond to yeast ORFs. The B category corresponds to fused polypeptides located in an intergenic region, in the reverse orientation of an ORF, in a non-polypeptide encoding region (rDNA, telomeric DNA, mitochondrial DNA) or in a Ty retrotransposon element. A1–A4 candidates encode potentially interesting fused polypeptides. Their inserts start either inside the ORF coding sequence or upstream the initiation codon. The A1 category consists of candidates found several times as independent clones. The three other A categories correspond to candidates found only as a single fusion, even if the same clone is found several times. The A2 category consists of fusions starting close to an initiation codon of a yeast ORF and at a distance smaller than 150 bases from the in-frame stop codon located upstream this ORF. These candidates correspond to amino-terminal interacting domains. For such interacting domains, fewer candidates are expected since in-frame non sense codons upstream of the yeast ORF interrupt its translation. The A3 category candidates contain large coding inserts (over 1000 bases). This category may correspond to preys with a large interacting domain. Since the average size of inserts is 700 nt, candidates with large interacting domains are under represented. The A4 category contains the other candidates. We cannot predict why these clones are found only once, although several hypotheses can be proposed, such as incorrect folding or toxicity of fusion proteins (Fields and Jang, 1996).

Most candidates in the A categories are fused to the Gal4 sequence in the reading frame of the yeast gene. However, several of them are out of frame and we show that, at least in some cases, frameshifted translation occurs (see below). In the Tables, the out of frame candidates are labeled with an asterisk.

Figure 2:
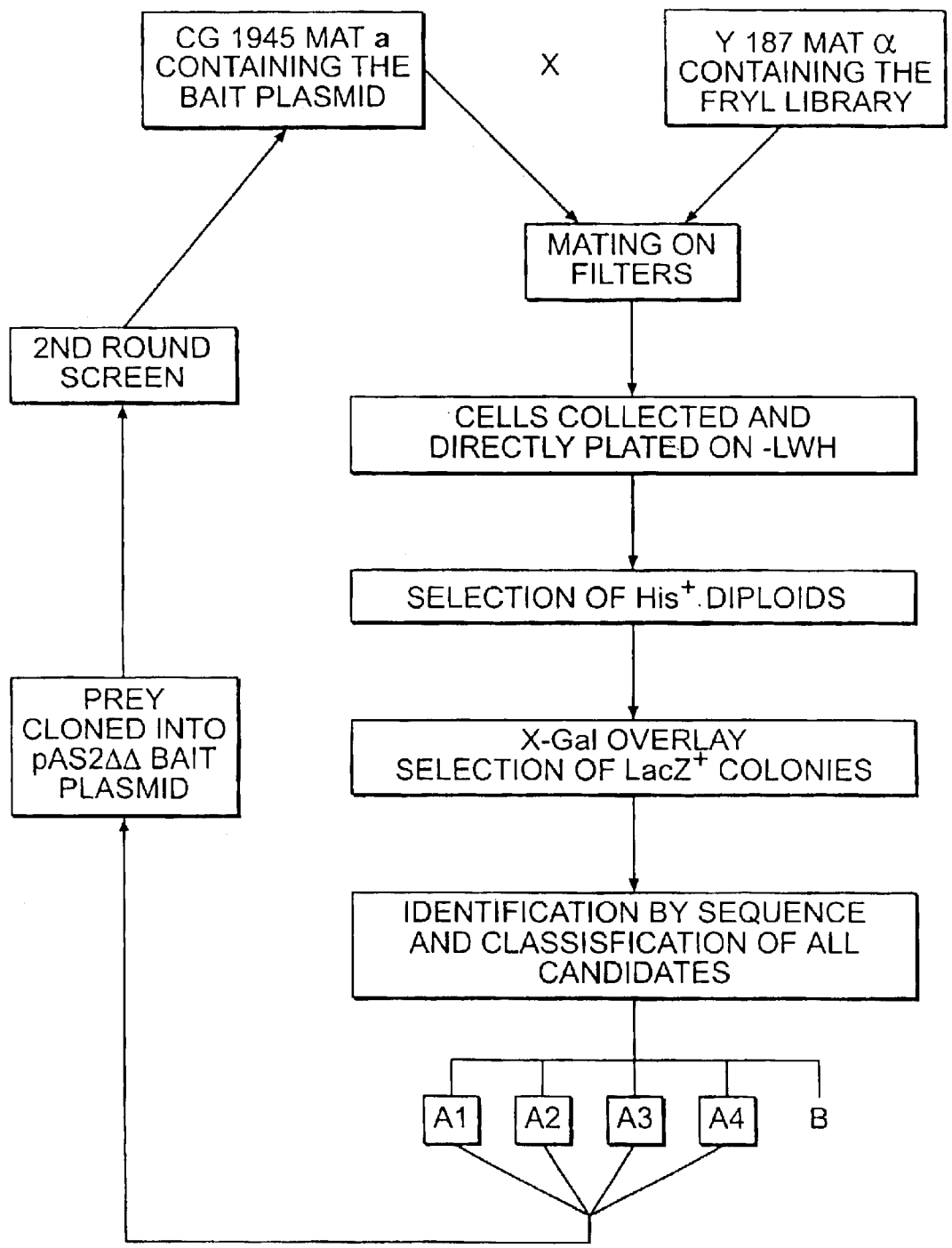
FIG. 2. A mating strategy for multiple round two-hybrid screens: See Experimental procedures for details.

The classification of interacting candidates found in a two-hybrid screen requires a reproducible experimental protocol that allows a complete coverage of the library. For this purpose, we developed a mating strategy (FIG. 2; see also Experimental Procedures). In brief, we transformed the Y187 strain with the FRYL library DNA. Thirteen million yeast colonies, corresponding to an almost complete coverage of the E. coli library were recovered, aliquoted and frozen. Independently, bait plasmids were introduced in the CG1945 strain. The Y187 strain contains a sensitive LacZ reporter gene whereas the CG1945 strain has a non-leaky HIS3 reporter gene that enables the selection of positive diploids in the absence of 3-aminotriazol (3-AT). The mating procedure allows a direct selection on selective plates because the two fusion proteins are already produced in the parental cells. No replica plating is required. We routinely obtain a 20% mating efficiency and regularly up to 50% mating efficiency. Screening forty million diploids ensures the coverage of the yeast library. The X-Gal assay is directly performed on His$^+$ colonies. Prey plasmids from all colonies are sequenced at the Gal4 junction.

Figure 3:
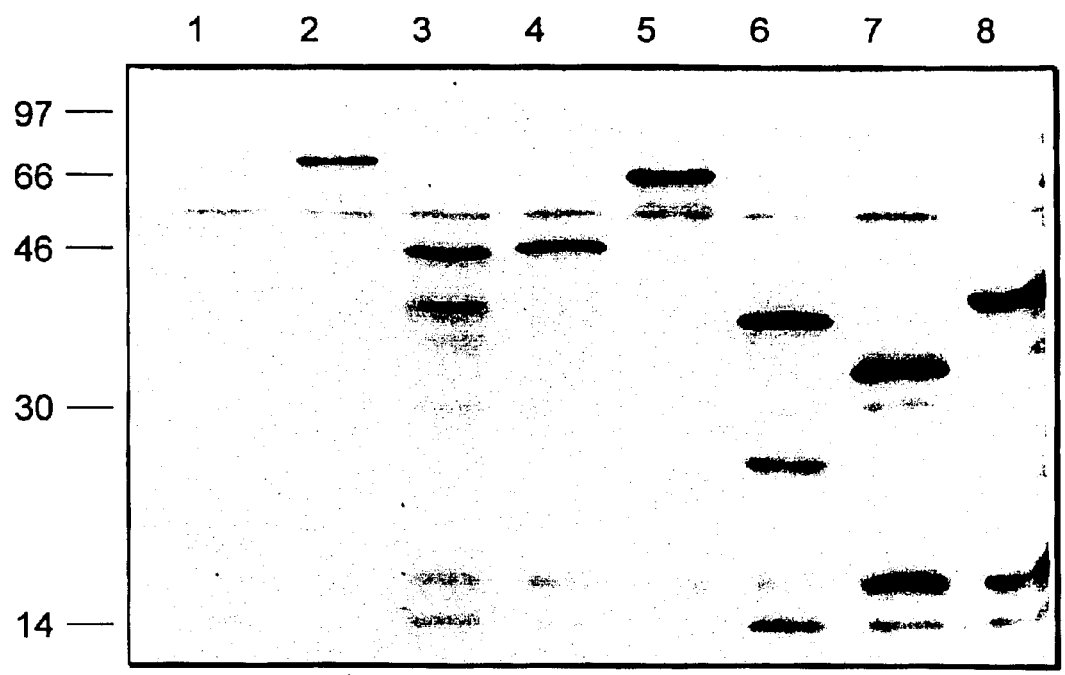
FIG. 3. Western blot analyses of Gal4 fusion proteins used as baits: Extracts of CG1945 cells transformed with the various bait plasmids were separated by a 12% SDS-denaturating gel, blotted and analyzed with an anti-Gal4 DNA binding domain antibody. The expected molecular weight (kD) of the fision proteins is given in brackets. 1: pAS2ΔΔ (16); 2: Prp9p (79); 3: Prp11p (46); 4: Prp21p (49); 5: Cus1p (66); 6: Yor319w (40); 7: Yjr022w (30); 8: Yer029c (38); 9: Mud1p (50); 10: Snp1p (50); 11: Mud2p (76); 12: Ylr116w (69); 13: Yir009w (29); 14: Ylr456w (40); 15: Smd1p (32); 16: Smd3p (27).
Figure 3:
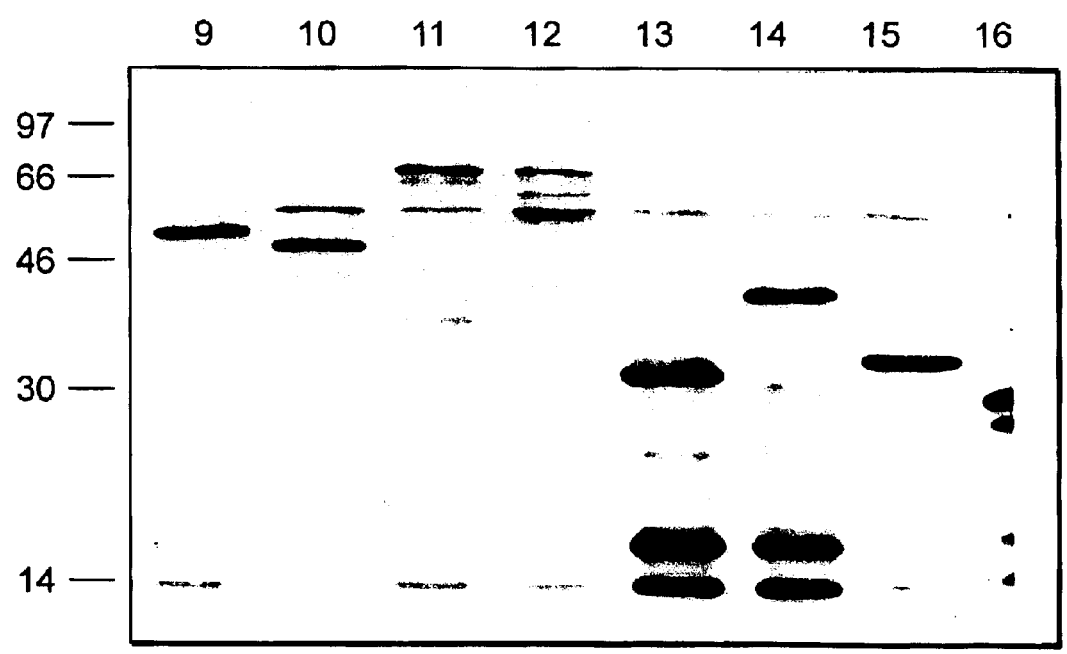

The bait plasmid is one of the key parameters for a two-hybrid screen. The pAS2 vector encodes a GAL4-DNA binding domain. It was found very efficient for protein-protein interaction analyses (Legrain et al., 1994). However, the CYH2 gene was found toxic when overexpressed (roughly 10% plating efficiency for cells containing this plasmid, as opposed to 80% for cells transformed with a derivative of pAS2 deleted for the CYH2 gene, data not shown). This is a serious limitation for large scale screens. In addition, poor specificity was observed in screens due to the presence of the HA epitope. After deletion of this sequence, we obtained 10 times less His$^+$, LacZ$^+$ colonies in a two-hybrid screen with Prp21p (data not shown). For these reasons, baits were cloned as full length ORFs into the pAS2ΔΔ vector which was devoid of the CYH2 gene and the HA epitope (see Experimental procedures). Expression of the fusion proteins was controlled by western blot (FIG. 3). Fusion proteins were detected roughly at the expected molecular weight.

Example 2

Exhaustive Two-hybrid Screens with Yeast Proteins Are Highly Selective and Point Toward Limited Sets of Interacting Proteins The ten proteins chosen as initial baits in two-hybrid screens are nuclear proteins implicated in the pre-mRNA splicing pathway (Table 1). Smd1p and Smd3p are core proteins of the snRNP particles, Snp1p and Mud1p are specific proteins of the U1 snRNP (yeast homologues of human U170K and U1A, respectively), Mud2p is associated with the U1 snRNP during early steps of spliceosome assembly, Yir009w is a U2 snRNP particle protein (the yeast homologue of the human U2B"), Prp9p, Prp11p and Prp21p are the three components of the yeast SF3a factor associated with the U2 snRNP particle and Cus1p is the first identified component of the yeast SF3b factor, also associated with the U2 snRNP (see for review Beggs, 1995; and also Tang et al., 1996; Wells et al., 1996).

Figure 4:
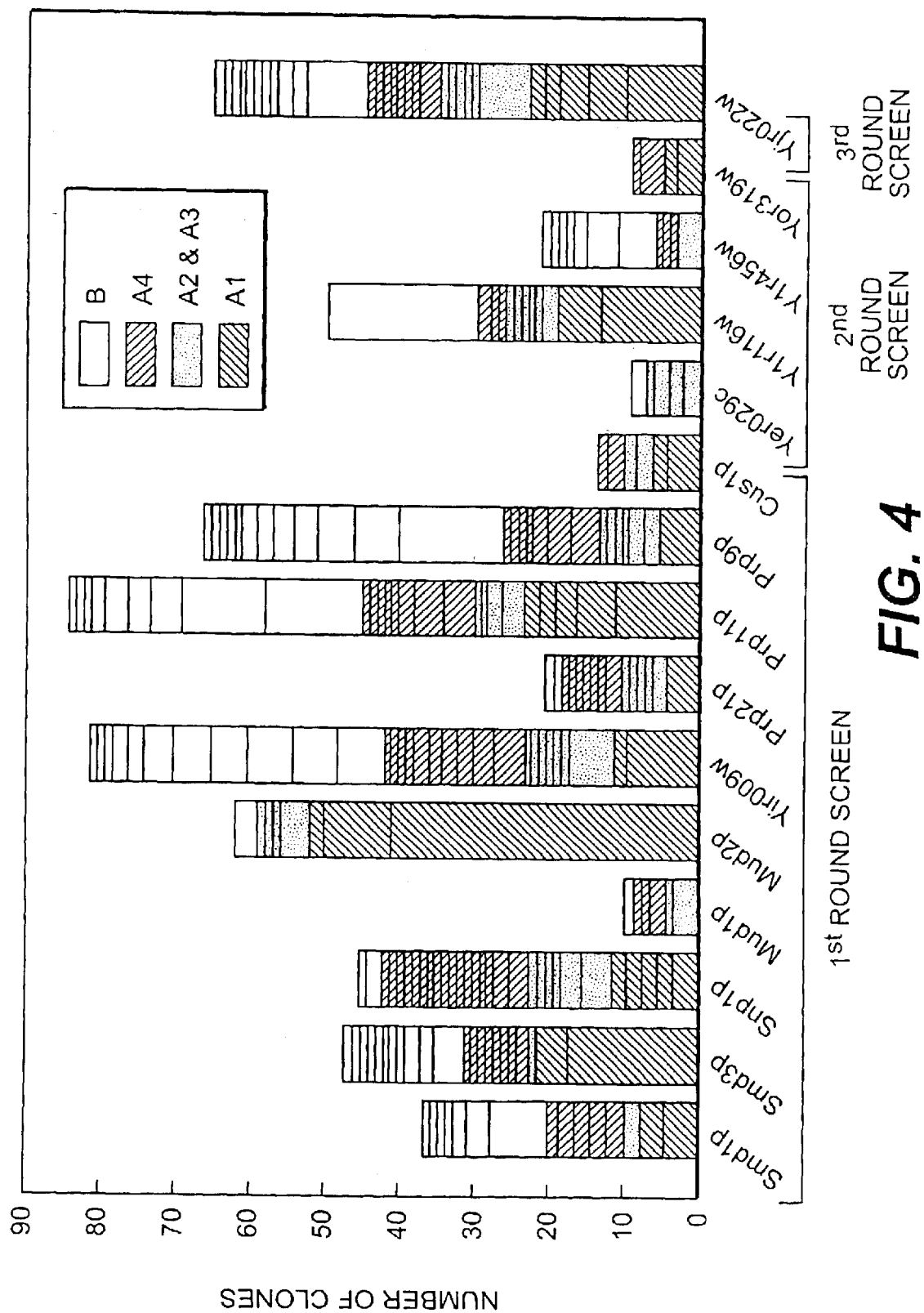
FIG. 4. Distribution profiles of preys found in two-hybrid screens: All preys selected with a bait indicated below each bar are represented according to the classification given in FIG. 1 (see insert; for clarity, A2 and A3 preys are grouped). Subdivisions within a category reflect the number of preys falling within the same genomic locus.

The number of His$^+$ colonies varied considerably among the various screens (58 to 17000, Table 1). However, the number of His+, LacZ+ colonies was less variable (10–86), allowing a selection of roughly one positive clone for one million diploid (ranging from 0.1 to 4 per million). The number of recovered and identified candidates was usually very close to the initial number of His+, LacZ+ colonies (Table 1). Thus, the collection of identified clones is a fair representation of the initial clones selected in the screens. Preys were sequenced and grouped according to the classification described above (FIG. 1). As illustrated in FIG. 4, the various baits behave differently. The ratio of identified loci out of the number of selected preys varied from bait to bait (e.g. 8 out of 61 in the Mud2p screen as compared to 30 out of 46 in the Snp1p screen). In addition, the categories of preys were differently represented in screens selecting few clones (e.g. 13 preys falling in two A1, two A2 and two A4 in the Cus1p screen and 9 preys falling in two A2, three A4 and one B in the Mud1p screen). Finally, we note that B loci can be efficiently selected as multiple independent fusions. The most likely interpretation is the selection of a given artificial polypeptide that interacts strongly with the bait. Within a screen, typically two or three ORFs fall into the A1 category. Many preys are proteins of unknown function and some of them were in turn used as baits (Table 1). They also behaved differently from one another (FIG. 4), but in every case, few ORFs were selected again, allowing the choice of a novel prey as bait for a third round of screening.

Example 3

Two-hybrid Screens with Known Proteins Identify Novel Protein-protein Interactions with Potential Biological Significance The first round of screening was done with known splicing factors. All selected ORFs are listed in the following tables according to the official yeast ORF nomenclature with their gene name and their function, when available (Tables 2 to 7, Garrels, 1996). The category of candidates (FIG. 1) is given for each ORF.

The Smd1p and Smd3p screens select 8 and 11 different ORFs respectively, with two A1 candidates in each case (Table 2). One A1 Smd3p candidate is Yer029c, a protein that exhibits Sm motifs shared by core proteins of snRNP particles (Hermann et al., 1995; Seraphin, 1995). This new protein was used for a second round two-hybrid screen (see below).

Screens performed with the two U1 snRNP-associated proteins, Snp1p and Mud1p, reveal two extreme situations (Table 3). We found 42 clones in 28 different genetic loci with Snp1p as bait, including five A1 ORFs. Among the A1 ORFS there were transcriptional factors, including Swi1p, that were also obtained with other baits (see below). In contrast, only eight candidates falling in five genetic loci were found with Mud1p, none of them falling in the A1 category. None was considered for further screening.

The Mud2p screen is very striking (Table 4): only seven ORFs were selected, one of them, Ylr116w, represented by more than 60% of the clones. This unknown yeast gene was chosen as bait in a second round two-hybrid screen. Two other candidates of unknown functions are the Lpg4p and the Smy2p proteins, which are highly homologous with each other.

The Yir009w (U2BOO) screen identified two genetic loci in the A1 category (Table 5). One of them, YLR456W, encodes a protein of unknown function that was chosen as a second round bait.

Screens were also performed with Prp9p, Prp11p and Prp21 p (Table 6). Prp9p and Prp 11p were previously shown to interact with Prp21 p altogether forming the yeast homologue of the human SF3a splicing factor (Bennett and Reed, 1993; Brosi et al., 1993; Legrain and Chapon, 1993). The Gal4-Prp9p fusion could not be used due to a very strong direct activation of reporter genes, and the two-hybrid screen was performed with the LexA-Prp9p fusion as bait and in the presence of 5 mM 3-AT to eliminate a high background of residual growth. Still the expected PRP21 prey was found among 14 different genetic loci. The Prp11p screen selected 17 different ORFs. Five of them correspond to the A1 category, Prp21p being the most represented. The Prp21p screen confirms known interactions with the two other SF3a subunits: Prp9p and Prp11p are found among the 13 different ORFs. Prp11p is the only A1 candidate. Note that Prp9p which interacts with Prp21p in its amino-terminal domain (Legrain et al., 1993) was selected as an A2 candidate, illustrating our prediction regarding this category. Finally, we note the presence of a common A2/A3 candidate, Ynr053c, in the Prp9p, Prp11p and Prp21p screens. The YNR053C gene contains an intron downstream of a large exon 1 (810 nt) and we always select the same fusion including the two exons.

The Cus1p screen selected thirteen clones, all falling in six yeast ORFs (Table 7). Yor319w found as an A2 candidate exhibits a strong homology with SAP49, one of the human SF3b components (Wells et al., 1996) and was chosen as a second round bait.

Example 4

Second and Third Round Two-hybrid Screens with Unknown Proteins Reveal Novel Interactions with Relevant Known Proteins Four proteins of unknown functions selected as A1 or A2 candidates were chosen for second round screening (Table 8). In three screens (Yer029c, Ylr456w and Ylr116w) the initial bait (SmD3p, Yir009w and Mud2p, respectively) was not found in the set of preys. In addition, in Yer029c and Ylr456w screens, no A1 candidate was found and no further experiments were performed with these proteins. The Ylr116w screen selected 11 ORFs, including two A1 (Smy2p and Lpg4p). Two splicing factors, Prp39p and Prp22p, were found among the preys. Thus, an unknown protein, Ylr116W, selected as prey with a splicing factor, Mud2p, can in turn select splicing factors, strongly suggesting that Ylr116w itself participates in the splicing pathway. Furthermore, the Mud2p and Ylr116w screens have several preys in common, including Smy2p, Lpg4p and Prp39p, suggesting that these five proteins participate in a common complex.

The Yor319w screen selected 9 preys falling in 4 different ORFs, two being in the A1 category. One of them is Cus1p, confirming the initial interaction detected with this protein as bait (Table 7). The second A1 candidate is Yjr022w. A careful analysis of its aminoacid sequence revealed that this protein contains the Sm motifs common to the core proteins of the snRNP particles (see Discussion). We used this Yjr022w protein as a bait for a third round two-hybrid screen (Table 9). Nineteen ORFs were selected, including the initial bait that selected Yjr022w (Yor319w). We also find two other Sm proteins including Uss1p, a U6 snRNP-associated protein (Cooper et al., 1995). This result suggests a connection between the U2 and U6 snRNPs (see Discussion).

A two-hybrid assay was also systematically performed with LexA-fusion baits for all preys selected in the Gal4-fusion screens (Tables 2–9). The LexA-fusion assay allows us to check whether the two-hybrid positive signal is independent from the DNA binding domain used as a fused polypeptide. Most preys selected by a Gal4-fusion were positive in the LexA-fusion assay, except for the Yir009w and the Yjr022w screens (6 and 9 negative preys out of 19, respectively). Thus, preys are mostly selected by the intrinsic domain of the bait fused to the Gal4 domain and not by the Gal4 domain itself or by a possible hinge domain formed in the fusion protein. However, we note that the experimental conditions for this two-hybrid assay are probably less stringent than those used during the screening procedure (see Experimental Procedures).

Altogether, 170 preys were selected in the 15 screens and correspond to 145 different ORFs, implicated in different cellular pathways. Nine ORFs are involved in pre-mRNA splicing, six in other RNA metabolisms, ten are involved in transcription and four are protein kinases or phosphatases. Other known ORFs are proteins implicated in many different functions. Fifty per cent of the selected ORFs correspond to new proteins for which one now has a starting point for a functional analysis. This proportion is similar, whether the screen is performed with a known protein (first round) or not (second and third round). Finally, among the selected ORFs, we note the presence of five unknown ORFs which exhibit homology with known human splicing factors. Ylr116w and Yor319w were recently found homologous to human splicing factors SF1 and SAP49, respectively (Arning et al., 1996; Wells et al., 1996) and Yer029c, Yjr022w and Yb1026w/Snp3p exhibit Sm motifs found in snRNP core proteins (see Discussion).

Example 5

Figure 5A:
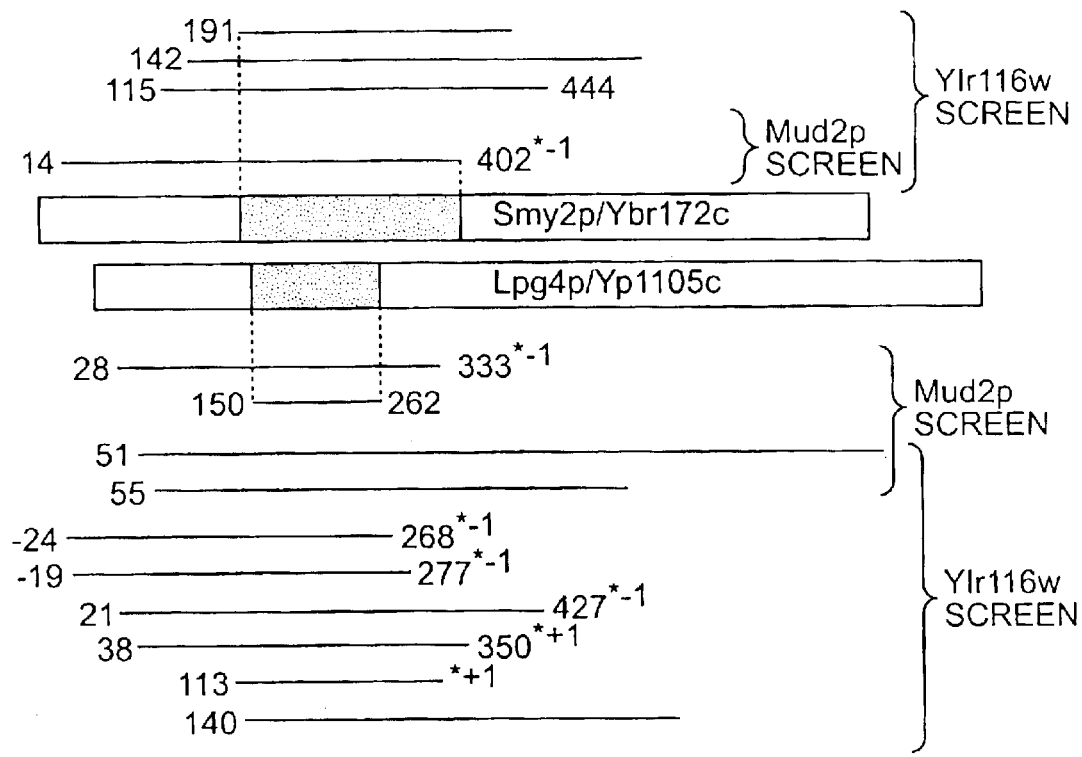
FIG. 5A. The position of inserts selected in Mud2p and Ylr116w screens and covering Smy2p (top) and Lpg4p (bottom) sequences are shown. The numbers indicate the amino acid residues. Out of frame fusions are labeled with an asterisk with the -1 or the +1 frameshift indicated. The minimal interacting domain is shaded.

Overlapping Fragments Selected in Two-hybrid Screens Define Interacting Domains A1 candidates correspond to independent fusions covering fragments of the same ORF. The comparison of the 5O and 3O junctions of these fusions allows the definition of a minimal fragment necessary for the interaction with the bait protein. Such an example for Smy2p and Lpg4p, two preys selected in the Mud2p and the Ylr116w screens, is illustrated in FIG. 5A. All clones share a common region. The deduced minimal fragment in Smy2p required for the interaction with Ylr116w covers 254 aminoacid residues (aa 191–402). Only one SMY2 fusion was selected in the Mud2p screen (aa 14–402). Similarly, the minimal fragments of Lpg4p sufficient for the interaction with Mud2p and Ylr116w can be determined: 113 residues (aa 150–262) and 129 residues (aa 140–268), respectively. In addition, Smy2p preys selected in the Ylr116w screen also interact with Mud2p and the smallest Lpg4p prey selected in the Mud1p screen interacts with Ylr116w (data not shown). This leads to a minimal size of 212 residues (aa 191–402) and 113 residues (aa 150–262) for the interacting domains in the Smy2p and Lpg4p proteins, respectively. Taking into account the fact that Smy2p and Lpg4p are homologous over their entire sequence (similarity: 55%; identity: 38%), our results strongly suggest that Lpg4p and Smy2p share a common domain that interacts with Mud2p and Ylr116w.

Figure 5B:
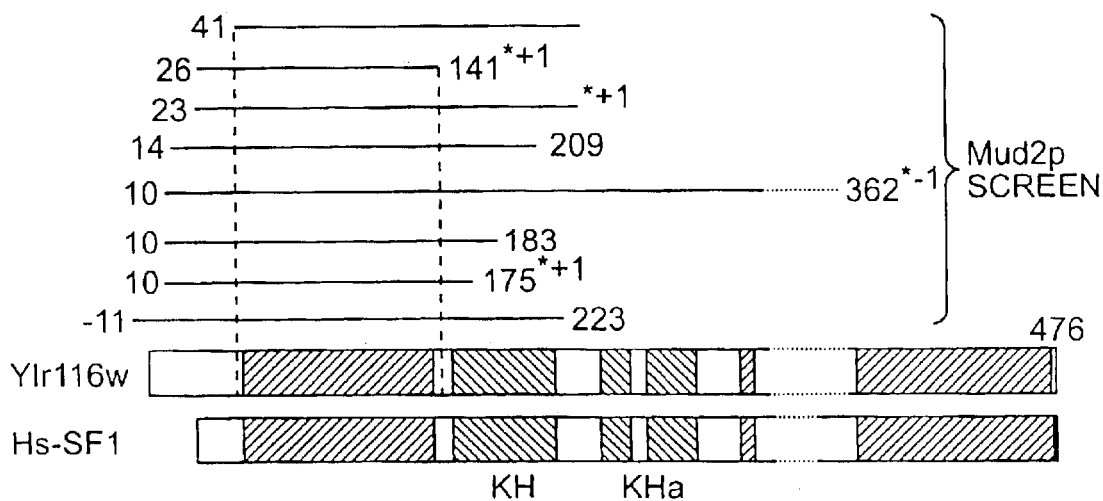
FIG. 5B. Inserts covering the Ylr116w sequence and selected in the Mud2p screen are shown. The alignment with the human SF1 protein is depicted with the positions of the regions of high homology (hatched) and of the KR and KH-associated motifs (in black).

Mud2p and Ylr116w also interact together (Table 4). Ylr116w and its human homologue SF1 contain a KH domain (FIG. 5B, Arning et al., 1996). The minimal interacting domain of Ylr116w with Mud2p (aa 41–141) is located upstream the KH domain and corresponds to a very conserved region between the yeast and human proteins (FIG. 5B).

Prp9p and Prp11p were previously shown to interact with Prp2 1p through domains that were defined by point mutant and deletion mutant analyses (Legrain and Chapon, 1993; Legrain et al., 1993; Rain et al., 1996). Here we determine more precisely the interacting domains of Prp21p with Prp9p and Prp11p and of Prp11p with Prp21p (data not shown). Similarly, we also characterize an interaction between Cus1p and a novel subunit of the yeast SF3b, Yor319w. The interacting domain is located in the carboxy-terminal region of Cus1p (aa 244–436). In conclusion, the characterization of A1 inserts selected in two-hybrid screens allows the delineation of a minimal fragment necessary for interaction.

Example 6

Many Novel ORFs Revealed in Two-hybrid Screens are Essential for Viability

Many selected preys correspond to new uncharacterized ORFs. We disrupted fifteen of these ORFs selected as A1, A2 or A3 candidates. Seven disrupted strains exhibit no growth phenotype (YDR386W, YJR033C, YJR039W, YLR456W, YMR285C, YNL023C, YPL105C), one has a slow growth phenotype (YLR357W) and seven disruptions are lethal (YDR180W, YER029C, YHR197W, YJR022W, YLR116W, YMR117C, YNR053C). This list of new essential proteins includes i) Ynr053c, that was selected in several two-hybrid screens (Tables 6, 8 and 9), ii) one new splicing factor: Ylr116w, the yeast homologue of human SF1, and iii) Yer029c and Yjr022w which exhibit Sm motifs. The three latter disruptions can be complemented with fusion genes selected in the two-hybrid screens, indicating that the Gal4 fused domain has no detrimental effect and that these fusion proteins can be used as tagged proteins.

Example 7

Out of Frame Fusion Genes are Selected in Two-hybrid Screens and Produce Frameshifted Polypeptides Among the 29 A1 ORFs selected in the 15 screens, nine include inserts with out of frame fusions, two of which only represented as out of frame fusions (see Tables 2–9). This result demanded a more careful analysis. Eight inserts overlapping the YPL105C ORF were selected in the Ylr116w screen (FIG. 5A). Five out of eight inserts are fused out of frame with the Gal4 domain (three in the −1 frame and two in the +1 frame). In both groups, different polypeptides are produced when translation occurs in frame with the Gal4 domain. Similarly, all inserts overlapping with the YEL015W ORF selected in the Yjr022w screen are in the −1 or in the +1 frame and encode different polypeptides in the Gal4 frame (data not shown). Statistically, the selection of these inserts at the same locus via the production of different polypeptides is most unlikely. It certainly occurs through the production of frameshifted polypeptides.

This conclusion is supported by two independent experiments of functional complementation. Genetic defects were corrected by the expression of a frameshifted fusion ORF. Prp11p was selected in the Prp21p screen as multiple independent inserts, including a +1 frameshift starting at nucleotide 159 and containing the remainder of the ORF. Mutant prp11$^{ts}$ cells grow at 37$_t$C when transformed with this plasmid or with the pPL20 plasmid encoding the PRP11 wildtype gene as opposed to prp11$^{ts}$ cells transformed with the pACTII vector (data not shown). Ylr116w was selected several times in the Mud2p screen (Table 4, FIG. 5B), including once as a −1 frameshift fusion (aa 10–362). We first showed that YLR116W is an essential gene: fifteen tetrads dissected from a diploid strain deleted for one YLR116W allele with a TRP1 cassette exhibit only two viable spores each, none of them being trp+. This diploid strain was transformed with the plasmid potentially producing the Ylr116w frameshifted fusion protein and the resulting cells were sporulated. Ten tetrads were dissected: two and four tetrads each exhibited 3 and 4 viable spores, respectively. The additional spores were trp+ leu+, demonstrating that the viability depends upon the presence of the LEU2 plasmid carrying the frameshifted fusion gene. In conclusion, we demonstrate that frameshift events, corresponding to a −1 and a +1 reading, can occur and are indeed selected in two-hybrid screens via the production of the frameshifted fusion protein.

Discussion

Improvement and Standardization for a Rational Use of the Two-hybrid Screen

Two-hybrid screens have been mostly used to find an appealing partner for a given protein. Many positive clones are usually discarded because their sequence is not related to any known protein or because the identified protein has no expected link with the protein used as bait. Here we report a reproducible strategy for exhaustive two-hybrid screens. This approach is based on the multiple round screening of a yeast genomic DNA library. The methodological improvements are: i) the routine analysis of the complete yeast genomic library for each screening; ii) a very strong selectivity; iii) the identification of all candidates by sequence; iv) a classification of candidates that reflects their worth for a new screen without speculating on their function (new baits chosen among A1, A2 and A3 categories); and v) the specificity of the identified interactions that comes out from the multiplicity of the screens.

The strong point of this strategy is its exhaustivity. The library contains one random fusion every 4 nucleotides, allowing a fairly good coverage of the genome. The library is exhaustively screened in each mating experiment. The mating strategy is very easy, highly reproducible, and allows controlled screening experiments to be performed with exactly the same library. We favor the mating protocol on filters followed by direct plating on selective medium instead of replica-plating diploids (Bendixen et al., 1994) or transformation since our protocol allows a larger number of interactions to be tested. This contrasts with two-hybrid screens of yeast genomic libraries that have been previously reported. In most cases, a limited number of interactions was tested (usually between 4×104 and 4×105, Bendixen et al., 1994; He and Jacobson, 1995; Stutz et al., 1995). In these experiments a low coverage of the yeast genome was achieved and screening was not exhaustive. Moreover, our results show that for preys found as multiple independent fusions, many expected fusions were not selected, probably due to problems in expression, stability or folding of fusion proteins. This emphasizes the importance of screening many interactions for recovering a set of interacting partners as complete as possible.

The fifteeen screens presented in this study show that proteins used as baits behave differently (FIG. 4). These data suggest that the distribution profile in categories of preys reflects an intrinsic property of the bait protein. Some profiles are simpler than others; the reasons for this are so far unexplainable. We expect that increasing the number of screens will probably reveal common features shared by proteins exhibiting the same profile and will facilitate the choice of future baits.

The selection of multiple independent fusions for a given prey allows the definition of an interacting domain. This is an efficient and reliable alternative strategy to the analysis of multiple deletion mutants that must otherwise be constructed (He et al., 1996; Iwabuchi et al., 1993; Rain et al., 1996). We describe also that out of frame fusions are frequently selected and we show that, indeed, frameshifted polypeptides are produced. Both +1 and −1 frameshifts have been reported in yeast and might occur at high levels (Stahl et al., 1995). The production of out of frame fusions can be advantageous in two-hybrid screening since in frame fusions may represent dominant negative mutants that could be counterselected. Such an example is found with Prp11p preys found in the Prp21p screen (Table 6, see also Fields and Jang, 1996; Legrain and Chapon, 1993). Finding expressed out of frame fusion genes emphasizes the importance of the identification of the interacting clone independently of its theoretical coding capacity, which can best be done in a yeast genomic library screening due to the availability of the complete sequence of the genome.

Multiple Rounds of Exhaustive Two-hybrid Screens Establish Physical Links Between Functionally Related Proteins We are aware that the interactions defined by two-hybrid assays would not cover all possible interactions, neither would all interactions be directly assessed as biologically relevant. However, our multiple round strategy has been used successfully to identify physical links between several proteins implicated in nuclear pre-mRNA splicing. First, we confirm interactions between Prp9p, Prp11p and Prp21p that were previously demonstrated (Legrain and Chapon, 1993; Legrain et al., 1993). Secondly, new splicing factors are identified in the series of screens started with Cus1p, a yeast homologue of the human SAP145 protein which is a component of the SF3b splicing factor (Champion and Reed, 1994). We first found that Cus1p interacts with Yor319w, a yeast protein identified as highly homologous with human SAP49, a second component of the SF3b factor shown by in vitro experiments to interact with SAP145 (Champion and Reed, 1994). Then we identified a small protein in the Yor319w screen, Yjr022w, that exhibits the Sm1 and Sm2 motifs found in core proteins of the snRNP particles (Hermann et al., 1995; Seraphin, 1995). A third round of screening with Yjr022w used as bait selected two additional Sm proteins, Yb1026w and Uss1p. The latter protein has been shown to be associated with the U6 snRNP. Thus, this series of two-hybrid screens identifies several novel yeast splicing factors (Yor319w, Yjr022w, Yb1026w) and suggests functional links between the U2 snRNP and the U6 snRNP. The association of U2 and U6 snRNPs is required in the mature spliceosome, but the molecular basis of this association is so far unknown. Yjr022w and Yb1026w could either be components of a novel complex that bridges the U2 and the U6 snRNPs or could be U6 snRNP-associated proteins.

Figure 6:
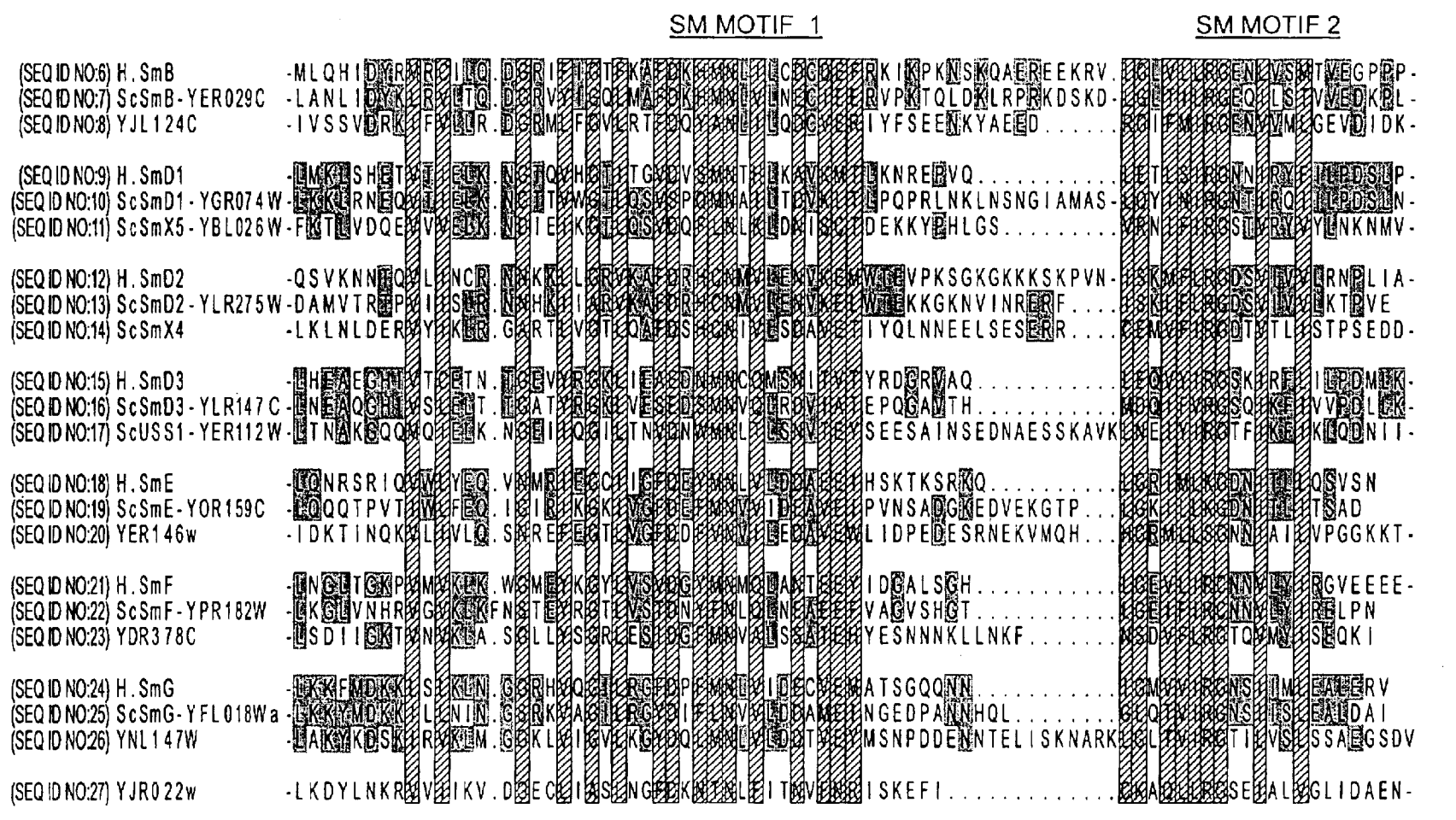

It has been suggested that two sets of Sm proteins are associated with the U1, U2, U4 and U5 snRNP, and with the U6 snRNP, respectively, each member of a set being more closely related to a given member of the other set (FIG. 6, Seraphin, 1995). Eight proteins constitute the U1–U5 core particles in mammalian cells (Sm B and B', derived from the same gene by alternative splicing, D1, D2, D3, E, F and G) whereas no human U6-associated Sm protein has been identified so far. In yeast, at least five Sm proteins are found associated with the yeast U1–U5 snRNPs and are named after their strongest homology with human Sm proteins: SmD1, SmD3, SmE, SmF/SmX3 and SmG/SmX2 (Bordonn and Tarassov, 1996; Roy et al., 1995; Rymond et al., 1993; Seraphin, 1995). In addition, two other Sm proteins, Uss1p and SmX4p, are found associated with the U6 snRNP (Cooper et al., 1995; Seraphin, 1995). In order to assign Yjr022w and Yb1026w to one of these two sets, we first identified all possible yeast Sm proteins in the complete yeast genome database. Fifteen proteins were found to exhibit both Sm1 and Sm2 motifs (FIG. 6). Two proteins were identified as the best homologues to human SmD2 (Ylr275w) and SmB (Yer029c) proteins, respectively (FIG. 6). We note that we found Yer029c in the SmD3p screen, in accord with biochemical studies that have shown direct physical interactions between the human SmB and SmD3 proteins (Raker et al., 1996). Each of the remaining yeast Sm proteins, except Yjr022w, is more similar to one of the U1–U5 associated proteins, suggesting indeed that a set of seven proteins, including Yb1026w, might be associated with the U6 snRNP particle (FIG. 6). Yjr022w cannot be best aligned with a particular member of the family, suggesting that this protein plays a slightly different role than other Sm proteins.

Wide Scale Two-hybrid Screens Opens the Possibility to Explore Novel Functional Links Between Gene Products In addition to interactions found between splicing factors, the finding of common preys in different screens suggests additional functional links. We identified interactions between Mud2p, Ylr116w, Smy2p, Lpg4p and Prp39p that might constitute a novel biochemical complex. We found a novel ORF, Ynr053c, that is selected with six proteins including Prp9p, Prp11p and Prp21p. Ynr053c is highly homologous (55% identity, 71% similarity) to a recently described human protein responsible for auto-immune responses (Racevskis et al., 1996). Many of such human proteins are implicated in RNA processing (van Venrooij and Pruijn, 1995). We also note that well-known transcriptional activators (such as Swi1p) were often selected by several baits. The selection of transcriptional activators in two-hybrid screens is a common finding (Bartel et al., 1993) and prevents us from seriously considering these candidates as interacting proteins. However, functional links between the transcriptional machinery and the processing of primary transcripts certainly exist. Repeating two-hybrid screens on a wide scale will unambiguously identify the auto-activating domains of transcriptional activators that will be rationally discarded. Then, the characterization of true interacting domains for transcription factors will become feasible.

Links are also found with proteins known to interfere with RNA metabolism or with nucleo-cytoplasmic transport such as Los1p and Sen1p or Mtr3p and Nup157p, respectively. However, the most intriguing result may be the selection in our two-hybrid screens of proteins that are not supposed to be connected with pre-mRNA processing, such as the cytoplasmic translational factors Tif4631 and Tif4632 selected in the Prp11p screen. These two proteins are implicated in the binding to the capped mRNAs and interfere with the initiation of translation. These interactions are unambiguously identified in two-hybrid screens, and their biological relevance must now be assessed. They may represent functional links that were unreached through classical genetics or biochemical purification. Finally, we also identify many unknown yeast proteins as interacting partners. Specific assays can now be applied to these new proteins in order to assess their function.

The strategy described here is fast, reliable and efficient. It allows us to consider a wide scale analysis of yeast gene products through two-hybrid screens. Without further technical improvements which are nevertheless in progress, several tens of screens can be performed within a year by a single researcher. Starting with baits chosen in different biochemical pathways one will progressively build networks of protein-protein connections. This approach will constitute one of the possible large scale analyses of the yeast genome and should ultimately define an interacting matrix within the yeast proteome.

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

TABLE 1

Characteristics of multiple rounds of two-hybrid screens.

| Two-hybrid screen | biochemical entity | baits[a] | diploids ($\times 10^6$) | His[+] colonies | LacZ[+] colonies | identified clones[b] |
|---|---|---|---|---|---|---|
| 1st round | Sm core particle | Smd1p | 40 | 88 | 40 | 36 |
| | | Smd3p | 52 | 243 | 50 | 47 |
| | U1 snRNP | Snp1p | 25 | 700 | 48 | 46 |
| | | Mud1p | 35 | 83 | 10 | 9 |
| | | Mud2p[c] | 57 | 17000 | 61 | 61 |
| | U2snRNP | Yir009w | 50 | 1700 | 82 | 81 |
| | yeast SF3a | Prp9p | 40 | 150 | 66 | 66 |
| | | Prp11p | 48 | 5800 | 86 | 85 |
| | | Prp21p | 58 | 530 | 66 | 21[d] |
| | yeast SF3b | Cus1p | 60 | 150 | 15 | 13 |
| 2nd round | prey of Smd3p | Yer029c | 40 | 58 | 10 | 9 |
| | prey of Mud2p | Ylr116w | 12 | 800 | 52 | 50 |
| | prey of Yir009w | Ylr456w | 39 | 330 | 22 | 21 |
| | prey of Cus1p | Yor319w | 40 | 130 | 10 | 9 |
| 3rd round | prey of Yor319w | Yjr022w | 96 | 10000 | 74 | 65 |

[a]baits are Gal4 fusions except Prp9p which is a LexA fusion.
[b]these numbers correspond to clones for which the sequence was determined and the phenotype double-checked (see Experimental procedures).
[c]Mud2p is not an U1 snRNP protein but is found associated with U1 snRNP in early spliceosomal complexes.
[d]the LacZ assay for Prp21p screening was performed on filter instead of following the overlay procedure, resulting in a poor viability of the yeast cells.

TABLE 2

ORF candidates found in Gal4-Smd1p and Gal4-Smd3p two-hybrid screens.

| ORF[a] | Cat.[b] | Number[c] | LexA[d] | Gene[e] | Function[f] |
|---|---|---|---|---|---|
| Smd1p bait | | | | | |
| YBR043c | A4* | 2 | +++ | | |
| YDR088C | A3* | 2 | + | SLU7 | pre-mRNA splicing |
| YDR389W | A4 | 1 | ++ | SAC7 | |
| YGL202w | A4 | 2 | ++ | | |
| YJR033c | A1* | 4 (2*) | +++ | | |
| YKL188c | A1 | 3 (2) | +++ | | |
| YKL205w | A4 | 3 | ++ | LOS1 | pre-tRNA splicing |
| YLR440c | A4 | 2 | + | | |
| Smd3p bait | | | | | |
| YBR114w | A4 | 1 | +++ | RAD16 | DNA repair |
| YER029c | A1 | 17 (3 & 2*) | +++ | | |
| YGR290w | A2* | 1 | − | | |
| YHR107c | A4 | 1 | ++ | CDC12 | cytokinesis |
| YHR178w | A4 | 1 | +++ | | |
| YIL139c | A4 | 2 | +++ | REV7 | DNA polymerase subunit |
| YKR080w | A4 | 1 | ++ | MTD1 | NAD-dependent dehydrogenase |
| YLL021w | A1 | 4 (3) | +++ | SPA2 | cell polarity |
| YLR430w | A4 | 1 | +++ | SEN1 | pre-tRNA splicing |
| YLR433c | A4 | 1 | ++ | CNA1 | serine/threonine phosphatase 2B |
| YMR088c | A4* | 1 | +++ | | |

[a]All yeast ORFs found in the screen are listed.
[b]The categories are those defined in FIG. 1. An asterisk indicates an out of frame fusion.
[c]The number of clones obtained is indicated with the number of independent fusions into brackets.
[d]The result of two-hybrid assays performed with a LexA-bait fusion protein are presented.
−: no growth on −his plates; +: growth on −his plates and white colonies in a X-Gal assay; ++: blue His+ colonies in a X-Gal assay after 3 hours incubation; +++: blue His+ colonies in a X-Gal assay after 1 hour incubation.
[e]A gene name is given when available (YPD, Garrels, 1996).
[f]the enzymatic activity or the cellular pathway are indicated when assigned.

TABLE 3

ORF candidates found in Gal4-Snp1p and Gal4-Mud1p two-hybrid screens.

| ORF[a] | Cat.[b] | Number[c] | LexA[d] | Gene[e] | Function[f] |
|---|---|---|---|---|---|
| Snp1p bait | | | | | |
| YAL047c | A4 | 1 | ++ | | |
| YBL063w | A4 | 1 | − | KIP1 | mitotic spindle |
| YBR112c | A1 | 3 (3) | +++ | SSN6 | transcription |
| YBR117c | A4 | 1 | − | TKL2 | transketolase 2 |
| YCR101c | A4 | 1 | ++ | | |
| YDL013w | A4 | 2 | ++ | HEX3 | |
| YDR110w | A2/3 | 1 | ++ | | |
| YER105c | A4 | 1 | ++ | NUP157 | nucleopore |
| YER172c | A3 | 1 | +++ | BRR2 | pre-mRNA splicing |
| YFL016c | A4 | 1 | − | MDJ1 | mitochondrial heat shock protein |
| YFR039c | A4 | 1 | + | | |
| YGR203w | A4 | 1 | + | | |
| YHR023w | A4* | 3 | − | MYO1 | myosin heavy chain |
| YHR079c | A2/3 | 3 | +++ | IRE1 | protein kinase |
| YLR017w | A4 | 1 | ++ | | |
| YLR153c | A4 | 1 | ++ | ACS2 | acetyl-coA synthetase 2 |
| YLR213c | A2/3* | 1 | ++ | | |
| YLR439w | A4 | 1 | ++ | MRPL4 | mitochondrial ribosomal protein |
| YML016c | A3* | 1 | ++ | PPZ1 | serine/threonine phosphatase |
| YMR009w | A1 | 2 (2) | ++ | | |
| YMR044w | A4 | 1 | +++ | | |
| YNL199c | A4 | 1 | +++ | GCR2 | transcription |
| YNR016c | A4 | 1 | − | FAS3 | acetyl-coA carboxylase |
| YOL004w | A3 | 4 | ++ | SIN3 | transcription |
| YOR275c | A1 | 2 (2) | ++ | | |
| YOR346w | A1 | 2 (2) | +++ | REV1 | |
| YPL016w | A1 | 2 (2) | ++ | SWI1 | transcription |
| YPL215w | A4 | 1 | ++ | CBP3 | |

TABLE 3-continued

ORF candidates found in Gal4-Snp1p and Gal4-Mud1p two-hybrid screens.

| ORF[a] | Cat.[b] | Number[c] | LexA[d] | Gene[e] | Function[f] |
|---|---|---|---|---|---|
| Mud1p bait | | | | | |
| YDR110w | A2 | 3 | +++ | | |
| YLR223c | A4 | 1 | +++ | RRP3 | pre-rRNA processing |
| YLR449w | A4* | 2 | ++ | | |
| YML016c | A4 | 1 | +++ | PPZ1 | serine/threonine phosphatase |
| YNL227c | A2/3 | 1 | ++ | | |

For legends see Table 2.

TABLE 4

ORF candidates found in a Gal4-Mud2p two-hybrid screen.

| ORF[a] | Cat.[b] | Number[c] | LexA[d] | Gene[e] | Function[f] |
|---|---|---|---|---|---|
| YBR172C | A2/3* | 3 | ++ | SMY2 | |
| YGL035C | A2 | 1 | ++ | MIG1 | transcription |
| YLR116w | A1 | 41 (4 & 4*) | +++ | | |
| YLR357w | A3 | 1 | +++ | | |
| YML046w | A2/3 | 1 | +++ | PRP39 | pre-mRNA splicing |
| YPL016w | A1 | 2 (2) | ++ | SWI1 | transcription |
| YPL105c | A1 | 9 (3 & 1*) | +++ | LPG4 | |

For legends, see Table 2.

TABLE 5

ORF candidates found in a Gal4-Yir009w (yeast U2B") two-hybrid screen.

| ORF[a] | Cat.[b] | Number[c] | LexA[d] | Gene[e] | Function[f] |
|---|---|---|---|---|---|
| YAL024c | A2/3 | 1 | ++ | LTE1 | cell cycle |
| YBR114w | A4 | 1 | – | RAD16 | DNA repair |
| YBR136w | A4 | 2 | + | MEC1 | cell cycle |
| YDL001w | A4 | 4 | ++ | | |
| YDR184c | A4 | 3 | +++ | | |
| YHR099w | A4 | 2 | ++ | | |
| YHR197w | A3 | 1 | ++ | | |
| YIL143c | A2 | 1 | – | SSL2 | transcription |
| YJL092w | A3 | 1 | +++ | SRS2 | DNA helicase |
| YKL173w | A4 | 2 | ++ | GIN10 | |
| YKR099w | A3 | 1 | – | BAS1 | transcription |
| YLR067c | A2/3 | 1 | – | PET309 | mitochondrial translation |
| YLR433c | A4 | 1 | – | CNA1 | serine/threonine phosphatase 2B |
| YLR456w | A1 | 9 (6) | ++ | | |
| YNL036w | A1 | 2 (2) | ++ | NCE3 | non-classical protein export |
| YNL091w | A4 | 2 | ++ | | |
| YOR011w | A2 | 6 | ++ | | |
| YOR017w | A4 | 1 | – | PET127 | mitochondrial translation |
| YPL016w | A4 | 1 | ++ | SWI1 | transcription |

For legends, see Table 2.

TABLE 6

ORF candidates found in LexA-Prp9p, Gal4-Prp11p and Gal4-Prp21p two-hybrid screens.

| ORF[a] | Cat.[b] | Number[c] | LexA[d] | Gene[e] | Function[f] |
|---|---|---|---|---|---|
| Prp9p bait | | | | | |
| YCL060c | A4* | 3 | nd[g] | | |
| YCL061c | A4 | 1 | | | |
| YDL013w | A2 | 2 | | HEX3 | |
| YDR421W | A3 | 1 | | | |
| YDR485c | A1 | 5 (3) | | | |
| YJL203w | A4 | 1 | | PRP21 | pre-mRNA splicing |
| YML049c | A3 | 2 | | | |
| YML104c | A4 | 1 | | MDM1 | intermediate filament |

TABLE 6-continued

ORF candidates found in LexA-Prp9p, Gal4-Prp11p and Gal4-Prp21p two-hybrid screens.

| ORF[a] | Cat.[b] | Number[c] | LexA[d] | Gene[e] | Function[f] |
|---|---|---|---|---|---|
| YMR005w | A4 | 1 | | MPT1 | |
| YNR053C | A2/3 | 1 | | | |
| YOR017w | A2 | 1 | | PET 127 | mitochondrial translation |
| YOR023c | A4 | 4 | | | |
| YOR191w | A4 | 2 | | | |
| YPL146c | A2 | 1 | | | |
| Prp11p bait | | | | | |
| YBR113w | A4* | 1 | +++ | | |
| YDR131c | A4 | 1 | ++ | | |
| YDR180w | A3 | 1 | + | | |
| YDR386w | A1 | 2 (2) | ++ | | |
| YDR409w | A4 | 1 | ++ | | |
| YER113c | A4 | 4 | +++ | | |
| YGL049C | A1 | 3 (2) | +++ | TIF4632 | cytoplasmic translation |
| YGR162w | A4 | 1 | +++ | TIF4631 | cytoplasmic translation |
| YJL146w | A4 | 4 | +++ | IDS2 | |
| YJL203w | A1 | 11 (4) | +++ | PRP21 | pre-mRNA splicing |
| YKL155c | A1 | 5 (5) | +++ | | |
| YLL014w | A4* | 1 | + | | |
| YMR117c | A1 | 2 (2) | +++ | | |
| YMR302c | A4 | 2 | +++ | RNA12 | pre-rRNA processing |
| YNL023c | A3 | 1 | +++ | | |
| YNR053c | A2/3 | 3 | +++ | | |
| YPL215w | A2 | 2 | ++ | CBP3 | |
| Prp21p bait | | | | | |
| YBL067c | A4 | 1 | − | UBP13 | ubiquitin carboxyl-terminal hydrolase |
| YBL101c | A2* | 1 | ++ | | |
| YCR081w | A4 | 1 | ++ | SRB8 | transcription |
| YDL030w | A2 | 1 | +++ | PRP9 | pre-mRNA splicing |
| YDL043c | A1 | 4 (1 & 3*) | +++ | PRP11 | pre-mRNA splicing |
| YDR170c | A4 | 1 | ++ | SEC7 | non-clathrin vesicle coat |
| YHL007C | A4 | 3 | +++ | STE20 | serine/threonine kinase |
| YKR090W | A4 | 1 | +++ | | |
| YLR067c | A2/3 | 2 | − | PET309 | mitochondrial translation |
| YMR285c | A2 | 1 | ++ | | |
| YNR053c | A2/3 | 1 | ++ | | |
| YOL091w | A4 | 1 | +++ | | |
| YOL136c | A4 | 1 | +++ | PFK27 | 6-phosphofructose-2-kinase |

For legends, see Table 2.
[g]This assay is not relevant for Prp9p since the screen is made with a LexA-Prp9p fusion.

TABLE 7

ORF candidates found in a Gal4-Cus1p two-hybrid screen.

| ORF[a] | Cat.[b] | Number[c] | LexA[d] | Gene[e] | Function[f] |
|---|---|---|---|---|---|
| YBR112c | A4 | 1 | + | SSN6 | transcription |
| YER172c | A1 | 4 (2) | ++ | BRR2 | pre-mRNA splicing |
| YGL035c | A2 | 2 | | MIG1 | transcription |
| YLR090w | A4 | 2 | ++ | XDJ1 | |
| YOR319w | A2 | 2 | +++ | HSH49 | |
| YPL016w | A1 | 2 (2) | ++ | SWI1 | transcription |

For legends, see Table 2.

TABLE 8

ORF candidates found in second round two-hybrid screens.

| ORF[a] | Cat.[b] | Number[c] | LexA[d] | Gene[e] | Function[f] |
|---|---|---|---|---|---|
| Yer029c bait | | | | | |
| YDR422c | A3 | 2 | +++ | SIP1 | transcription |
| YLR220w | A2/3 | 1 | ++ | CCC1 | |

TABLE 8-continued

ORF candidates found in second round two-hybrid screens.

| ORF[a] | Cat.[b] | Number[c] | LexA[d] | Gene[e] | Function[f] |
|---|---|---|---|---|---|
| YNL187W | A2/3* | 2 | +++ | | |
| YNR053c | A2/3 | 2 | – | | |
| Ylr456w bait | | | | | |
| YER032w | A4 | 1 | ++ | | |
| YIL144w | A4* | 1 | – | | |
| YKR084c | A4 | 1 | +++ | HBS1 | |
| YNR053c | A2/3 | 3 | – | | |
| Ylr116w bait | | | | | |
| YBR172C | A1 | 6 (4) | +++ | SMY2 | |
| YDL156w | A2 | 1 | – | | |
| YDL161w | A4 | 1 | ++ | | |
| YER013w | A3 | 2 | ++ | PRP22 | pre-mRNA splicing |
| YIL130w | A4 | 1 | ++ | | |
| YJR005w | A2/3 | 1 | ++ | YAP80 | clathrin-associated complex |
| YJR066w | A3 | 1 | ++ | TOR1 | phosphatidylinositol kinase |
| YML046w | A2* | 1 | – | PRP39 | pre-mRNA splicing |
| YMR065w | A3 | 1 | ++ | | |
| YPL016w | A4 | 2 | ++ | SWI1 | transcription |
| YPL105c | A1 | 13 (3 & 5*) | +++ | LPG4 | |
| Yor319w bait | | | | | |
| YGR056W | A4 | 1 | – | | |
| YHR209W | A4 | 3 | +++ | | |
| YJR022w | A1 | 2 (2) | +++ | | |
| YMR240c | A1 | 3 (2) | +++ | CUS1 | pre-mRNA splicing |

For legends, see Table 2.

TABLE 9

ORF candidates found in a third round two-hybrid screen using a Gal4-Yjr022w bait.

| ORF[a] | Cat.[b] | Number[c] | LexA[d] | Gene[e] | Function[f] |
|---|---|---|---|---|---|
| YBL026w | A1* | 4 (1 & 2*) | +++ | SNP3 | |
| YBR003w | A4 | 1 | – | COQ1 | Coenzyme Q biosynthesis |
| YCR077c | A4* | 1 | – | | |
| YDR228c | A1 | 2 (2) | ++ | | |
| YDR277c | A2/3 | 1 | – | MTH1 | transcription |
| YEL015w | A1* | 5 (3*) | – | | |
| YER112W | A2 | 1 | +++ | USS1 | pre-mRNA splicing |
| YGL096w | A1 | 2 (2) | ++ | | |
| YGL173c | A4 | 1 | – | KEM1 | RNA and DNA 5'-3' exonuclease |
| YGR158c | A2 | 1 | +++ | MTR3 | mRNA transport |
| YHR034c | A4 | 1 | +++ | | |
| YHR035w | A4 | 1 | ++ | | |
| YIL173w | A4 | 1 | – | | |
| YNL050c | A4* | 3 | +++ | | |
| YNL118c | A1 | 10 (2 & 3*) | – | PSU1 | |
| YNR050c | A4 | 1 | – | LYS9 | lysine biosynthesis |
| YNR053c | A2/3 | 7 | – | | |
| YOR076c | A3 | 1 | ++ | | |
| YOR319w | A2 | 1 | +++ | HSH49 | |

For legends, see Table 2.

References

Allen, J. B., Walberg, M. W., Edwards, M. C. & Elledge, S. J. (1995) *Trends Biochem. Sci.* 20, 511–6.

Alvarado-Urbina G. et al., 1986, Biochem. Cell. Biol., 64: 548–555.

Bartel, P. L., Roecklein, J. A., SenGupta, D. & Fields, S. (1996) Nat. Genet. 12, 72–77.

Chien, C. T., Bartel, P. L., Sternglanz, R. & Fields, S. (1991) *Proc. Natl. Acad. Sci. USA.* 88, 9578–82.

Crea R. et al., 1978, Proc. Natl. Acad. Sci. USA, 75(12): 5765–5769.

Fields, S. & Song, O. (1989) *Nature* 340, 245–6.

Finley R. L., 1994. Interaction mating reveals binary and ternary connections between *Drosophila* cell cycle regulators. Proc. Natl. Acad. Sci. USA, 91: 12980–12984.

Froehler B. C. et al., 1986, Nucleic Acids Research, 14(13): 5399–5407.

Hsiung H. M. et al., 1980, Nucleic Acids Research, 8(23): 5753–5765.

Keegan et al. (1986) Science 231, 699-407 and Ma and Ptashne (1987) Cell 48, 847–853.

Rossi, F., Charlton, C. A. & Blau, H. M. (1997) Proc. Natl. Acad. Sci. USA. 94, 8405–8410.

Sambrook, J. et al. 1989. In Molecular cloning: A Laboratory Manual. Cold Spring Harbor, N.Y.: Cold Spring Harbor Laboratory Press.

Sonveaux et al., 1986, Bioorganic Chemistry, 14: 274–325.

Transy, C. & Legrain, P. (1995) Mol. Biol. Rep. 21, 119–27.

Ullmann, A., Jacob, F. & Monod, J. (1968) J. Mol. Biol. 32, 1–13.

Urdea M. S. et al., 1983, Proc. Natl. Acad. Sci. USA, 80: 7461–7465.

Arning, S., GrÿYter, P., Graeme, B., and KrŠmer, A. (1996). Mammalian splicing factor SF1 is encoded by variant cDNAs and binds to RNA. RNA 2, 794–810.

Bartel, P., Chien, C. T., Sternglanz, R., and Fields, S. (1993). Elimination of false positives that arise in using the two-hybrid system. Biotechniques 14, 920–924.

Bartel, P. L., Roecklein, J. A., SenGupta, D., and Fields, S. (1996). A protein linkage map of *Escherichia coli* bacteriophage T7. Nature Genet 12, 72–7.

Baudin, A., Ozier-Kalogeropoulos, O., Denouel, A., Lacroute, F., and Cullin, C. (1993). A simple and efficient method for direct gene deletion in *Saccharomyces cerevisiae*. Nucleic Acids Res 21, 3329–3330.

Beggs, J. D. (1995). Yeast splicing factors and genetic strategies for their analysis. In Pre-mRNA Processing, A. I. Lamond, ed. (Heidelberg: Springer-Verlag), pp. 79–95.

Bendixen, C., Gangloff, S., and Rothstein, R. (1994). A yeast mating-selection scheme for detection of protein-protein interactions. Nucleic Acids Res 22, 1778–1779.

Bennett, M., and Reed, R. (1993). Correspondence between a mammalian spliceosome component and an essential yeast splicing factor. Science 262, 105–8.

Bordonn, R., and Tarassov, I. (1996). The yeast SME1 gene encodes the homologue of the human E core protein. Gene 176, 111–117.

Brosi, R., GrŠning, K., Behrens, S. E., LŸhrmann, R., and KrŠmer, A. (1993). Interaction of mammalian splicing factor SF3a with U2 snRNP and relation of its 60-kD subunit to yeast PRP9. Science 262, 102–5.

Burns, N., Grimwade, B., Ross-MacDonald, P. B., Choi, E. Y., Finberg, K., Roeder, G. S., and Snyder, M. (1994). Large-scale analysis of gene expression, protein localization, and gene disruption in *Saccharomyces cerevisiae*. Genes Dev 8, 1087–1105.

Champion, A. P., and Reed, R. (1994). The prespliceosome components SAP 49 and SAP 145 interact in a complex implicated in tethering U2 snRNP to the branch site. Genes Dev 8, 1974–1983.

Cooper, M., Johnston, L. H., and Beggs, J. D. (1995). Identification and characterization of Uss1p (Sdb23p): a novel U6 snRNA-associated protein with significant similarity to core proteins of small nuclear ribonucleoproteins. EMBO J 14, 2066–2075.

Dujon, B. (1996). The yeast genome project—What did we learn? Trends Genet 12, 263–270.

Elledge, S. J., Mulligan, J. T., Ramer, S. W., Spottswood, M., and Davis, R. W. (1991). Lambda YES: a multifunctional cDNA expression vector for the isolation of genes by complementation of yeast and *Escherichia coli* mutations. Proc Natl Acad Sci U S A 88, 1731–1735.

Fields, S., and Jang, S. K. (1996). Presence of a potent transcription activating sequence in the p53 protein. Science 249, 1046–1049.

Fields, S., and Song, O. (1989). A novel genetic system to detect protein-protein interactions. Nature 340, 245–246.

Garrels. (1996). The yeast proteome handbook, First Edition (Beverley: Proteome Inc.).

Goffeau, A., Barrell, B. G., Bussey, H., Davis, R. W., Dujon, B., Feldmann, H., Galibert, F., Hoheisel, J. D., Jacq, C., Johnston, M., Louis, E. J., Mewes, H. W., Murakami, Y., Philippsen, P., Tettelin, H., and Oliver, S. G. (1996). Life With 6000 Genes. Science 274, 546–567.

He, F., Brown, A. H., and Jacobson, A. (1996). Interaction between Nmd2p and Upf1p is required for activity but not for dominant-negative inhibition of the nonsense-mediated mRNA decay pathway in yeast. RNA 2, 153–170.

He, F., and Jacobson, A. (1995). Identification of a novel component of the nonsense-mediated mRNA decay pathway by use of an interacting protein screen. Genes Dev 9, 437–454.

Hermann, H., Fabrizio, P., Raker, V. A., Foulaki, K., Hornig, H., Brahms, H., and Luhrmann, R. (1995). snRNP Sm proteins share two evolutionarily conserved sequence motifs which are involved in Sm protein-protein interactions. EMBO J 14, 2076–2088.

Hollenberg, S. M., Sternglanz, R., Cheng, P. F., and Weintraub, H. (1995). Identification of a new family of tissue-specific basic helix-loop-helix proteins with a two-hybrid system. Mol Cell Biol 15, 3813–3822.

Iwabuchi, K., Li, B., Bartel, P., and Fields, S. (1993). Use of the two-hybrid system to identify the domain of p53 involved in oligomerization. Oncogene 8, 1693–1696.

KrŠmer, A. (1996). The structure and function of proteins involved in mammalian pre-mRNA splicing. Annu. Rev. Biochem. 65, 367–409.

Legrain, P., and Chapon, C. (1993). Interaction between PRP11 and SPP91 yeast splicing factors and characterization of a PRP9-PRP11-SPP91 complex. Science 262, 108–110.

Legrain, P., Chapon, C., and Galisson, F. (1993). Interactions between PRP9 and SPP91 splicing factors identify a protein complex required in prespliceosome assembly. Genes Dev 7, 1390–1399.

Legrain, P., Dokhelar, M. C., and Transy, C. (1994). Detection of protein-protein interactions using different vectors in the two-hybrid system. Nucleic Acids Res 22, 3241–3242.

Legrain, P., and Rosbash, M. (1989). Some cis- and trans-acting mutants for splicing target pre-mRNA to the cytoplasm. Cell 57, 573–583.

Povinelli, C. M., and Gibbs, R. A. (1993). Large-scale sequencing library production: an adaptor-based strategy. Anal Biochem 210, 16–26.

Racevskis, J., Dill, A., Stockert, R., and Fineberg, S. A. (1996). Cloning of a novel nucleolar guanosine 5'-triphosphate binding protein autoantigen from a breast tumor. Cell Growth & Differentiation 7, 971–280.

Rain, J.-C., Tartakoff, A. M., KrŠmer, A., and Legrain, P. (1996). Essential domains of the PRP21 splicing factor are implicated in the binding to PRP9 and PRP11 proteins and are conserved trough evolution. RNA 2, 535–550.

Raker, V. A., Plessel, G., and Luhrmann, R. (1996). The snRNP core assembly pathway: identification of stable core protein heteromeric complexes and an snRNP sub-core particle in vitro. EMBO J 15, 2256–2269.

Roy, J., Zheng, B., Rymond, B. C., and Woolford, J. L., Jr. (1995). Structurally related but functionally distinct yeast Sm D core small nuclear ribonucleoprotein particle proteins. Mol Cell Biol 15, 445–455.

Rymond, B. C., Rokeach, L. A., and Hoch, S. O. (1993). Human snRNP polypeptide D1 promotes pre-mRNA binding in yeast and defines non-essential yeast Smd1p sequences. Nucleic Acids Res. 21, 3501–3505.

Seraphin, B. (1995). Sm and Sm-like proteins belong to a large family: identification of proteins of the U6 as well as the U1, U2, U4 and U5 snRNPs. EMBO J 14, 2089–2098.

Stahl, G., Bidou, L., Rousset, J. P., and Cassan, M. (1995). Versatile vectors to study recoding: conservation of rules between yeast and mammalian cells. Nucleic Acids Res 23, 1557–1560.

Stutz, F., Neville, M., and Rosbash, M. (1995). Identification of a novel nuclear pore-associated protein as a functional target of the HIV-1 Rev protein in yeast. Cell 82, 495–506.

Tang, J., Abovich, N., and Rosbash, M. (1996) Identification and characterization of a yeast gene encoding the U2 small nuclear ribonucleoprotein particle B" protein. Mol Cell Biol 16, 2787–2795.

Transy, C., and Legrain, P. (1995). The two-hybrid: an in vivo protein-protein interaction assay. Mol. Biol. Rep. 21, 119–127.

van Venrooij, W. J., and Pruijn, G. J. (1995). Ribonucleoprotein complexes as autoantigens. Curr Opin Immunol 7, 819–24.

Vojtek, A. B., Hollenberg, S. M., and Cooper, J. A. (1993). Mammalian Ras interacts directly with the serine/threonine kinase Raf. Cell 74, 205–14.

Wells, S. E., Neville, M., Haynes, M., Wang, J., Igel, H., and Ares, M. J. (1996). CUS1, a suppressor of cold-sensitive U2 snRNA mutations, is a novel yeast splicing factor homologous to human SAP 145. Genes Dev 10, 220–232.

---

What is claimed is:

1. A method for selecting a polynucleotide encoding a prey polypeptide, said prey polypeptide being able to interact with a bait polypeptide, said method comprising:
   (A) providing a yeast cell mixture comprising a first population of yeast cells, which are not in a colony, containing at least one first haploid recombinant yeast cell containing a polynucleotide encoding said bait polypeptide (bait polynucleotide) and a second population of yeast cells, which are not in a colony, containing at least one second haploid recombinant yeast cell containing a polynucleotide encoding said prey polypeptide (prey polynucleotide);
   (B) subjecting said polynucleotide encoding said bait polypeptide to a two-hybrid screening method, wherein said two-hybrid screening method comprises a step of mating for a maximum of 5 hours, without replica plating, said at least one first haploid recombinant yeast cell containing said bait polynucleotide with said second haploid recombinant yeast cell containing said prey polynucleotide, provided that one haploid yeast cell among said first haploid recombinant yeast cell or said second haploid recombinant yeast cell also contains at least one detectable gene that is activated by a polypeptide including a transcriptional activation domain; and
   (C) selecting the recombinant diploid yeast cell obtained at step (B) for which said detectable gene has been expressed to a degree greater than expression in the absence of interaction between said bait polypeptide and said prey polypeptide.

2. The method as claimed in claim 1, further comprising repeating at least once steps (B) and (C) with a bait polynucleotide selected from the group consisting of:
   1) a polynucleotide that is identical to said selected prey polynucleotide;
   2) a polynucleotide containing the complete ORF including said selected prey polynucleotide; and
   3) a polynucleotide, which is any polynucleotide fragment comprised in the complete ORF, including said selected prey polynucleotide.

3. The method as claimed in claim 1, wherein the prey polynucleotide is contained within the plasmid pACTIIst.

4. The method as claimed in claim 1, wherein the prey polynucleotide is provided by a DNA library contained in the collection of recombinant E. coli strain MR32 cells deposited at the Collection Nationale de Culture de Microorganismes (C.N.C.M.) under the accession number 1-1651.

5. A method of screening for a prey potypeptide that interacts with a bait polypeptide, said method comprising:

(A) providing a yeast cell mixture comprising a first population of yeast cells, which are not in a colony, containing at least one first haploid recombinant yeast cell and a second population of yeast cells, which are not in a colony, containing at least one second haploid recombinant yeast cell, wherein said least one first haploid recombinant yeast cell comprises a polynucleotide encoding said bait polypeptide (bait polynucleotide), and wherein said at least one second haploid recombinant yeast cell comprises a polynucleotide encoding said prey polypeptide (prey polynucleotide)

(B) mating for a maximum of 5 hours, without replica plating, said at least one first haploid recombinant yeast cell with said at least one second haploid recombinant yeast cell to produce at least one recombinant diploid yeast cell, provided that said at least one first haploid yeast cell or said at least one second haploid recombinant yeast cell further comprises at least one detectable gene that is activated when said prey polypeptide and said bait polypeptide interact in said at least one recombinant diploid yeast cell; and (C) selecting said at least one recombinant diploid yeast cell obtained at step (B) for which said at least one detectable gene has been expressed to a degree greater than expression in the absence of interaction between said bait polypeptide and said prey polypeptide.

* * * * *